(12) United States Patent
Wimley et al.

(10) Patent No.: US 11,266,743 B2
(45) Date of Patent: Mar. 8, 2022

(54) PEPTIDE COMPOSITIONS AND METHODS OF USE THEREOF

(71) Applicant: The Administrators of the Tulane Educational Fund, New Orleans, LA (US)

(72) Inventors: William Charles Wimley, New Orleans, LA (US); Charles Gannon Starr, New Orleans, LA (US); William Berkeley Kauffman, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 16/758,791

(22) PCT Filed: Oct. 25, 2018

(86) PCT No.: PCT/US2018/057614
§ 371 (c)(1),
(2) Date: Apr. 23, 2020

(87) PCT Pub. No.: WO2019/084343
PCT Pub. Date: May 2, 2019

(65) Prior Publication Data
US 2020/0276322 A1 Sep. 3, 2020

Related U.S. Application Data

(60) Provisional application No. 62/577,420, filed on Oct. 26, 2017, provisional application No. 62/576,919, filed on Oct. 25, 2017.

(51) Int. Cl.
| | | |
|---|---|---|
| *A61K 47/64* | (2017.01) | |
| *A61P 31/04* | (2006.01) | |
| *A61P 35/00* | (2006.01) | |
| *C07K 7/06* | (2006.01) | |
| *C07K 7/08* | (2006.01) | |
| *C12N 15/11* | (2006.01) | |
| *G01N 33/53* | (2006.01) | |

(52) U.S. Cl.
CPC .............. *A61K 47/64* (2017.08); *A61P 31/04* (2018.01); *A61P 35/00* (2018.01); *C07K 7/06* (2013.01); *C07K 7/08* (2013.01); *C12N 15/11* (2013.01); *G01N 33/53* (2013.01); *C12N 2310/313* (2013.01); *C12N 2310/315* (2013.01)

(58) Field of Classification Search
CPC ......... A61K 38/00; A61K 47/64; A61P 31/04; A61P 35/00; C07K 7/02; C07K 7/06; C07K 7/08; C12N 15/11; C12N 2310/313; C12N 2310/315; G01N 33/53; Y02A 50/30

See application file for complete search history.

(56) References Cited

U.S. PATENT DOCUMENTS

| | | | |
|---|---|---|---|
| 10,253,099 B2 * | 4/2019 | Strieker | ............... A61K 47/645 |
| 2004/0147027 A1 | 7/2004 | Troy et al. | |
| 2011/0110937 A1 | 5/2011 | Simon | |
| 2014/0024597 A1 | 1/2014 | Troy et al. | |
| 2019/0211063 A1 | 7/2019 | Wimley et al. | |

FOREIGN PATENT DOCUMENTS

| | | |
|---|---|---|
| CA | 2991223 | 7/2019 |
| EP | 1724280 A1 | 11/2006 |
| EP | 2394665 A1 | 12/2011 |
| WO | WO-2016/142445 A2 | 9/2016 |

OTHER PUBLICATIONS

Subrizi et al. Tat(48-60) peptide amino acid sequence is not unique in its cell penetrating properties and cell-surface glycosaminoglycans inhibit its cellular uptake. J Controlled Release, 2012. vol. 158, pp. 277-285. (Year: 2012).*
Supplementary Partial European Search Report for Application No. 18871046.1, dated Jul. 22, 2021 (14 pages).
International Search Report and Written Opinion for International Application No. PCT/US18/57614, dated Feb. 25, 2019 (17 pages).
International Preliminary Report on Patentability for International Application No. PCT/US18/57614, dated Apr. 28, 2020 (7 pages).
Krauson et al., "Conformational Fine-Tuning of Pore-Forming Peptide Potency and Selectivity," J Am Chem Soc. 137(51): 16144-52 (2015).
Wiedman et al., "Highly Efficient Macromolecule-Sized Poration of Lipid Bilayers by a Synthetically Evolved Peptide," J Am Chem Soc. 136(12): 4724-31 (2014).
Wiedman et al., "Testing the limits of rational design by engineering pH sensitivity into membrane active peptides," available in PMC Apr. 1, 2016, published in final edited form as: Biochim Biophys Acta. 1848(4):951-7 (2015) (15 pages).
Farrand et al., "The Cholesterol-dependent Cytolysin Membrane-binding Interface Discriminates Lipid Environments of Cholesterol to Support β-Barrel Pore Insertion," J Biol Chem. 290(29): 17733-44 (2015).
Wiedman et al., "PH-Triggered, Macromolecule-Sized Poration of Lipid Bilayers by Synthetically Evolved Peptides," available in PMC Jul. 21, 2017, published in final edited form as: J Am Chem Soc. 139(2):937-45 (2017) (22 pages).
Hristova et al., "A look at arginine in membranes," available in PMC Jan. 1, 2012, published in final edited form as: J Membr Biol. 239(1-2):49-56 (2011) (13 pages).
Starr et al., "Pituitary adenylate cyclase-activating polypeptide is a potent broad-spectrum antimicrobial peptide: Structure-activity relationships," available in PMC Jun. 1, 2019, published in final edited form as: Peptides. 104:35-40 (2018) (19 pages).

(Continued)

Primary Examiner — Marcela M Cordero Garcia
(74) Attorney, Agent, or Firm — Clark & Elbing LLP

(57) ABSTRACT

Described herein are membrane permeabilizing peptides and antimicrobial peptides, polynucleotides encoding the peptides, and compositions containing the peptides. Furthermore, described herein are methods for using the peptides, polynucleotides, and compositions for research, diagnosis, and therapy.

16 Claims, 62 Drawing Sheets
(58 of 62 Drawing Sheet(s) Filed in Color)
Specification includes a Sequence Listing.

(56) References Cited

OTHER PUBLICATIONS

Starr et al., "Antimicrobial peptides are degraded by the cytosolic proteases of human erythrocytes," available in PMC Dec. 1, 2018, published in final edited form as: Biochim Biophys Acta. 1859(12):2319-26 (2017) (20 pages).

Wimley, "Application of Synthetic Molecular Evolution to the Discovery of Antimicrobial Peptides," available in PMC Oct. 8, 2019, published in final edited form as: Adv Exp Med Biol. 1117:241-255 (2019) (20 pages).

Wimley et al., "Antimicrobial Peptides: successes, challenges and unanswered questions," available in PMC Sep. 2, 2011, published in final edited form as: J Membr Biol. 239(1-2):27-34 (2011) (12 pages).

Krauson et al., "Determining the mechanism of membrane permeabilizing peptides: Identification of potent, equilibrium pore-formers," available in PMC Jul. 1, 2013, published in final edited form as: Biochim Biophys Acta. 1818(7):1625-32 (2012) (20 pages).

Rathinakumar et al., "Broad-spectrum Antimicrobial Peptides by Rational Combinatorial Design and High-throughput Screening: The Importance of Interfacial Activity," available in PMC Sep. 8, 2010, published in final edited form as: J Am Chem Soc. 131(22):7609-17 (2009) (23 pages).

He et al., "A Lack of Synergy Between Membrane-permeabilizing Cationic Antimicrobial Peptides and Conventional Antibiotics," available in PMC Jan. 1, 2016, published in final edited form as: Biochim Biophys Acta. 1848(100):8-15 (2015) (21 pages).

Wimley, "Describing the Mechanism of Antimicrobial Peptide Action with the Interfacial Activity Model," available in PMC Oct. 15, 2011, published in final edited form as: ACS Chem Biol. 15(10):905-17 (2010) (21 pages).

Rausch et al., "Beta-Sheet Pore-Forming Peptides Selected from a Rational Combinatorial Library: Mechanism of Pore Formation in Lipid Vesicles and Activity in Biological Membranes," available in PMC Nov. 14, 2008, published in final edited form as: Biochemistry. 46(43):12124-39 (2007) (37 pages).

Starr et al., "Host Cell Interactions are a Significant Barrier to the Clinical Utility of Peptide Antibiotics," available in PMC Jul. 21, 2017, published in final edited form as: ACS Chem Biol. 11(12):3391-99 (2016) (18 pages).

Walkenhorst et al., "pH Dependence of Microbe Sterilization by Cationic Antimicrobial Peptides," Antimicrob Agents Chemother. 57(7) 2013:3312-20 (2013).

Chang et al., "Characterization of antimicrobial peptide activity by electrochemical impedance spectroscopy," available in PMC Oct. 1, 2009, published in final edited form as: Biochim Biophys Acta. 1778(10):2430-36 (2008) (16 pages).

Rathinakumar et al., "High-throughput discovery of broad-spectrum peptide antibiotics," FASEB J. 24(9):3232-38 (2010) (11 pages).

Ladokhin et al., "Leakage of Membrane Vesicle Contents: Determination of Mechanism Using Fluorescence Requenching," Biophys J. 69(5):1964-71 (1995).

Krauson et al., "Synthetic molecular evolution of pore-forming peptides by Iterative combinatorial library screening," available in PMC Apr. 19, 2014, published in final edited form as: ACS Chem Biol. 8(4):823-31 (2013) (18 pages).

Wimley et al., "Interactions between human defensins and lipid bilayers: evidence for formation of multimeric pores," Protein Sci. 3(9):1362-73 (1994).

Starr et al., "Synthetic molecular evolution of host cell-compatible, antimicrobial peptides effective against drug-resistant, biofilm-forming bacteria," Proc Natl Acad Sci U S A. 117(15):8437-48 (2020) (8 pages) (Abstract only).

Chen et al., "Simulation-Guided Rational de Novo Design of a Small Pore-Forming Antimicrobial Peptide," J Am Chem Soc. 141(12):4839-48 (2019) (1 page) (Abstract only).

White et al., "Structure, function, and membrane integration of defensins," Curr Opin Struct Biol. 5(4):521-7 (1995) (1 page) (Abstract only).

Wang et al., "Burkholderia thailandensis outer membrane vesicles exert antimicrobial activity against drug-resistant and competitor microbial species," J Microbiol. 58(7):550-62 (2020) (1 page) (Abstract only).

Lin et al., "Interactions of membrane active peptides with planar supported bilayers: an impedance spectroscopy study," Langmuir. 28(14):6088-96 (2012) (1 page) (Abstract only).

\* cited by examiner

FIG. 4

| SEQ ID No. | NH2-CONH2 | 1 | 2 | 3 | 4 | 5 | 6 | 7 | 8 | 9 | 10 | 11 | 12 | 13 | 14 | 15 | 16 | Peptide Mass |
|---|---|---|---|---|---|---|---|---|---|---|---|---|---|---|---|---|---|---|
| 1 | Tat | G | R | K | K | R | Q | R | R | R | P | P | Q | * | * | * | | 1718 |
| 2 | PENETRATIN | R | Q | I | K | I | W | F | Q | N | R | R | M | K | W | K | K | 2229 |
| | Option | | | | | | | | | | L | | | | | | | |
| 3 | CPP-1 | * | R | K | K | R | W | F | R | R | R | P | K | W | K | K | | 2195 |
| 4 | CPP-2 | G | R | K | K | R | W | F | R | R | R | M | K | W | K | K | | 2286 |
| 5 | CPP-3 | * | R | I | K | R | R | F | R | R | L | R | P | K | W | K | K | 2107 |
| 6 | CPP-4 | R | R | K | K | I | W | F | R | R | L | R | M | K | * | * | * | 1856 |
| 7 | CPP-5 | G | Q | I | K | R | R | F | R | R | L | R | P | K | * | * | * | 1693 |
| 8 | CPP-6 | R | R | K | K | R | R | F | R | R | R | P | P | K | * | * | * | 1819 |
| 9 | CPP-7 | G | R | I | K | R | R | Q | R | R | L | P | P | Q | * | * | * | 1643 |
| 10 | CPP-8 | * | R | I | K | R | R | Q | Q | R | L | R | P | Q | * | * | * | 1617 |

CPP-PNA705

FIG. 32

| MDR | A. baumannii | K. pneumoniae |
|---|---|---|
| DBS1 | 2.6 | 1.2 |
| DBS2 | 4.8 | 1.2 |
| DBS3 | 4.8 | 1.8 |
| DBS4 | 3.2 | 1.3 |
| DBS5 | 1.8 | 1.9 |

SEQUENCE LISTING

<160> NUMBER OF SEQ ID NOS: 42

<210> SEQ ID NO 1
<211> LENGTH: 13
<212> TYPE: PRT
<213> ORGANISM: Artificial Sequence
<220> FEATURE:
<223> OTHER INFORMATION: Synthetic construct

<400> SEQUENCE: 1

Gly Arg Lys Lys Arg Arg Gln Arg Arg Arg Pro Pro Gln
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic construct

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic construct

<400> SEQUENCE: 3

Arg Lys Lys Arg Trp Phe Arg Arg Arg Pro Lys Trp Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic construct

<400> SEQUENCE: 4

Gly Arg Lys Lys Arg Trp Phe Arg Arg Arg Met Lys Trp Lys Lys
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic construct

<400> SEQUENCE: 5

Arg Ile Lys Arg Arg Phe Arg Arg Leu Arg Pro Lys Trp Lys Lys
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: Synthetic construct

<400> SEQUENCE: 6

Arg Arg Lys Lys Ile Trp Phe Arg Arg Leu Arg Met Lys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic construct

<400> SEQUENCE: 7

Gly Gln Ile Lys Arg Arg Phe Arg Arg Leu Arg Pro Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic construct

<400> SEQUENCE: 8

Arg Arg Lys Lys Arg Arg Phe Arg Arg Arg Pro Pro Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic construct

<400> SEQUENCE: 9

Gly Arg Ile Lys Arg Arg Gln Arg Arg Leu Pro Pro Gln

<210> SEQ ID NO 10
<211> LENGTH: 12
<212> TYPE: PRT
<213> ORGANISM: Artificial Sequence
<220> FEATURE:
<223> OTHER INFORMATION: Synthetic construct

<400> SEQUENCE: 10

Arg Ile Lys Arg Arg Gln Gln Arg Leu Arg Pro Gln
1               5                   10

<210> SEQ ID NO 11
<211> LENGTH: 18
<212> TYPE: DNA
<213> ORGANISM: Artificial Sequence
<220> FEATURE:
<223> OTHER INFORMATION: Synthetic construct

<400> SEQUENCE: 11
cctcttacct cagttaca                                                 18

<210> SEQ ID NO 12
<211> LENGTH: 16
<212> TYPE: PRT
<213> ORGANISM: Artificial Sequence
<220> FEATURE:
<223> OTHER INFORMATION: Synthetic construct

<400> SEQUENCE: 12

Arg Asp His Met Val Leu His Glu Tyr Val Asn Ala Ala Gly Ile Thr
1               5                   10                  15

<210> SEQ ID NO 13
<211> LENGTH: 9
<212> TYPE: PRT
<213> ORGANISM: Artificial Sequence
<220> FEATURE:
<223> OTHER INFORMATION: Synthetic construct

<400> SEQUENCE: 13

Arg Arg Arg Arg Arg Arg Arg Arg Arg
1               5

<210> SEQ ID NO 14
<211> LENGTH: 17
<212> TYPE: DNA
<213> ORGANISM: Artificial Sequence
<220> FEATURE:
<223> OTHER INFORMATION: Synthetic construct

<400> SEQUENCE: 14
ccttgcacat gccggag                                                  17

<210> SEQ ID NO 15
<211> LENGTH: 17
<212> TYPE: DNA
<213> ORGANISM: Artificial Sequence
<220> FEATURE:
<223> OTHER INFORMATION: Synthetic construct

<400> SEQUENCE: 15
acagagcctc gcctttg                                                  17

<210> SEQ ID NO 16

```
<211> LENGTH: 25
<212> TYPE: DNA
<213> ORGANISM: Artificial Sequence
<220> FEATURE:
<223> OTHER INFORMATION: Synthetic construct

<400> SEQUENCE: 16
acagtgataa tttctgggtt aaggc                                          25

<210> SEQ ID NO 17
<211> LENGTH: 21
<212> TYPE: DNA
<213> ORGANISM: Artificial Sequence
<220> FEATURE:
<223> OTHER INFORMATION: Synthetic construct

<400> SEQUENCE: 17
tcaatcagag tgcttttggc g                                              21

<210> SEQ ID NO 18
<211> LENGTH: 23
<212> TYPE: DNA
<213> ORGANISM: Artificial Sequence
<220> FEATURE:
<223> OTHER INFORMATION: Synthetic construct

<400> SEQUENCE: 18
ttacgatccc ttcaggatta caa                                            23

<210> SEQ ID NO 19
<211> LENGTH: 15
<212> TYPE: PRT
<213> ORGANISM: Artificial Sequence
<220> FEATURE:
<223> OTHER INFORMATION: Synthetic construct

<400> SEQUENCE: 19

Arg Arg Gly Trp Ala Leu Arg Pro Val Leu Ala Phe Gly Arg Arg
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic construct

<400> SEQUENCE: 20

Arg Arg Gly Trp Ala Arg Arg Leu Ala Ala Tyr Gly Arg Arg
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic construct

<400> SEQUENCE: 21

Arg Arg Gly Trp Ala Phe Arg Arg Ala Leu Ala Tyr Gly Arg Arg
1               5                   10                  15

<210> SEQ ID NO 22
<211> LENGTH: 15
<212> TYPE: PRT
<213> ORGANISM: Artificial Sequence
<220> FEATURE:
```

```
<223> OTHER INFORMATION: Synthetic construct

<400> SEQUENCE: 22

Arg Arg Gly Trp Ala Arg Arg Leu Phe Phe Ala Tyr Gly Arg Arg
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic construct

<400> SEQUENCE: 23

Arg Arg Gly Trp Ala Ala Arg Leu Phe Ala Ala Phe Gly Arg Arg
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic construct

<400> SEQUENCE: 24

Arg Arg Gly Trp Ala Arg Arg Leu Phe Ala Ala Phe Gly Arg Arg
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic construct

<400> SEQUENCE: 25

Arg Arg Gly Trp Ala Arg Arg Leu Val Phe Ala Phe Gly Arg Arg
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: Synthetic construct

<400> SEQUENCE: 26

Arg Arg Gly Trp Ala Arg Ala Leu Ala Phe Ala Phe Gly Arg
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic construct

<400> SEQUENCE: 27

Arg Arg Trp Ala Arg Arg Leu Phe Phe Ala Tyr Arg Arg
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic construct
```

```
<400> SEQUENCE: 28

Arg Arg Trp Asn Leu Ala Leu Thr Leu Thr Tyr Tyr Arg Arg
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Synthetic construct

<400> SEQUENCE: 29

Arg Arg Gly Trp Ala Leu Arg Leu Val Leu Ala Tyr Gly Arg Arg
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic construct

<400> SEQUENCE: 30

Arg Arg Gly Trp Ala Arg Arg Leu Ala Phe Ala Phe Gly Arg Arg
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (4)..(4)
<223> OTHER INFORMATION: Xaa is D-Trp
<220> FEATURE:
<221> NAME/KEY: MISC_FEATURE
<222> LOCATION: (5)..(5)
<223> OTHER INFORMATION: Xaa is D-Ala
<220> FEATURE:
<221> NAME/KEY: MISC_FEATURE
<222> LOCATION: (6)..(7)
<223> OTHER INFORMATION: Xaa is D-Arg
<220> FEATURE:
<221> NAME/KEY: MISC_FEATURE
<222> LOCATION: (8)..(8)
<223> OTHER INFORMATION: Xaa is D-Leu
<220> FEATURE:
<221> NAME/KEY: MISC_FEATURE
<222> LOCATION: (9)..(9)
<223> OTHER INFORMATION: Xaa is D-Ala
<220> FEATURE:
<221> NAME/KEY: MISC_FEATURE
<222> LOCATION: (10)..(10)
<223> OTHER INFORMATION: Xaa is D-Phe
<220> FEATURE:
<221> NAME/KEY: MISC_FEATURE
<222> LOCATION: (11)..(11)
<223> OTHER INFORMATION: Xaa is D-Ala
<220> FEATURE:
<221> NAME/KEY: MISC_FEATURE
<222> LOCATION: (12)..(12)
<223> OTHER INFORMATION: Xaa is D-Phe
<220> FEATURE:
<221> NAME/KEY: MISC_FEATURE
<222> LOCATION: (14)..(15)
<223> OTHER INFORMATION: Xaa is D-Arg
```

```
<400> SEQUENCE: 31

Xaa Xaa Gly Xaa Xaa Xaa Xaa Xaa Xaa Xaa Xaa Gly Xaa Xaa
1               5                   10                  15

<210> SEQ ID NO 32
<211> LENGTH: 17
<212> TYPE: PRT
<213> ORGANISM: Artificial Sequence
<220> FEATURE:
<223> OTHER INFORMATION: Synthetic construct

<400> SEQUENCE: 32

Arg Arg Gly Trp Ala Arg Arg Leu Arg Leu Ala Phe Ala Phe Gly Arg
1               5                   10                  15

Arg

<210> SEQ ID NO 33
<211> LENGTH: 17
<212> TYPE: PRT
<213> ORGANISM: Artificial Sequence
<220> FEATURE:
<223> OTHER INFORMATION: Synthetic construct

<400> SEQUENCE: 33

Arg Arg Gly Trp Ala Arg Arg Leu Ala Phe Ala Phe Ala Phe Gly Arg
1               5                   10                  15

Arg

<210> SEQ ID NO 34
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: Xaa is D-Lys
<220> FEATURE:
<221> NAME/KEY: MISC_FEATURE
<222> LOCATION: (4)..(4)
<223> OTHER INFORMATION: Xaa is D-Trp
<220> FEATURE:
<221> NAME/KEY: MISC_FEATURE
<222> LOCATION: (5)..(5)
<223> OTHER INFORMATION: Xaa is D-Ala
<220> FEATURE:
<221> NAME/KEY: MISC_FEATURE
<222> LOCATION: (6)..(7)
<223> OTHER INFORMATION: Xaa is D-Lys
<220> FEATURE:
<221> NAME/KEY: MISC_FEATURE
<222> LOCATION: (8)..(8)
<223> OTHER INFORMATION: Xaa is D-Leu
<220> FEATURE:
<221> NAME/KEY: MISC_FEATURE
<222> LOCATION: (9)..(9)
<223> OTHER INFORMATION: Xaa is D-Ala
<220> FEATURE:
<221> NAME/KEY: MISC_FEATURE
<222> LOCATION: (10)..(10)
<223> OTHER INFORMATION: Xaa is D-Phe
<220> FEATURE:
<221> NAME/KEY: MISC_FEATURE
<222> LOCATION: (11)..(11)
<223> OTHER INFORMATION: Xaa is D-Ala
<220> FEATURE:
<221> NAME/KEY: MISC_FEATURE
<222> LOCATION: (12)..(12)
<223> OTHER INFORMATION: Xaa is D-Phe
```

-continued

```
<220> FEATURE:
<221> NAME/KEY: MISC_FEATURE
<222> LOCATION: (14)..(15)
<223> OTHER INFORMATION: Xaa is D-Lys

<400> SEQUENCE: 34

Xaa Xaa Gly Xaa Xaa Xaa Xaa Xaa Xaa Xaa Xaa Xaa Gly Xaa Xaa
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (4)..(4)
<223> OTHER INFORMATION: Xaa is D-Trp
<220> FEATURE:
<221> NAME/KEY: MISC_FEATURE
<222> LOCATION: (5)..(5)
<223> OTHER INFORMATION: Xaa is D-Ala
<220> FEATURE:
<221> NAME/KEY: MISC_FEATURE
<222> LOCATION: (6)..(6)
<223> OTHER INFORMATION: Xaa is D-Phe
<220> FEATURE:
<221> NAME/KEY: MISC_FEATURE
<222> LOCATION: (7)..(8)
<223> OTHER INFORMATION: Xaa is D-Arg
<220> FEATURE:
<221> NAME/KEY: MISC_FEATURE
<222> LOCATION: (9)..(9)
<223> OTHER INFORMATION: Xaa is D-Ala
<220> FEATURE:
<221> NAME/KEY: MISC_FEATURE
<222> LOCATION: (10)..(10)
<223> OTHER INFORMATION: Xaa is D-Leu
<220> FEATURE:
<221> NAME/KEY: MISC_FEATURE
<222> LOCATION: (11)..(11)
<223> OTHER INFORMATION: Xaa is D-Ala
<220> FEATURE:
<221> NAME/KEY: MISC_FEATURE
<222> LOCATION: (12)..(12)
<223> OTHER INFORMATION: Xaa is D-Tyr
<220> FEATURE:
<221> NAME/KEY: MISC_FEATURE
<222> LOCATION: (14)..(15)
<223> OTHER INFORMATION: Xaa is D-Arg

<400> SEQUENCE: 35

Xaa Xaa Gly Xaa Xaa Xaa Xaa Xaa Xaa Xaa Xaa Xaa Gly Xaa Xaa
1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (4)..(4)
<223> OTHER INFORMATION: Xaa is D-Trp
<220> FEATURE:
```

```
<221> NAME/KEY: MISC_FEATURE
<222> LOCATION: (5)..(5)
<223> OTHER INFORMATION: Xaa is D-Ala
<220> FEATURE:
<221> NAME/KEY: MISC_FEATURE
<222> LOCATION: (6)..(7)
<223> OTHER INFORMATION: Xaa is D-Arg
<220> FEATURE:
<221> NAME/KEY: MISC_FEATURE
<222> LOCATION: (8)..(8)
<223> OTHER INFORMATION: Xaa is D-Leu
<220> FEATURE:
<221> NAME/KEY: MISC_FEATURE
<222> LOCATION: (9)..(10)
<223> OTHER INFORMATION: Xaa is D-Phe
<220> FEATURE:
<221> NAME/KEY: MISC_FEATURE
<222> LOCATION: (11)..(11)
<223> OTHER INFORMATION: Xaa is D-Ala
<220> FEATURE:
<221> NAME/KEY: MISC_FEATURE
<222> LOCATION: (13)..(14)
<223> OTHER INFORMATION: Xaa is D-Arg

<400> SEQUENCE: 36

Xaa Xaa Gly Xaa Xaa Xaa Xaa Xaa Xaa Xaa Xaa Gly Xaa Xaa
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (9)..(9)
<223> OTHER INFORMATION: Xaa is D-Phe
<220> FEATURE:
<221> NAME/KEY: MISC_FEATURE
<222> LOCATION: (10)..(10)
<223> OTHER INFORMATION: Xaa is D-Ala
<220> FEATURE:
<221> NAME/KEY: MISC_FEATURE
<222> LOCATION: (11)..(11)
<223> OTHER INFORMATION: Xaa is D-Phe
<220> FEATURE:
<221> NAME/KEY: MISC_FEATURE
<222> LOCATION: (12)..(13)
<223> OTHER INFORMATION: Xaa is D-Arg

<400> SEQUENCE: 37
```

```
Xaa Xaa Xaa Xaa Xaa Xaa Xaa Xaa Xaa Xaa Xaa Xaa
1               5                   10
```

<210> SEQ ID NO 38
<211> LENGTH: 13
<212> TYPE: PRT
<213> ORGANISM: Artificial Sequence
<220> FEATURE:
<223> OTHER INFORMATION: Synthetic construct

<400> SEQUENCE: 38

```
Arg Arg Trp Ala Arg Arg Leu Ala Phe Ala Phe Arg Arg
1               5                   10
```

<210> SEQ ID NO 39
<211> LENGTH: 15
<212> TYPE: PRT
<213> ORGANISM: Artificial Sequence
<220> FEATURE:
<223> OTHER INFORMATION: Synthetic construct

<400> SEQUENCE: 39

```
Lys Lys Gly Trp Ala Lys Lys Leu Ala Phe Ala Phe Gly Lys Lys
1               5                   10                  15
```

<210> SEQ ID NO 40
<211> LENGTH: 12
<212> TYPE: PRT
<213> ORGANISM: Artificial Sequence
<220> FEATURE:
<223> OTHER INFORMATION: Synthetic construct

<400> SEQUENCE: 40

```
Arg Arg Gly Trp Ala Leu Arg Leu Val Leu Ala Tyr
1               5                   10
```

<210> SEQ ID NO 41
<211> LENGTH: 12
<212> TYPE: PRT
<213> ORGANISM: Artificial Sequence
<220> FEATURE:
<223> OTHER INFORMATION: Synthetic construct

<400> SEQUENCE: 41

```
Arg Gly Trp Ala Arg Arg Arg Phe Phe Ala Ser Gly
1               5                   10
```

<210> SEQ ID NO 42
<211> LENGTH: 13
<212> TYPE: PRT
<213> ORGANISM: Artificial Sequence
<220> FEATURE:
<223> OTHER INFORMATION: Synthetic construct

<400> SEQUENCE: 42

```
Arg Arg Gly Trp Ala Arg Arg Leu Ala Phe Gly Arg Arg
1               5                   10
```

US 11,266,743 B2

PEPTIDE COMPOSITIONS AND METHODS OF USE THEREOF

STATEMENT REGARDING FEDERALLY SPONSORED RESEARCH

This invention was made with government support under Grant Nos. RO1GM111824, RO1 GM60000, and R21AI119104, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created Apr. 23, 2020, is named 07005-020003_Sequence_Listing_04.23.20_ST25 and is 13,297 bytes in size.

BACKGROUND

Cellular membrane penetrating peptides could have utility in a variety of biotechnological and clinical applications due to their ability to breach the barrier imposed by lipid bilayers. Indeed, while efficient methods exist to deliver oligonucleotides to cells, most other types of macromolecules are more difficult to deliver. Useful macromolecules include proteins, such as antibodies, nanobodies, inhibitors, and enzymes, as well as peptides, polysaccharides, imaging agents, synthetic oligonucleotides, and more. These macromolecules can be directed to existing cellular uptake mechanisms, but in the absence of endosome permeabilization or disruption, they often get trapped within the classical pathways that lead to their lysosomal degradation or recycling without significant entry into the cytosol and subsequent ligand binding.

Peptides as in vitro cargo-delivery and in vivo therapeutic agents are generating increasing interest. While there are currently 60+ FDA approved peptide drugs on the market with another 140+ in clinical trials and 500+ in pre-clinical development the vast majority of these have extracellular targets as cell membrane represents a barrier to intracellular delivery. While known cell-penetrating peptides (CPPs) have for many years shown promise as delivery vehicles capable of transporting some cell impermeant cargo to their cytosolic or nuclear ligands, there remains a need to identify sequences with lower effective treatment concentrations, increased cargo capacity, decreased cytotoxicity, and alternative mechanisms of action.

The administration of peptide drugs targeting extracellular ligands requires overcoming high elimination rates, uptake by off-target cells, and the potential to create an immune response. Those targeting intracellular ligands must also efficiently enter the cell. While polymer conjugation, micro-reservoir delivery systems, and cell type specific targeting moieties exist and address some of these pharmacokinetic issues, effective strategies and new modalities for efficient intracellular delivery of macromolecules are still needed to advance the field.

The emerging consensus on the efficiency and mechanism of action of CPPs, such as tat and penetratin, is that direct translocation and endocytosis-dependent delivery occur in parallel, but at rates that differ dramatically based on CPP sequence, CPP concentration, cell type, cargo, buffer system, and temperature among other experimental variables. Efficient delivery of cargo often requires high CPP concentration that leads to direct translocation across the membrane, but simultaneously can also cause membrane disruption and toxicity. Cell penetrating peptides have been studied for decades toward solving the problem of intracellular delivery. There are examples of successful delivery of some cargo types, especially covalently attached fluorescent molecules and oligonucleotide cargoes noncovalently complexed with CPPs. However other classes of cargoes, including proteins, peptides and peptide nucleic acids, remain difficult to deliver routinely and efficiently to cells. Thus, there exists a need for peptides that act as CPPs for therapeutic and diagnostic purposes.

With rapidly increasing emergence of antibiotic-resistant bacteria, the development of novel antibiotics is extremely important to the medical field. The mechanism of action of antimicrobial peptides (AMPS), plasma membrane destabilization, makes them less likely to elicit resistant phenotypes. Gram-negative bacteria are notoriously difficult to treat with traditional small molecule antibiotics. Thus, there exists a need to develop novel peptides that are effective against difficult to treat microbes, in particular, Gram-negative pathogens.

SUMMARY OF THE INVENTION

A first aspect of the invention features polypeptides having at least 85% sequence identity to the sequence of any one of SEQ ID NOS: 1-10, in which the polypeptide does not have the sequence of SEQ ID NO: 1 or 2 (e.g., the polypeptide has at least 90%, 95%, 97%, or 100% sequence identity to any one of SEQ ID NOS: 3-10). In particular the polypeptides are cell penetrating peptides, such as polypeptides exhibiting a rate of cellular internalization of at least 200% (e.g., 200%, 250%, 300%, 350%, 400%, 450%, or more) relative to a Tat peptide (SEQ ID NO: 1).

The cell penetrating polypeptide may also have one or more D-amino acids (e.g., D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, and D-VAL). The cell penetrating polypeptide can also have one or more derivatized amino acids (e.g., N-imbenzylhistidine, 4-hydroxyproline, 5-hydroxylysine, 3-methylhistidine, homoserine, and ornithine). The featured cell penetrating polypeptides may also have a chemical moiety (e.g., amine hydrochloride, p-toluene sulfonyl, carbobenzoxy, t-butyloxycarbonyl, chloroacetyl, formyl, carboxyl, methyl ester, ethyl ester, hydrazide, O-acyl, and O-alkyl). The cell penetrating polypeptides may be 10-16 amino acids long (e.g., 10, 11, 12, 13, 14, 15, or 16 amino acids).

A second aspect of the invention are conjugates of the cell penetrating polypeptides of the invention joined to a compound. The conjugated cell penetrating polypeptides may be joined to a compound either directly, or through a linker (e.g., a small molecule, a polymer, an amino acid, or a peptide). The cell penetrating polypeptide may be joined to the compound through a covalent bond. The compound joined to the cell penetrating polypeptide may enhance the stability, immunogenicity, or detection of the polypeptide. The compound may also facilitate in the purification of the cell penetrating peptide, and it may be a second polypeptide (e.g., a FLAG tag). The compound may be a therapeutic agent (e.g., an immunotherapy agent, a cytotoxic agent, a growth inhibitory agent, a radiation therapy agent, an anti-cancer agent, or an anti-angiogenic agent). In particular, the therapeutic agent may be an anti-cancer agent (e.g., abiraterone acetate, methotrexate, paclitaxel, albumin, doxorubicin, bleomycin, vinblastine, dacarbazine, vincristine sulfate, etoposide phosphate, prednisone, cyclophosphamide, brentuximab vedotin, cytarabine, daunorubicin, ado-trastuzumab emtansine, afatinib dimaleate, everolimus, netupitant, palonosetron, imiquimod, alectinib, alemtuzumab, melphalan, pemetrexed, chlorambucil, aminolevulinic acid, aprepitant, pamidronate, anastrozole, exemestane, nelarabine, arsenic trioxide, ofatumumab, asparaginase Erwinia chrysanthemi, bevacizumab, axitinib, azacitidine, carmustine, belinostat, bendamustine, cisplatin, bexarotene, tositumomab, iodine 131I tositumomab, bicalutamide, blinatumomab, bortezomib, bosutinib, busulfan, cabazitaxel, cabozantinib-S-malate, irinotecan, capecitabine, fluorouracil, carboplatin, carfilzomib, lomustine, ceritinib, recombinant HPV bivalent vaccine, cetuxima, clofarabine, cobimetinib, dactinomycin, crizotinib, ifosfamide, ramucirumab, liposome, dabrafenib, decitabine, daratumumab, dasatinib, degarelix, denileukin diftitox, denosumab, dexamethasone, dexrazoxane, dinutuximab, docetaxel, rasburicase, epirubicin, elotuzumab, eltrombopag olamine, enzalutamide, eribulin mesylate, vismodegib, erlotinib, etoposide, raloxifene, toremifene, panobinostat, fulvestrant, letrozole, filgrastim, fludarabine phosphate, flutamide, pralatrexate, recombinant HPV quadrivalent vaccine, recombinant HPV nonavalent vaccine, obinutuzumab, gefitinib, gemcitabine, gemcitabine-cisplatin, gemcitabine-oxaliplatin, gemtuzumab ozogamicin, imatinib mesylate, glucarpidase, goserelin acetate, trastuzumab, HPV bivalent vaccine, topotecan, palbociclib, ponatinib, idarubicin, idelalisib, ifosfamidum, IL-2, ibrutinib, talimogene laherparepvec, recombinant interferon alpha-2b, ipilimumab, romidepsin, ixabepilone, ixazomib citrate, ruxolitinib phosphate, palifermin, pembrolizumab, lanreotide acetate, lapatinib ditosylate, lenalidomide, lenvatinib mesylate, leucovorin calcium, leuprolide acetate, trifluridine, tipiracil, olaparib, procarbazine, mechlorethamine, megestrol acetate, trametinib, mercaptopurine, mesna, temozolomide, mitomycin C, mitoxantrone, plerixafor, vinorelbine tartrate, sorafenib tosylate, nivolumab, tamoxifen citrate, romiplostim, sonidegib, omacetaxine mepesuccinate, pegaspargase, ondansetron, osimertinib, oxaliplatin, paclitaxel albumin-stabilized nanoparticle, panitumumab, pazopanib, peginterferon alpha-2b, pertuzumab, pomalidomide, necitumumab, sipuleucel-T, 223Ra dichloride, recombinant human papillomavirus, regorafenib, rituximab, rolapitant, siltuximab, sunitinib malate, thalidomide, thioguanine, nilotinib, temsirolimus, thiotepa, trabectedin, arsenic trioxide, uridine triacetate, vandetanib, vorinostat, ziv-aflibercept, vemurafenib, ibritumomab tiuxetan, zoledronic acid, and idelalisib).

The cell penetrating polypeptide may also be joined to a compound that is a therapeutic agent (e.g., Human growth hormone, Erythropoietin (EPO), Ob gene translation product (leptin), Adenosine deaminase, purine nucleoside, phosphorylase, CD-4, Factor VIII, Factor IX, α1-antitrypsin, LDL receptor protein, Intrinsic factor, albumin, b-glucosidase (glucocerebrosidase), CF transmembrane conductance regulator, tissue plasminogen activator (tPA), urokinase, streptokinase, antithrombin III, apolipoprotein (e.g., APO B48, A1), Low Density lipoprotein receptor, vascular endothelial growth factor (VEGF), Calcitonin, parathyroid hormone (PTH), PTH-like hormone, a Adenosine deaminase, a Phenylalanine hydroxylase, a von Willebrand Factor, a Tumor Necrosis Factor (TNF), a cytokine, a anti-neoplastic agent (e.g., vincristine, doxorubicin, tamoxifen, or methotrexate), interleukins (ILs), interferons (INFs), p53, anti-BRCAs, anti-VEGF (bevacizumab), anti-Epidermal Growth Factor (EGF), oncogene anti-sense RNA, an antibody (e.g., Rituximab, Daclizumab, Basiliximab, Palivizumab, Infliximab, Trastuzumab, Gemtuzumab ozogamicin, Alemtuzumab, Ibritumomab tiuxetan, Adalimumab, Omalizumab, Tositumomab-I-131, Efalizumab, Cetuximab, Bevacizumab, Natalizumab, Tocilizumab, Panitumumab, Ranibizumab, Eculizumab, Certolizumab pegol, Golimumab, Canakinumab, Ustekinumab, Ofatumumab, Denosumab, Motavizumab, Raxibacumab, Belimumab, Ipilimumab, Brentuximab Vedotin, Pertuzumab, Ado-trastuzumab emtansine, or Obinutuzumab), checkpoint inhibitors (e.g., nivolumab, pidilizumab/CT-011, pembrolizumab, ipilimumab, or tremelimumab), VEGF, endothelin, Ciliary Neurotrophic Factor (CNTF), Brain Derived Neurite Factor (BDNF), nerve growth factor (NGF), tyrosine hydroxylase, bone morphogenic proteins (BMP), lactase, an epidermal growth factor, transforming growth factors, granulocyte-colony stimulating factors, fibroblast growth factors, insulin-like growth factors, an antithrombin, hirudins, antidiuretic hormone (ADH), selective serotonin reuptake inhibitors, anti-psychotic bio-substances, an endorphin, an estrogen, an androgen, a mineralocorticoid, a glucocorticoid, an anabolic steroid, a thyroid hormone, a thyroglobulin, Dystrophin, an antimicrobial polypeptide, a lipid binding protein (LBP), L-asparaginase, pepsin, trypsin, chymotrypsin, cholecystokinin, sucrase, carboxypeptidase, catalase, uricase, elastase, thrombopoietin (TPO), adenosine deaminase, porphobilinogen deaminase, an enzyme catalyzes a transformation at a genetic block point (e.g., glutaryl CoA dehydrogenase), cystathionine B-synthase, specific copper transporting ATPase's, β-globin, α-globin, Sonic hedgehog gene products, thyroid hormone, VEGF trap (e.g., a soluble decoy receptor, such as VEGF-trapparental, VEGF-TrapΔB1, VEGF-TrapΔB2, and VEGF-TrapR1R2, e.g., aflibercept), a soluble form of VEGF receptors (e.g., soluble VEGFR-1 or NRP-1), platelet factor-4, prolactin, SPARC, a VEGF inhibitory antibodie (e.g., bevacizumab or ranibizumab), a TNFα inhibitor (adalimumab, etanercept, infliximab, golimumab, certolizumab), interleukin-6 (IL6) receptor inhibitors (e.g., tocilizumab), IL1 receptor inhibitors (e.g., anakinra), an abatacept, rituximab, mesalazine, prednisone, azathioprine, methotrexate, aldosterone, cortisol, alpha-L iduronidase, sphingomyelin phosphodiesterase1 (SMPD1), NPC1 protein, NPC2 protein, beta-hexosaminidase A, alpha galactosidase, galactosylceramidase, galactokinase, galactose-1-phosphate uridyltransferase, a branched-chain alpha-keto acid dehydrogenase complex enzyme, phenylalanine hydroxylase, glycogen synthase (GYS2), glucose-6-phosphatase (G6PC), acid alpha-glucosidase (GAA), glycogen debranching enzyme (AGL), glycogen branching enzyme (GBE1), muscle glycogen phosphorylase (myophosphorylase) (PYGM), liver glycogen phosphorylase (PYGL), muscle phosphoglycerate mutase (PGAM2), muscle phosphofructokinase (PKFM), glycogen phosphorylase kinase B (e.g., PHKA2, PHKB, PHKG2, or PHKA1), enolase 3 (ENO3), muscle lactate dehydrogenase (LDHA), glucose transporter 2 (GLUT2), aldolase A (ALDOA), β enolase (ENO3), Glycogenin-1 (GYG1), NADH dehydrogenase, thiamine-diphosphate kinase, thiamine triphosphate, pyruvate dehydrogenase, an ATP synthase, thymidine phosphorylase (TYMP), NADH dehydrogenase, Frataxin (FXN), a protein encoded by PEX1, PEX2, PEX3, PEX5, PEX6, PEX10, PEX12, PEX13, PEX14, PEX16, PEX19, or PEX26, a protein encoded by ABCD1, Wilson disease protein (ATP7B), Human hemochromatosis protein (HFE), methylmalonyl CoA mutase, methylmalonyl CoA epimerase, adenosylcobalamin, propionyl-CoA carboxylase, ornithine transcarbamylase, argininosuccinate lyase, argininosuccinate synthase 1, citrin, carbamoyl phosphate synthase 1, N-acetylglutamate synthase, and ornithine translocase).

The cell penetrating peptide may be joined to a nucleic acid (e.g., a polynucleic acid). The polynucleic acid may have a modified phosphate backbone (e.g., phosphorothioate, phosphorodithioate, an amide, thioamide, sulfonamide, or sulfonamide). In particular, the backbone modification may be a peptide bond.

A third aspect of the invention features a polynucleotide encoding the cell penetrating polypeptide, or polypeptide conjugate.

A fourth aspect of the invention features a vector containing the polynucleotide encoding the polypeptide.

A fifth aspect of the invention features a composition comprising the cell penetrating polypeptide, the cell penetrating polypeptide conjugate, the polynucleotide encoding the polypeptide, or the vector of the invention. The composition may also comprise a pharmaceutically acceptable carrier, excipient, or diluent. The composition may further comprise a therapeutic agent. In particular, the therapeutic agent is an immunotherapy agent or an anti-cancer agent.

A sixth aspect of the invention features a method of delivering a compound to a target cell by contacting the cell with the polypeptide conjugate.

A seventh aspect of the invention is a method of diagnosing a medical condition in a subject by administering the polypeptide conjugate and detecting the compound.

An eighth aspect of the invention is a method of treating a medical condition in a subject by administering the polypeptide conjugate to a subject. The method of diagnosing or treating a patient, in which the polypeptide conjugate is administered to the subject prior to, with, or after the administration of an additional therapeutic agent. The polypeptide conjugate may be administered to a subject in an amount and/or for a duration sufficient to treat or diagnose the subject. In particular, the medical condition is cancer, and the subject is a human. The composition administered to the subject that comprises the compound, in which the compound is delivered to a target cell (e.g., a cancer cell). In particular, the cancer may be leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, throat cancer, acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, hodgkin lymphoma, hypopharyngeal cancer, islet cell tumors, pancreatic neuroendocrine tumors, wilms tumor and other childhood kidney tumors, langerhans cell histiocytosis, small cell lung cancer, cutaneous T cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, retinoblastoma, rhabdomyosarcoma, salivary gland cancer, kaposi sarcoma, rhabdomyosarcoma, sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia.

The method of administering a composition to treat or diagnose a medical condition (e.g., wherein the medical condition is selected from the group consisting of diabetes, altered glycemic states, skeletal growth retardation, anemia, obesity, Immunodeficiency (e.g., AIDS), hemophilia A, hemophilia B, emphysema, hypercholesterolemia, pernicious anemia, hypoalbuminemia, Gaucher's disease, cystic fibrosis, cardiovascular disease, calcium mineral diseases, severe combined immunodeficiency (SCID), phenylketonuria, von Willebrand's disease, cancers, cancer suppression, peripheral vascular disease, neurodegenerative states, a post neural trauma condition, retarded fracture healing, lactose insufficiency, wound healing, thrombosis, hypercoagulability, diabetes insipidus, a psychiatric disorder, pain control, an endocrineopathy, hypothyroidism, muscular dystrophy, an infection (e.g., a bacterial, fungal, or viral infection), shock, sepsis, leukemia, a disorder of digestive, a disorder of the pancreas, oxidative stress, a neurodegenerative disorder, hypouricasemia, gout, Ehlers Danlos syndrome, thrombocytopenia, SCID/ADA deficiency, porphyria, an inborn error of carboxylic and amino acid metabolism, (e.g., glutaric acidemia), homocystinuria, Wilson's disease, Menke's disease, thalassemia, sickle cell anemia, baldness, Hashimoto's thyroiditis, wet age-related macular degeneration or retinal dystrophy, osteoarthritis, rheumatoid arthritis, inflammatory bowel disease, Crohn's disease, ulcerative colitis, Addison's disease, Hurler syndrome, Niemann-Pick disease, Tay-Sachs disease, Fabry disease, Krabbe disease, galactosemia, maple syrup urine disease, phenylketonuria, a glycogen storage disease (GSDS), a mitochondrial disorder, Friedrich's ataxia, a peroxisomal disorder, a metal metabolism disorder, and an organic academia).

The composition of the invention to treat a medical condition in a subject, in which the medical condition is cancer (e.g., leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, throat cancer, acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, hodgkin lymphoma, hypopharyngeal cancer, islet cell tumors, pancreatic neuroendocrine tumors, wilms tumor and other childhood kidney tumors, langerhans cell histiocytosis, small cell lung cancer, cutaneous T cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, retinoblastoma, rhabdomyosarcoma, salivary gland cancer, kaposi sarcoma, rhabdomyosarcoma, sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia), in particular where the subject is a human.

A ninth aspect of the invention features a kit comprising the composition of the invention.

A tenth aspect of the invention features polypeptides having at least 85% sequence identity to the sequence of any one of SEQ ID NOS: 19-42, (e.g., the polypeptide has at least 90%, 95%, 97%, or 100%). In particular, the polypeptide having the sequence of SEQ ID NO: 37. The polypeptides are antimicrobial peptides, such as polypeptides exhibiting a the ability to disrupt the cellular membrane of a microbial pathogen (e.g., *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *B. cepacia*, *Citrobacter freundii*, *Citrobacter koseri*, *Clostridium clostridioforme*, *Clostridium perfringens*, *C. sordellii*, *Enterobacter aerogenes*, *Enterobacter cloacae*, *Enterococcus faecalis*, *Enterococcus* spp. (vancomycin susceptible and resistant isolates), *Escherichia coli* (including ESBL and KPC producing isolates), *Eubacterium lentum*, *Fusobacterium* spp., *Haemophilus influenzae* (including beta-lactamase positive isolates), *Haemophilus parainfluenzae*, *Klebsiella pneumoniae* (including ESBL and KPC producing isolates), *Klebsiella oxytoca* (including ESBL and KPC producing isolates), *Legionella* pneumophilia, *Moraxella catarrhalis*, *Morganella morganii*, *Mycoplasma* spp., *Peptostreptococcus* spp., *Porphyromonas saccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus* (methicillin susceptible and resistant isolates), *Staphylococcus epidermidis* (methicillin susceptible and resistant isolates), *Stenotrophomonas maltophilia*, *Streptococcus agalactiae*, *Streptococcus constellatus*, *Streptococcus pneumoniae* (penicillin susceptible and resistant isolates), *Streptococcus pyogenes*, or *Streptococcus pyogenes*) and/or a fungal pathogen (e.g., from phylum Ascomycota (e.g., *Ajellomyces* spp., *Alternaria* spp., *Aschersonia* spp., *Aspergillus* spp., *Arthroderma* spp., *Ascochyta* spp., *Bipolaris* spp., *Blastomyces* spp., *Botryotinia* spp., *Chaetomium* spp., *Cladosporium* spp., *Coccidioides* spp., *Curvularia* spp., *Emericella* spp., *Emmonsia* spp., *Epicoccum* spp., *Exophiala* spp., *Fusarium* spp., *Geomyces* spp., *Geotrichum* spp., *Gibberella* spp., *Histoplasma* spp., *Magnaporthe* spp., *Metarhizium* spp., *Monascus* spp., *Mycospaerella* spp., *Nectria* spp., *Neosartorya* spp., *Neurospora* spp., *Paecilomyces* spp., *Paracoccidioides* spp., *Penicillium* spp., *Phaeosphaeria* spp., *Phialemonium* spp., *Podospora* spp., *Pyrenophora* spp., *Sclerotinia* spp., *Scopulariopsis* spp., *Sporothrix* spp., *Stachybotrys* spp., *Stemphylium* spp., *Talaromyces* spp., *Trichophyton* spp., *Trichothecium* spp., *Tricoderma* spp., *Tuber* spp., *Uncinocarpus* spp., or *Verticillium* spp.), phylum Basidomycota (e.g., *Moniliophthora* spp., *Sporobolomyces* spp., *Trichosporon* spp., *Ustilago* spp., *Cryptococcus* spp. or *Rhodotorula* spp.), phylum Chytridiomycota, phylum Zygomycota (e.g., *Absidia* spp., *Amylomyces* spp, *Pilaira* spp., *Rhizomucor* spp., *Rhizopus* spp., or *Zygomycetes* spp.), and phylum Oomycota in the Stramenopila kingdom).

The antimicrobial peptides may also have one or more D-amino acids (e.g., D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, and D-VAL). The antimicrobial peptide can also have one or more derivatized amino acids (e.g., N-imbenzylhistidine, 4-hydroxyproline, 5-hydroxylysine, 3-methylhistidine, homoserine, and ornithine). The featured cell penetrating polypeptides may also have a chemical moiety (e.g., amine hydrochloride, p-toluene sulfonyl, carbobenzoxy, t-butyloxycarbonyl, chloroacetyl, formyl, carboxyl, methyl ester, ethyl ester, hydrazide, O-acyl, and O-alkyl). The cell penetrating polypeptides may be 10-20 amino acids long (e.g., 10, 11, 12, 13, 14, 15, 16, 17, 18, 19, or 20 amino acids).

An eleventh aspect of the invention features a polynucleotide encoding the antimicrobial peptide.

A twelfth aspect of the invention features a vector containing the polynucleotide encoding the polypeptide.

A thirteenth aspect of the invention features a composition comprising the antimicrobial peptide, the polynucleotide encoding the polypeptide, or the vector of the invention. The composition may also comprise a pharmaceutically acceptable carrier, excipient, or diluent. The composition may further comprise a therapeutic agent. In particular, the therapeutic agent is an antimicrobial agent, such as an antifungal agent (e.g., a triazole, such as fluconazole, albaconazole, efinaconazole, epoxiconazole, isavuconazole, itraconazole, posaconazole, propiconazole, ravuconazole, terconazole, and voriconazole; an imidazole, such as bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, and tioconazole; and a thiazole, such as abafungin), a polyene (e.g., amphotericin B, candicidin, filipin, hamycin, natamycin, nystatin, and rimocidin), an allylamine (e.g., amorolfin, butenafine, naftifine, and terbinafine), an echinocandin (e.g., anidulafungin, biafungin (e.g., CD101), caspofungin, and micafungin), lanosterol demethylase inhibitors (e.g., VT-1161) and other antifungal agents, including, but not limited to, benzoic acid, ciclopirox olamine, enfumafungin (e.g., SCY-078), 5-flucytosin, griseofulvin, haloprogin, tolnaftate, aminocandin, chlordantoin, chlorphenesin, nifuroxime, undecylenic acid, and crystal violet, and pharmaceutically acceptable salts or esters thereof.

A fourteenth aspect of the invention features a method of treating a microbial infection by administering the antimicrobial peptide to a subject having an infection.

A fifteenth aspect of the invention features a method of treating a microbial infection by administering the composition comprising the antimicrobial peptide to a subject having an infection. In particular, the microbial infection is a fungal (e.g., *Fusarium oxysporum, Pneumocystis jirovecii, Aspergillus* spp., *Coccidioides immitis/posadasii, Candida* sp., *Filobasidiella neoformans, Trichosporon, Encephalitozoon cuniculi, Enterocytozoon bieneusi, Mucor circinelloides, Rhizopus oryzae*, and *Lichtheimia corymbifera*), or a bacterial (e.g., *Acinetobacter baumannii, Bacteroides distasonis, Bacteroides fragilis, Bacteroides ovatus, Bacteroides thetaiotaomicron, Bacteroides uniformis, Bacteroides vulgatus, B. cepacia, Citrobacter freundii, Citrobacter koseri, Clostridium clostridioforme, Clostridium perfringens, C. sordellii, Enterobacter aerogenes, Enterobacter cloacae, Enterococcus faecalis, Enterococcus,* spp. *Escherichia coli, Eubacterium lentum, Fusobacterium* spp., *Haemophilus influenzae, Haemophilus parainfluenzae, Klebsiella pneumoniae, Klebsiella oxytoca, Legionella pneumophilia, Moraxella catarrhalis, Morganella morganii, Mycoplasma* spp., *Peptostreptococcus* spp., *Porphyromonas saccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus, Staphylococcus epidermidis, Stenotrophomonas maltophilia, Streptococcus agalactiae, Streptococcus constellatus, Streptococcus pneumoniae, Streptococcus pyogenes,* and *Streptococcus pyogenes*) infection. In particular, the bacterial infection is caused by *A. baoumannii* or *P. pneumoniae*. The method for treating a subject, in which the subject is a human.

A sixteenth aspect of the invention features a composition comprising the antimicrobial peptide incorporated into a medical device, a cuff, a dressing material, a mess, a hernia patch, a wound dressing, a bandage, a syringe, gloves, or a household product, a cosmetic product, a pharmaceutical product, a washing or cleaning formulation, a medical device surface, a medical device material, a fabric, a plastic, a surface of a plastic article, a paper, a nonwoven material, a wood, leather, or a metal surface.

A seventeenth aspect of the invention features a method of producing the antimicrobial peptide using chemical peptide synthesis (e.g., solid phase peptide synthesis). In particular, the method of chemical peptide synthesis using Fmoc or Boc synthesis. The method of chemically synthesizing the antimicrobial peptide having at least 85% sequence identity to SEQ ID NO: 37.

An eighteenth aspect of the invention features a method of manufacturing the antimicrobial peptides by expressing the polypeptide in a cell that has been transformed with a polynucleotide encoding the peptide, and then recovering the polypeptide from the cell or the culture media surrounding the cell (e.g., an *E. coli*, or a eukaryotic cell, such as HeLa, CHO, or HEK cell). The method of producing the antimicrobial in a cell, in which the polynucleotide is in a vector, in particular the vector of the invention described herein.

A nineteenth aspect of the invention features a kit comprising the antimicrobial polypeptide, and, optionally, an antimicrobial agent (e.g., an antibacterial agent, such as a polymixin (e.g., colistin), or an antifungal agent). The antimicrobial polypeptide of the invention used for the manufacture of a medicament for the treatment of a microbial infection in a subject (e.g., a human). The antimicrobial polypeptide of the invention for treating a microbial infection in a subject (e.g., a human).

Definitions

As used herein, the term "acidic amino acid" refers to an amino acid having a side chain containing a carboxylic acid group having a pKa between 3.5 and 4.5. Acidic amino acids are aspartic acid and glutamic acid.

The term "about" means±10% of the stated amount.

As used herein, the term "basic amino acid" refers to an amino acid whose side chain contains an amino group having a pKa between 9.5 and 13. Basic amino acids are histidine, lysine, and arginine. The term "analog" includes any polypeptide having an amino acid residue sequence substantially identical to a polypeptide described herein in which one or more residues have been conservatively substituted with a functionally similar residue and which displays the functional aspects of the polypeptides as described herein. Examples of conservative substitutions include the substitution of one non-polar (hydrophobic) residue such as isoleucine, valine, leucine, or methionine for another; the substitution of one polar (hydrophilic) residue for another such as between arginine and lysine, between glutamine and asparagine, between glycine and serine; the substitution of one basic residue such as lysine, arginine, or histidine for another; and the substitution of one acidic residue, such as aspartic acid or glutamic acid for another. The phrase conservative substitution also includes the use of a chemically derivatized residue in place of a non-derivatized residue.

The term "chemical derivative" refers to a subject polypeptide having one or more amino acid residues chemically derivatized by reaction of a functional side group. Examples of such derivatized amino acids include for example, those amino acids in which free amino groups have been derivatized to form amine hydrochlorides, p-toluene sulfonyl groups, carbobenzoxy groups, t-butyloxycarbonyl groups, chloroacetyl groups or formyl groups. Also, the free carboxyl groups of amino acids may be derivatized to form salts, methyl and ethyl esters or other types of esters or hydrazides. Also, the free hydroxyl groups of certain amino acids may be derivatized to form O-acyl or O-alkyl derivatives. Also, the imidazole nitrogen of histidine may be derivatized to form N-imbenzylhistidine. Also included as chemical derivatives are those proteins or peptides which contain one or more naturally occurring amino acid derivatives of the twenty standard amino acids. For example, 4-hydroxyproline may be substituted for proline, 5-hydroxylysine may be substituted for lysine, 3-methylhistidine may be substituted for histidine, homoserine may be substituted for serine, and ornithine may be substituted for lysine. Polypeptides described herein also include any polypeptide having one or more additions and/or deletions of residues relative to the sequence of any one of the polypeptides whose sequence is described herein.

As used herein, a "coding region" is a portion of the nucleic acid which contains codons that can be translated into amino acids. Although a "stop codon" (TAG, TGA, TAA) is not translated into an amino acid, it may be considered to be part of a coding region, if present, but any flanking sequences, for example, promoters, ribosome binding sites, transcriptional terminators, introns, 5' and 3' untranslated regions, and the like, are not part of the coding region.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is, therefore, interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "duration" refers to the length of time or a timecourse over which a therapeutic agent (e.g., a peptide described herein or a composition containing such a peptide, or polynucleotide encoding such a peptide) is administered.

As used herein, the term "host cell" refers to any kind of cellular system that can be engineered to generate the CPPs or AMPs described herein.

As used herein, the term "linker" refers to a linkage between two elements (e.g., amino acids, peptides, polypeptides, proteins, protein domains, nucleic acids, polynucleic acids, peptide nucleic acids, and small molecules (e.g., [2-(2-(Fmoc-amino) ethoxy) ethoxy] acetic acid)). A linker can be a covalent bond. A linker can also be a molecule of any length that can be used to couple, for example, a cell penetrating peptide to a compound, such as a polynucleotide (e.g., a peptide nucleic acid) or a therapeutic agent, or a detectable label, such as a protein (e.g., GFP) or a small molecule (e.g., a fluorophore, such as TAMRA, Alexa Fluor®, cyanines, DAPI, Hoechst dye, etc.). A linker may be a "cleavable linker" facilitating release of a peptide from a solid support. For example, an acid-labile linker, peptidase-sensitive linker, photolabile linker, dimethyl linker, or disulfide-containing linker (Chari et al., Cancer Res. 52:127-131 (1992). A linker also refers to a moiety (e.g., a polyethylene glycol (PEG) polymer) or an amino acid sequence (e.g., a 1-200 amino acid, 1-150 amino acid, 1-100 amino acid, 5-50 amino acid, 1-10 amino acid, or a 1-5 amino acid sequence) occurring between two peptides, polypeptides, proteins, protein domains, nucleic acids, polynucleic acids, peptide nucleic acids, or small molecules to provide space and/or flexibility between the two peptides, polypeptides, proteins, protein domains, nucleic acids, polynucleic acids, peptide nucleic acids, or small molecules. If the two linked elements are peptides, polypeptides, or peptide nucleic acids, an amino acid linker may be part of the primary sequence of a polypeptide.

As used herein, the term "nonpolar amino acid" refers to an amino acid having relatively low-water solubility. Nonpolar amino acids are glycine, leucine, isoleucine, alanine, phenylalanine, methionine, tryptophan, valine, and proline.

As used herein, the term "percent (%) identity" refers to the percentage of amino acid residues of a candidate sequence, e.g., a CPP or antimicrobial peptide (AMP), that are identical to the amino acid residues of a reference sequence, e.g., a Tat peptide, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid sequence identity of a given candidate sequence to, with, or against a given reference sequence (which can alternatively be phrased as a given candidate sequence that has or includes a certain percent amino acid sequence identity to, with, or against a given reference sequence) is calculated as follows:

$$100 \times (\text{fraction of } A/B)$$

where A is the number of amino acid residues scored as identical in the alignment of the candidate sequence and the reference sequence, and where B is the total number of amino acid residues in the reference sequence. In some embodiments where the length of the candidate sequence does not equal to the length of the reference sequence, the percent amino acid sequence identity of the candidate sequence to the reference sequence would not equal to the percent amino acid sequence identity of the reference sequence to the candidate sequence.

Two polynucleotide or polypeptide sequences are said to be "identical" if the sequence of nucleotides or amino acids in the two sequences is the same when aligned for maximum correspondence as described above. Comparisons between two sequences are typically performed by comparing the sequences over a comparison window to identify and compare local regions of sequence similarity. A "comparison window" as used herein, refers to a segment of at least about 15 contiguous positions, about 20 contiguous positions, about 25 contiguous positions, or more (e.g., about 30 to about 75 contiguous positions, or about 40 to about 50 contiguous positions, in which a sequence may be compared to a reference sequence of the same number of contiguous positions after the two sequences are optimally aligned.

As used herein, the term "pharmaceutically acceptable carrier" refers to an excipient or diluent in a pharmaceutical composition. The pharmaceutically acceptable carrier is compatible with the other ingredients of the formulation and not deleterious to the recipient. The pharmaceutically acceptable carrier may provide pharmaceutical stability to the composition (e.g., stability to a CPP or conjugate thereof, or an AMP), or may impart another beneficial characteristic (e.g., sustained release characteristics). The nature of the carrier may differ with the mode of administration. For example, for intravenous administration, an aqueous solution carrier is generally used; for oral administration, a solid carrier may be preferred.

As used herein, the term "pharmaceutical composition" refers to a medicinal or pharmaceutical formulation that contains an active ingredient at a pharmaceutically acceptable purity as well as one or more excipients and diluents that render the active ingredient suitable for the method of administration. The pharmaceutical composition includes pharmaceutically acceptable components that are compatible with, for example, a cell penetrating peptide or conjugate thereof or an AMP described herein. The pharmaceutical composition may be in aqueous form, for example, for intravenous or subcutaneous administration, in tablet or capsule form, for example, for oral administration, or in cream for, for example, for topical administration.

As used herein, the term "polar amino acid" refers to an amino acid having a chemical polarity in its side chain induced by atoms with different electronegativity. The polarity of a polar amino acid is dependent on the electronegativity between atoms in the side chain of the amino acid and the asymmetry of the structure of the side chain. Polar amino acids are serine, threonine, cysteine, histidine, methionine, tyrosine, tryptophan, asparagine, and glutamine.

As used herein, the term "subject" refers to a mammal, e.g., a human.

The term "sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, tissue culture medium, tissue extracts such as homogenized tissue, tumor tissue, cellular extracts, and combinations thereof.

As used herein, the term "therapeutically effective amount" refers to an amount, e.g., a pharmaceutical dose of a composition described herein (e.g., a composition containing a CPP or conjugate thereof or a composition containing an AMP), effective in inducing a desired biological effect in a subject or subject or in treating a subject with a medical condition or disorder described herein (e.g., cancer or a microbial infection). It is also to be understood herein that a "therapeutically effective amount" may be interpreted as an amount giving a desired therapeutic effect, either taken in one dose or in any dosage or route, taken alone or in combination with other therapeutic agents.

As used herein, the terms "treatment" or "treating" refer to reducing or ameliorating a medical condition (e.g., a disease) and/or symptoms associated therewith (e.g., cancer). It will be appreciated that, although not precluded, treating a medical condition does not require that the disorder or symptoms associated therewith be completely eliminated. Reducing or decreasing the side effects of a medical condition, such as cancer or a microbial infection, or the risk or progression of the medical condition, may be relative to a subject who did not receive treatment, e.g., a control, a baseline, or a known control level or measurement. The reduction or decrease may be, e.g., by about 1%, 2%, 3%, 4%, 5%, 6%, 7%, 8%, 9%, 10%, 20%, 30%, 40%, 50%, 60%, 70%, 80%, 90%, 95%, 97%, 99%, or about 100% relative to the subject who did not receive treatment or the control, baseline, or known control level or measurement, or may be a reduction in the number of days during which the subject experiences the medical condition or associated symptoms (e.g., a reduction of 1-30 days, 2-12 months, 2-5 years, or 6-12 years).

Wherever any of the phrases "for example," "such as," "including" and the like are used herein, the phrase "and without limitation" is understood to follow unless explicitly stated otherwise. Similarly "an example," "exemplary" and the like are understood to be non-limiting.

The term "substantially" used herein allows for deviations from the descriptor that do not negatively impact the intended purpose. Descriptive terms may be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

BRIEF DESCRIPTION OF THE DRAWINGS

The application file contains at least one drawing executed in color. Copies of this patent or patent application with color drawings will be provided by the Office upon request and payment of the necessary fee.

The following drawings form part of the present specification and are included to further demonstrate certain aspects of the present invention. The invention may be better understood by reference to one or more of these drawings in combination with the description of specific embodiments presented herein.

FIG. 4 is a table showing the amino acid sequences (SEQ ID NOs: 1-10) from eight peptide synthesis beads that were selected from the CPP-PNA705 library for sequencing by Edman degradation. They are presented here under the parent sequences Tat and penetratin (SEQ ID NOs: 1 and 2). Here, CPP positive sequences are in green and false positive sequences are red. Basic amino acids are in blue and polar amino acids are in orange.

FIG. 10A is a plot showing the results of CPP-C-TA construct vs mean TAMRA fluorescence of SYTOX negative HeLa cells. FIG. 10B is a representative flow cytometry plot of HeLa cells treated at 22° C. showing the percentage of TAMRA positive cells defined as those with TAMRA fluorescence values above 3000 units. FIG. 10C shows confocal microscopy images of HeLa cells treated in the same manner as those analyzed by flow cytometry were visualized using a confocal scanning Nikon Eclipse Ti2 inverted microscope. TAMRA was excited using the 543 nm laser and SYTOX Green was excited using the 488 nm laser.

FIG. 11A is a plot showing the results of the CPP-C-TA construct vs mean TAMRA fluorescence of SYTOX negative HepG2 cells. FIG. 11B is a representative flow cytometry plot of HepG2 cells treated at 22° C. showing the percentage of TAMRA positive cells defined as those with TAMRA fluorescence values above 3000 units. FIG. 11C shows confocal microscopy images of HepG2 cells treated in the same manner as those analyzed by flow cytometry were visualized using a confocal scanning Nikon Eclipse Ti2 inverted microscope. TAMRA was excited using the 543 nm laser and SYTOX Green was excited using the 488 nm laser.

FIG. 12A is a plot showing the results of the CPP-C-TA construct vs mean TAMRA fluorescence of SYTOX negative HCT116 cells. FIG. 12B is a representative flow cytometry plot of HCT116 cells treated at 22° C. showing the percentage of TAMRA positive cells defined as those with TAMRA fluorescence values above 3000 units. FIG. 12C shows confocal microscopy images of HCT116 cells treated in the same manner as those analyzed by flow cytometry were visualized using a confocal scanning Nikon Eclipse Ti2 inverted microscope. TAMRA was excited using the 543 nm laser and SYTOX Green was excited using the 488 nm laser.

FIG. 13A is a plot showing the results of the CPP-C-TA construct vs mean TAMRA fluorescence of SYTOX negative MCF-7 cells. FIG. 13B is a representative flow cytometry plot of MCF-7 cells treated at 22° C. showing the percentage of TAMRA positive cells defined as those with TAMRA fluorescence values above 3000 units. FIG. 13C shows confocal microscopy images of MCF-7 cells treated in the same manner as those analyzed by flow cytometry were visualized using a confocal scanning Nikon Eclipse Ti2 inverted microscope. TAMRA was excited using the 543 nm laser and SYTOX Green was excited using the 488 nm laser.

FIG. 14A is a plot showing the results of the CPP-C-TA construct vs mean TAMRA fluorescence of SYTOX negative RAW264.7 cells. FIG. 14B is representative flow cytometry plot of RAW264.7 cells treated at 22° C. showing the percentage of TAMRA positive cells defined as those with TAMRA fluorescence values above 3000 units. FIG. 14C shows confocal microscopy images of RAW264.7 cells treated in the same manner as those analyzed by flow cytometry were visualized using a confocal scanning Nikon Eclipse Ti2 inverted microscope. TAMRA was excited using the 543 nm laser and SYTOX Green was excited using the 488 nm laser.

FIG. 17A is a plot showing the flow cytometric analysis of CPP-GFP-11 delivery to HeLa cells expressing GFP1-10 and mCherry transgenes. The percentage of GFP positive cells was determined. Cells were incubated with varying concentrations of CPP-GFP-11 for 30 minutes and live cells were identified by forward and side scatter. Doublets were excluded in two gating steps using SSC-H×

SSC-W and FSC-H×FSC-W. FIG. 17B is a graph showing the mean GFP fluorescence recorded in the flow cytometry analysis of FIG. 17A. To assess the role of proteases on CPP mediated GFP-11 delivery, D-form versions of Tat and CPP-1 were synthesized (with L-form GFP-11) and analyzed alongside the L-form sequence.

FIG. 20A is a plot showing the sterilizing activity of library members in the presence of varying concentrations of bacterial cells. FIG. 20B is a plot showing the sterilizing activity of library members in the presence of varying concentrations of RBCs. FIG. 20C presents the results of hemolytic activity of the library peptides. Overall, as cell concentration increased the sterilizing activity decreased, and with few exceptions the library had a low propensity to induce hemolysis.

FIG. 21A is a plot of the results of the library against *E. coli* and *P. aeruginosa* in the absence of RBCs. FIG. 21B is a plot of the results of the library against *E. coli* and *P. aeruginosa* in the presence of RBCs. FIG. 21C is a plot of the results of the library against *P. aeruginosa* and methicillin-resistant *S. aureus* (MRSA) in the absence of RBCs. FIG. 21D is a plot of the results of the library against *P. aeruginosa* and methicillin-resistant *S. aureus* (MRSA) in the presence of RBCs.

FIG. 22A shows a plot of the analysis results for the peptide library members based on all three assays. The template peptide, ARVA (SEQ ID NO: 40), is indicated with a red circle. The peptide sequences isolated in this screen are indicated with yellow stars. FIG. 22B is a plot showing the distribution of the hemolysis induction observed in the screen. Most peptides were below 5%. FIG. 22C is a plot showing the distribution of zones of inhibition in radial diffusion assays. As compared to assays without RBCs, the positive rate and average size of the zones is much smaller.

FIG. 24A is a plot showing the results for isolated AMPs vs. *E. coli*. FIG. 24B is a plot showing the results for isolated AMPs vs. *P. aeruginosa*. FIG. 24C is a plot showing the results for isolated AMPs vs. *S. aureus*. (N=3)

FIG. 25A is a plot showing the results for the AMP ARVA (SEQ ID NO: 40). FIG. 25B is a plot showing the results for the AMP CHUK1. FIG. 25C is a plot showing the results for the AMP CHUK2. FIG. 25D is a plot showing the results for the AMP GNS1. FIG. 25E is a plot showing the results for the AMP GNS2. FIG. 25F is a plot showing the results for the AMP DBS1. FIG. 25G is a plot showing the results for the AMP DBS2. FIG. 25H is a plot showing the results for the AMP DBS3. FIG. 25I is a plot showing the results for the AMP DBS4. FIG. 25J is a plot showing the results for the AMP DBS5.

FIG. 26A is a plot showing the results of AMPs against human RBCs. FIG. 26B is a plot showing the results of AMPs against CCLP-1 cells, a human liver cancer cell line.

FIG. 27A is a plot showing the efficacy of AMPs against *E. coli* in the absence of RBCs. FIG. 27B is a plot showing the efficacy of AMPs against *E. coli* in the presence of RBCs. FIG. 27C is a plot showing the efficacy of AMPs against *S. aureus* in the absence of RBCs. FIG. 27D is a plot showing the efficacy of *S. aureus* in the presence of RBCs. FIG. 27E is a plot showing the efficacy of AMPs against *P. aeruginosa* in the absence of RBCs. FIG. 27F is a plot showing the efficacy of AMPs against *P. aeruginosa* in the presence of RBCs.

FIG. 28A a plot showing the results of broth dilution assays against six different microorganisms in the absence and presence of $1\times10^9$ RBCs/mL. FIG. 28B a plot showing the results of a radial diffusion assay for D-NOGCON and D-ARVA against *E. coli* in the presence of $1\times10^8$ to $1\times10^9$ RBCs/mL. FIG. 28C a plot showing the results of a radial diffusion assay for D-NOGCON and D-ARVA against *S. aureus* in the presence of $1\times10^8$ to $1\times10^9$ RBCs/mL. FIG. 28D is a graph presenting the cytotoxicity of D-NOGCON and D-ARVA against human RBCs. FIG. 28E is a graph presenting the cytotoxicity of D-NOGCON and D-ARVA against human CCLP-1 epithelial cells.

FIG. 29A is a plot showing weight loss by mice treated with 50 μL of 100 μM D-NOGCON, every 8 hours for 3 days. FIG. 29B is a plot showing weight loss by mice treated with 50 μL of 50 μM D-NOGCON, every 12 hours for 3 days.

FIG. 30A is a plot showing the weight loss of mice over time after treatment with 50 μL of 50 μM D-NOGCON or 50 μL of PBS every 12 hours. FIG. 30B show survival curves for mice infected with *P. aeruginosa*.

FIG. 30C is a plot showing the CFU burdens in the lungs of peptide-treated and vehicle-treated animals. (N=3 per group)

FIG. 32 is a table presenting the results of selected peptides challenged with multidrug resistant clinical isolates of *A. baumannii*, and *K. pneumoniae*.

FIGS. 35A-35B are images showing bacterial infection in a deep wound control animals. FIGS. 35C-35D are images showing bacterial infection in a deep wound in animals prior to treatment with 50 μg (20 μL, 0.025% acetic acid) of D-NOGCON.

FIGS. 36A-36B are images showing bacterial infection in a deep wound control animals. FIGS. 36C-36D are images showing control of a bacterial infection in a deep wound in animals prior to treatment with 50 μg (20 μL, 0.025% acetic acid) of D-NOGCON.

FIG. 37A Integrated luminescence from control animal #1 and treated animal #1 over the first 5 days of the experiment. Animals are treated on Days 0, 1 and 2 only. Data suggest significant protection, slowing of bacterial growth and more rapid clearance over control. FIG. 37B Sum of activity and behavior scores. Scale is 0 (normal) to 3 (maximally abnormal) each for activity/nesting, movement, grip strength, coat condition, and posture. Maximum score (worst condition) =15. These preliminary data suggest that treated mice have more normal behavior.

DETAILED DESCRIPTION

Figure 1:
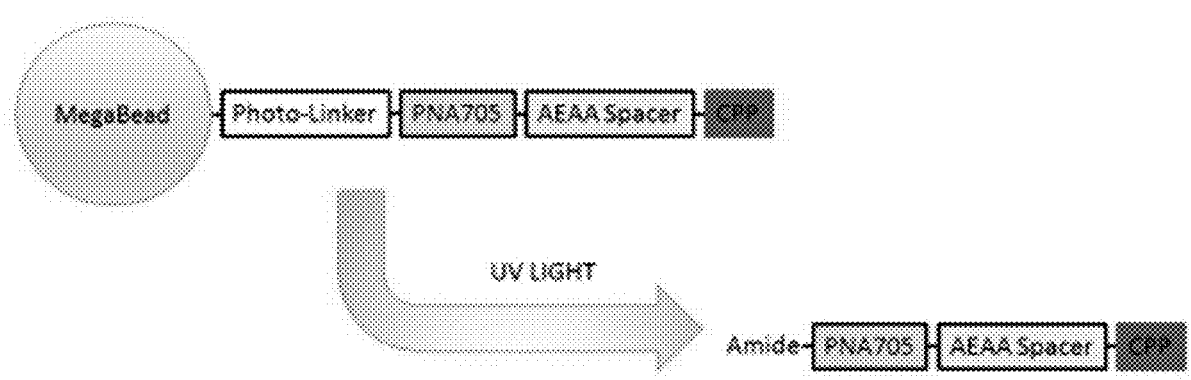
FIG. 1 is a schematic of a TENTAGEL® $NH_2$ functionalized megabead conjugated to a photolabile linker, the 18 base PNA705 sequence (cctcttacctcagttaca) (SEQ ID NO: 11), and a [2-(2-(Fmoc-amino) ethoxy) ethoxy] acetic acid spacer. The beads were then subjected to the split and combine peptide synthesis method known in the art. Following deprotection of the side chain and the terminal Fmoc group, the amidated peptide-PNA hybrid sequence is cleaved from the support by exposure to UV light and dissolved in sterile $ddH_2O$ for downstream analysis.

Described herein are cell penetrating peptides (CPPs), polynucleotides encoding the peptides, and methods of using these peptides in research, and in the diagnosis, prevention, and treatment of a medical condition. We identified CPPs that can deliver cargo to intracellular compartments. The cargo can be a compound, such as a small molecule, macromolecule (e.g., a peptide, polypeptide, protein, nucleic acid, polynucleic acid, peptide nucleic acid, antibody, polymer, bioactive peptides, or any fragments thereof), or a fluorescent molecule.

We used synthetic molecular evolution (SME), which is an iterative process of designing rational combinatorial libraries and exploring the sequence space around known sequence templates, to screen libraries orthogonally for peptides that have a desired set of properties. Using SME we rationally introduced constrained amino acid variability at specific locations throughout a CPP template sequence to identify and improve CPPs.

Peptide nucleic acids (PNAs) bind with high sequence specificity to DNA and RNA and can inhibit transcription, initiate transcription, inhibit translation, inhibit replication, and isolate/modify active genes. Further, as self-assembling scaffolds, they have received attention as nanotechnological agents. While these properties make PNA an exciting candidate biotechnological tool and therapeutic, intracellular delivery remains a challenge. Described herein are CPPs capable of efficiently delivering both PNA and polypeptide cargoes to the interior of living cells without inhibiting the functionality of the PNA/polypeptide cargoes.

Also described herein are antimicrobial peptides (AMPs) capable of disrupting the cellular membrane of multiple infectious pathogens (e.g., bacterial or fungal) with improved hemocompatibility (e.g., in the presence of human red blood cells, or human serum). We identified AMPs that retain activity against bacterial pathogens, including multidrug resistant strains, in the presence of high concentration of red blood cells. These peptides show excellent antimicrobial activity towards a broad spectrum of bacterial species. Further, the AMPs retain this activity in the presence of eukaryotic cells and are less toxic than many previously described antimicrobial peptides.

Cell Penetrating Polypeptides

We used synthetic molecular evolution (SME) to simultaneously optimize for delivery of a cargo and for solubility of the CPP-conjugate complex (e.g., a CPP-PNA complex), efficient delivery at low micromolar concentration, and low toxicity. By way of example and not limitation, a CPP described herein can have at least 85% or more (e.g., 90%, 95%, 97%, 98%, 99%, or 100%) sequence identity to one or more of the sequences listed in Table 1 (SEQ ID NOs: 1-10) or any fragment thereof (e.g., fragments of at least 3, 5, 10 or more consecutive amino acids in length), in particular, the sequences of SEQ ID NOs: 3-10.

TABLE 1

List of CPP Sequences

| SEQ ID NO | Description | Sequence |
|---|---|---|
| 1. | TAT | GRKKRRQRRRPPQ |
| 2. | Penetratin | RQIKIWFQNRRMKWKK |
| 3. | CPP-1 | RKKRWFRRRRPKWKK |
| 4. | CPP-2 | GRKKRWFRRRRMKWKK |
| 5. | CPP-3 | RIKRRFRRLRPKWKK |
| 6. | CPP-4 | RRKKIWFRRLRMK |
| 7. | CPP-5 | GQIKRRFRRLRPK |
| 8. | CPP-6 | RRKKRRFRRRPPK |
| 9. | CPP-7 | GRIKRRQRRLPPQ |
| 10. | CPP-8 | RIKRRQQRLRPQ |
| 11. | PNA705 | cctcttacctcagttaca |
| 12 | GFP-11 | RDHMVLHEYVNAAGIT |
| 13 | Arg9 | RRRRRRRRR |
| 14 | ACTB1 | ccttgcacatgccggag |

TABLE 1-continued

List of CPP Sequences

| SEQ ID NO | Description | Sequence |
|---|---|---|
| 15 | ACTB2 | acagagcctcgcc tttg |
| 16 | pTRE-Luc IVS2- Insert | acagtgataattt ctgggttaaggc |
| 17 | pTRE-Luc IVS2- Downstream | tcaatcagagtgc ttttggcg |
| 18 | pTRE-Luc IVS2- Bridge | ttacgatcccttc aggattacaa |

Featured CPPs can promote the internalization of a cargo (e.g., a compound) into a tissue, organ, or living cell. Examples of a tissue, organ, or living cell are the liver or liver cells (e.g., hepatocytes), a kidney or kidney cell, a tumor or tumor cell, the CNS or CNS cells (central nervous system (e.g., brain and/or spinal cord), the PNS or PNS cells (Peripheral Nervous System), a lung or lung cells, the vasculature or vascular cells, the skin or skin cells (e.g., dermis cells and/or follicular cells), the eye or ocular cells (e.g., macula, fovea, cornea, retina), bone, gall bladder, spleen, small intestine, large intestine, stomach, pancreas, appendix, urinary bladder, and an ear or cells of the ear (e.g., cells of the inner ear, middle ear, and/or outer ear), among other known tissues and organs.

When aligned, as seen in FIG. 4, the CPPs described herein can have a Lys at residue 4 and/or an Arg at residue 9. In addition, or alternatively, the CPPs may have an RKKR, RIKR, RKKI, or QIKR at residues 2-4, and/or an RRR, RRL, or QRL at residues 8-10, and/or a KWKK motif at residues 14-16.

CPPs described herein can have at least 85% or more (e.g., 90%, 95%, 97%, 98%, 99%, or 100%) sequence identity to one or more of the sequences listed in Table 1 (SEQ ID NOs: 1-10) or any fragment thereof (e.g., fragments of at least 3, 5, 10 or more consecutive amino acids in length), in particular, the sequences of SEQ ID NOs: 3-10.

CPPs described herein exhibit one or more of the following characteristics: a fold increase over 15× and up to 1000× (e.g., 20×, 25×, 30×, 35×, 40×, 50×, 70×, 90×, 100×, 150×, 200×, 250×, 300×, 350×, 400×, 450×, 500×, 550×, 600×, 650×, 700×, 750×, 800×, 850×, 900×, 950×, 999×) efficiency in cellular membrane penetration over Tat or penetratin (SEQ ID NOs: 1 and 2, respectively), or the ability to internalize a cargo (e.g., a compound) with a fold increase over 15× and up to 1000× (e.g., 20×, 25×, 30×, 35×, 40×, 50×, 70×, 90×, 100×, 150×, 200×, 250×, 300×, 350×, 400×, 450×, 500×, 550×, 600×, 650×, 700×, 750×, 800×, 850×, 900×, 950×, 999×) efficiency in cellular membrane penetration over Tat or penetratin (SEQ ID NOs: 1 and 2, respectively).

Also featured are peptidomimetics of the CPPs described herein, which include chemically modified peptides, peptide-like molecules containing non-naturally occurring amino acids, peptoids and the like. The CPP peptidomimetics retain the characteristics of the membrane penetrating peptides described herein, having a fold increase over 15× and up to 1000× (e.g., 20×, 25×, 30×, 35×, 40×, 50×, 70×, 90×, 100×, 150×, 200×, 250×, 300×, 350×, 400×, 450×, 500×, 550×, 600×, 650×, 700×, 750×, 800×, 850×, 900×, 950×, 999×) efficiency in cellular membrane penetration over Tat or penetratin (SEQ ID NOs: 1 and 2, respectively).

Also featured are CPPs or analogs thereof having substantially the same effect as the CPPs described herein. Such CPPs include, but are not limited to, a substitution, addition, or deletion mutant of the CPPs described herein (e.g., in which one or two amino acids of the CPPs (e.g., the CPPs of SEQ ID NOs: 3-10) are substituted with another amino acid, are deleted, or are added to the polypeptides). Also encompassed are peptides that are substantially homologous to the polypeptides. A variety of sequence alignment software programs are available in the art to facilitate determination of homology or equivalence of any protein to a protein of the invention.

In some peptides as described herein, D-amino acids may be used instead of or in addition to L-amino acids. Glycine does not have chirality due to two hydrogens. However, all other amino acids may be D-amino acids, including D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, AND D-VAL. In particular, one or more of the amino acids of the CPPs, such as those shown in FIG. 4 (e.g., SEQ ID NOs: 3-10), may be substituted with a D-amino acid.

The CPPs disclosed herein are a unique hybrid group of cell penetrating peptides identified by their ability to deliver nucleic acid molecules, including PNA molecules, as well as functional peptide cargo. PNA/Peptide conjugated CPPs can be a powerful delivery strategy that is fast, function at low micromolar concentrations in a variety of cell types, and have low cytotoxicity. Further, they efficiently deliver both fluorescent molecules and bioactive peptides to multiple cell types.

CPP-Conjugates

The CPP peptides described above can be modified to include a cargo, for example a compound, in order to form a CPP-conjugate.

Examples of cargo (e.g., compounds) that can be conjugated to a CPP described herein are small molecules, macromolecules (e.g., peptides, polypeptides, proteins, nucleic acids, polynucleic acids, peptide nucleic acids, antibodies, bioactive peptides, polymers or any fragments thereof), and fluorescent molecules (e.g., green fluorescent protein, cyan fluorescent protein, yellow fluorescent protein, red fluorescent protein, phycoerythrin, allophycocyanin, hoescht, 4',6-diamidino-2-phenylindole (DAPI), TAMRA, propidium iodide, fluorescein, coumarin, rhodamine, tetramethylrhoadmine, and cyanine). By way of example and not limitation, further examples of cargo that can be conjugated to a CPP are described in Table 2. The CPP conjugate can be modified to include a therapeutic agent, examples of therapeutics are described in Table 2. The CPP conjugated to a therapeutic agent can be used to treat a medical condition, such as the medical conditions described in Table 2.

TABLE 2

Exemplary therapeutic agents that can be administered with or conjugated to cell penetrating peptides to treat disease

| Disease or Condition | Therapeutic Agent |
| --- | --- |
| Diabetes, altered glycemic states | Insulin, insulotropin, glucagon |
| Skeletal growth retardation | Human growth hormone |
| Anemia | Erythropoietin (EPO), hemoglobins |
| Obesity | Ob gene translation product (leptin) |
| Immunodeficiency (e.g., AIDS) | Adenosine deaminase, purine nucleoside phosphorylase, CD-4 |
| Hemophilia A | Factor VIII |
| Hemophilia B | Factor IX |
| Emphysema | $\alpha_1$-antitrypsin |
| Hypercholesterolemia | LDL receptor protein |
| Pernicious anemia | Intrinsic factor |
| Hypoalbuminemia | Albumin |
| Gaucher's disease | B-glucosidase (glucocerebrosidase) |
| Cystic fibrosis | CF transmembrane conductance regulator |
| Cardiovascular disease | Tissue Plasminogen Activator (tPA), urokinase, streptokinase, antithrombin III, Apolipoproteins (e.g., APO B48, A1), Low Density lipoprotein receptor, vascular endothelial growth factor (VEGF) |
| Calcium mineral diseases | Calcitonin, parathyroid hormone (PTH), PTH-like hormone |
| Severe Combined Immunodeficiency (SCID) | Adenosine deaminase |
| Phenylketonuria | Phenylalanine hydroxylase |
| von Willebrand's disease | von Willebrand Factor |
| Cancers, cancer suppression | Tumor Necrosis Factors (TNFs), cytokines, anti-neoplastic agents (e.g., vincristine, doxorubicin, tamoxifen, methotrexate), interleukins (ILs), interferons (INFs), p53 and related, anti-BRCAs, anti-VEGF (bevacizumab), anti-Epidermal Growth Factor (EGF), oncogene anti-sense RNAs, antibodies (e.g., Rituximab; Daclizumab; Basiliximab; Palivizumab; Infliximab; Trastuzumab; Gemtuzumab ozogamicin; Alemtuzumab; Ibritumomab tiuxetan; Adalimumab; Omalizumab; Tositumomab-I-131; Efalizumab; Cetuximab; Bevacizumab; Natalizumab; Tocilizumab; Panitumumab; Ranibizumab; Eculizumab; Certolizumab pegol; Golimumab; Canakinumab; Ustekinumab; Ofatumumab; Denosumab; Motavizumab; Raxibacumab; Belimumab; Ipilimumab; Brentuximab Vedotin; Pertuzumab; Ado-trastuzumab emtansine; or Obinutuzumab), or checkpoint inhibitors (e.g., nivolumab, pidilizumab/CT-011, pembrolizumab, ipilimumab, or tremelimumab) |
| Peripheral vascular disease | VEGF, endothelins |
| Neurodegenerative states, and post neural trauma conditions | Ciliary Neurotrophic Factor (CNTF), Brain Derived Neurite Factor (BDNF), Nerve Growth Factor (NGF), tyrosine hydroxylase |
| Retarded fracture healing | Bone morphogenic proteins (BMP) |
| Lactose insufficiency | Lactase |
| Wound healing | Epidermal Growth Factors, Transforming Growth Factors, Granulocyte-Colony Stimulating Factors, Fibroblast Growth Factors, Interferons, Interleukins, Insulin-like growth Factors |
| Thrombosis, hypercoagulability | Antithrombins, urokinases, tPAs, hirudins, streptokinase |
| Diabetes insipidus | Antidiuretic hormone (ADH) |
| Psychiatric Disorders | Selective Serotonin Reuptake Inhibitors, anti-psychotic bio-substances |
| Pain Control | Endorphins |
| Endocrineopathies | Estrogens, Androgens, mineralocorticoids, glucocorticoids, anabolic steroids, etc. |
| Hypothyroidism | Thyroid hormones, thyroglobulins |
| Muscular dystrophy | Dystrophin |
| Infections (bacterial, fungal, viral) | Antimicrobial polypeptides |
| Shock, Sepsis | Lipid Binding Protein (LBP) |
| Leukemia | L-asparaginase |
| Disorders of digestive, pancreatic states | Pepsin, trypsin, chymotrypsin, cholecystokinin, sucrase, carboxypeptidase |
| Oxidative Stress, Neurodegenerative Disorders | Catalase |
| Hypouricasemia, Gout | Uricase |

TABLE 2-continued

Exemplary therapeutic agents that can be administered with or conjugated to cell penetrating peptides to treat disease

| Disease or Condition | Therapeutic Agent |
| --- | --- |
| Ehlers Danlos | Elastase |
| Thrombocytopenia | Thrombopoietin (TPO) |
| SCID/ADA deficiency | Adenosine deamidase |
| Porphyria | Porphobilinogen deaminase |
| Disease or Condition | Therapeutic Agent |
| Inborn errors of carboxylic and amino acid metabolism, (e.g., glutaric acidemia) | Specific enzymes catalyzing transformations at genetic block points, (e.g., glutaryl CoA dehydrogenase) |
| Homocystinuria | Cystathionine B-synthase |
| Wilson's Disease, Menke's Disease | Specific copper transporting ATPase's |
| Thalassemia | β-globin |
| Sickle Cell Anemia | α-globin |
| Baldness | Sonic hedgehog gene products |
| Hashimoto's Thyroiditis, | Thyroid hormone |
| Wet Age-Related Macular Degeneration or Retinal Dystrophy | VEGF trap (e.g., a soluble decoy receptor described in Holash et al., Proc Natl Acad Sci U.S.A. 99:11383-11398, 2002, e.g., VEGF-Trap$_{parental}$, VEGF-Trap$_{\Delta B1}$, VEGF-Trap$_{\Delta B2}$, VEGF-Trap$_{R1R2}$, e.g., aflibercept), soluble forms of VEGF receptors (e.g., soluble VEGFR-1 or NRP-1), platelet factor-4, prolactin, SPARC, VEGF inhibitory antibodies (e.g., bevacizumab or ranibizumab). |
| Osteoarthritis or Rheumatoid Arthritis | TNFα inhibitors (adalimumab, etanercept, infliximab, golimumab, certolizumab), interleukin-6 (IL6) receptor inhibitors (e.g., tocilizumab), IL1 receptor inhibitors (e.g., anakinra), or other agents used to treat RA (e.g., abatacept, rituximab) |
| Inflammatory Bowel Disease, Crohn's disease, Ulcerative Colitis | TNFαinhibitors (adalimumab, etanercept, infliximab, golimumab, certolizumab), mesalazine, prednisone, azathioprine, methotrexate |
| Addison's Disease | Aldosterone, cortisol, glucocorticoids, mineralocorticoids, androgens |
| Hurler syndrome | Alpha-L iduronidase |
| Niemann-Pick disease | Sphingomyelin phosphodiesterase1 (SMPD1), NPC1 protein, or NPC2 protein |
| Tay-Sachs disease | beta-hexosaminidase A |
| Fabry disease | alpha galactosidase |
| Krabbe disease | Galactosylceramidase |
| Galactosemia | Galactokinase or galactose-1-phosphate uridyltransferase |
| Maple syrup urine disease | Enzymes of the branched-chain alpha-keto acid dehydrogenase complex |
| Phenylketonuria | Phenylalanine hydroxylase |
| Glycogen storage diseases (GSDs) | GSD0: Glycogen synthase (GYS2); GSD1/von Gierke's disease: Glucose-6-phosphatase (G6PC); GSD 2/Pompe's disease: Acid alpha-glucosidase (GAA); GSD 3/Cori's disease or Forbes' disease: Glycogen debranching enzyme (AGL); GSD 4/Andersen disease: Glycogen branching enzyme (GBE1); GSD 5/McArdle disease: Muscle glycogen phosphorylase (myophosphorylase) (PYGM); GSD 6/Hers' disease: Liver glycogen phosphorylase (PYGL) or muscle phosphoglycerate mutase (PGAM2); GSD 7/Tarui's disease: Muscle phosphofructokinase (PKFM); GSD 9: Glycogen phosphorylase kinase B (PHKA2, PHKB, PHKG2, or PHKA1), GSD 10: Enolase 3 (ENO3); GSD 11: Muscle lactate dehydrogenase (LDHA); Fanconi-Bickel syndrome: Glucose transporter 2 (GLUT2); GSD 12: Aldolase A (ALDOA); GSD 13: β-enolase (ENO3); GSD 15: Glycogenin-1 (GYG1) |
| Mitochondrial disorders | Leber's hereditary optic neuropathy (LHON): NADH dehydrogenase; Leigh syndrome: thiamine-diphosphate kinase, thiamine triphosphate, or pyruvate dehydrogenase; Neuropathy, ataxia, retinitis pigmentosa, and ptosis (NARP: ATP synthase; |

TABLE 2-continued

Exemplary therapeutic agents that can be administered with or conjugated to cell penetrating peptides to treat disease

| Disease or Condition | Therapeutic Agent |
|---|---|
| | Myoneurogenic gastrointestinal encephalopathy (MNGIE): thymidine phosphorylase (TYMP); Mitochondria myopathy, encephalomyopathy, lactic acidosis, stroke-like symptoms (MELAS): NADH dehydrogenase |
| Friedrich's ataxia | Frataxin (FXN) |
| Peroxisomal disorders | Zellweger syndrome: Proteins encoded by PEX1, PEX2, PEX3, PEX5, PEX6, PEX10, PEX12, PEX13, PEX14, PEX16, PEX19, or PEX26; Adrenoleukodystrophy: protein encoded by ABCD1 |
| Metal metabolism disorders | Wilson disease: Wilson disease protein (ATP7B); Hemochromatosis: Human hemochromatosis protein (HFE) |
| Organic acidemias | Methylmalonic acidemia: methylmalonyl CoA mutase, methylmalonyl CoA epimerase, adenosylcobalamin Propionic academia: propionyl-CoA carboxylase |
| Urea cycle disorders | Ornithine transcarbamylase (OTC), deficiency: Ornithine transcarbamylase; Arginase (ARG1) deficiency: Arginase; Argininosuccinate lyase (ASL) deficiency: Argininosuccinate lyase; Argininosuccinate synthase 1 (ASS1) deficiency: Argininosuccinate synthase 1; Citrin deficiency: Citrin; Carbamoyl phosphate synthase 1 (CPSI) deficiency: Carbamoyl phosphate synthase 1; N-acetylglutamate synthase (NAGS) deficiency: N-acetylglutamate synthase; Ornithine translocase (ORNT1) deficiency: Ornithine translocase |

Antimicrobial Peptides (AMP)

Also featured are antimicrobial peptides capable of disrupting the cellular membrane of multiple pathogens with improved hemocompatibility, (e.g., in the presence of human red blood cells, human serum). We used a combinatorial library followed by SME to simultaneously optimize for pathogen (e.g., a bacterial, such as *P. aeruginosa*, *A. baumannii*, and *E. coli*, or a fungal, such as *Candida* spp., pathogen) activity, increased activity in the presence of eukaryotic cells, and decreased hemolytic activity and toxicity. For example, an AMP described herein can have at least 85% or more (e.g., 90%, 95%, 97%, 98%, 99%, or 100%) sequence identity to one or more of the sequences listed in Table 3 (SEQ ID NOs: 19-42) or any fragment thereof (e.g., fragments of at least 3, 5, 10 or more consecutive amino acids in length), in particular, the sequence of SEQ ID NO: 37.

TABLE 3

List of AMP Sequences

| SEQ ID NO | Description | Sequence |
|---|---|---|
| 19 | CHUK1 | RRGWALRPVLAFGRR |
| 20 | CHUK2 | RRGWARRLAAAYGRR |
| 21 | GNS2 | RRGWAFRRALAYGRR |
| 22 | DBS1 | RRGWARRLFFAYGRR |
| 23 | DBS2 | RRGWAARLFAAFGRR |
| 24 | DBS3 | RRGWARRLFAAFGRR |
| 25 | DBS4 | RRGWARRLVFAFGRR |
| 26 | DBS5 | RRGWARALAFAFGR |
| 27 | RAT1 | RRWARRLFFAYRR |
| 28 | RAT2 | RRWNLALTLTYYRR |
| 29 | RAT3 | RRGWALRLVLAYGRR |
| 30 | L-RAT4 | RRGWARRLAFAFGRR |
| 31 | D-RAT4 | RRGWARRLAFAFGRR (All D) |
| 32 | RAT5 | RRGWARRLRLAFAFGRR |
| 33 | RAT6 | RRGWARRLAFAFAFGRR |
| 34 | D-KON | KKGWAKKLAFAFGKK (All D) |
| 35 | D-GNS2 | RRGWAFRRALAYGRR (All D) |
| 36 | D-DBS1 | RRGWARRLFFAYGRR (All D) |
| 37 | D-NOGCON | RRWARRLAFAFRR (All D) |
| 38 | L-NOGCON | RRWARRLAFAFRR |
| 39 | L-KON | KKGWAKKLAFAFGKK |

TABLE 3-continued

List of AMP Sequences

| SEQ ID NO | Description | Sequence |
|---|---|---|
| 40 | ARVA | RRWARLRLVLAY |
| 41 | GNS1 | RGWARRRFFASG |
| 42 | RAT7 | RRGWARRLAFGRR |

The featured AMPs have from about 6 to about 20 amino acids (e.g., from about 6 amino acids to about 18 amino acids, from about 6 amino acids to about 16 amino acids, from about 6 amino acids to about 14 amino acids, from about 10 amino acids to about 18 amino acids, from about 10 amino acids to about 16 amino acids, from about 12 amino acids to about 18 amino acids, from about 12 amino acids to about 16 amino acids.

AMPs described herein can have at least 85% or more (e.g., 90%, 95%, 97%, 98%, 99%, or 100%) sequence identity to one or more of the sequences listed in Table 3 (SEQ ID NOs: 19-42) or any fragment thereof (e.g., fragments of at least 3, 5, 10 or more consecutive amino acids in length), which contain two charged residues (e.g., R or K) at the beginning and/or end of the AMP (e.g., the AMP begins with RR, RK, KR, or KK and/or ends with RR, RK, KR, or KK or any variation thereof), and may have an $AX_1AX_2$ motif, in which A is alanine and $x_1$ and $x_2$ are aromatic residues (e.g., phenylalanine, tyrosine, or tryptophan) within three amino acids (e.g., one, two or three amino acids) from the C-terminal end of the AMP.

The antimicrobial peptide (e.g., an antibacterial peptide) described herein may be substantially amphipathic. Furthermore, the antimicrobial peptide (e.g., an antibacterial peptide) may be substantially cationic and amphipathic. The antimicrobial peptide (e.g., an antibacterial peptide) may also be cytostatic, cytotoxic, or both, to a Gram-positive bacterium. The antimicrobial peptide (e.g., an antibacterial peptide) may be cytostatic, cytotoxic, or both to a Gram-negative bacterium. The antimicrobial peptide may be cytostatic, cytotoxic, or both to a virus, fungus, protozoan, parasite, or a combination thereof. The antimicrobial peptide may be cytotoxic, cytotoxic, or both to a tumor or cancer cell (e.g., a human tumor and/or cancer cell). The antimicrobial peptide (e.g., an antibacterial peptide) may be manufactured as a secreted peptide (e.g., as a proprotein with a cleavable signal peptide).

The AMPs described herein may be capable of reducing an infection by a bacterial pathogen (e.g., *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *B. cepacia*, *Citrobacter freundii*, *Citrobacter koseri*, *Clostridium clostridioforme*, *Clostridium perfringens*, *C. sordeffii*, *Enterobacter aerogenes*, *Enterobacter cloacae*, *Enterococcus faecalis*, *Enterococcus* spp. (vancomycin susceptible and resistant isolates), *Escherichia coli* (including ESBL and KPC producing isolates), *Eubacterium lentum*, *Fusobacterium* spp., *Haemophilus influenzae* (including beta-lactamase positive isolates), *Haemophilus parainfluenzae*, *Klebsiella pneumoniae* (including ESBL and KPC producing isolates), *Klebsiella oxytoca* (including ESBL and KPC producing isolates), *Legionella pneumophilia*, *Moraxella catarrhalis*, *Morganella morganii*, *Mycoplasma* spp., *Peptostreptococcus* spp., *Porphyromonas saccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus* (methicillin susceptible and resistant isolates), *Staphylococcus epidermidis* (methicillin susceptible and resistant isolates), *Stenotrophomonas maltophilia*, *Streptococcus agalactiae*, *Streptococcus constellatus*, *Streptococcus pneumoniae* (penicillin susceptible and resistant isolates), *Streptococcus pyogenes*, or *Streptococcus pyogenes*) and/or a fungal pathogen (e.g., from phylum Ascomycota (e.g., *Ajellomyces* spp., *Alternaria* spp., *Aschersonia* spp., *Aspergillus* spp., *Arthroderma* spp., *Ascochyta* spp., *Bipolaris* spp., *Blastomyces* spp., *Botryotinia* spp., *Chaetomium* spp., *Cladosporium* spp., *Coccidioides* spp., *Curvularia* spp., *Emericella* spp., *Emmonsia* spp., *Epicoccum* spp., *Exophiala* spp., *Fusarium* spp., *Geomyces* spp., *Geotrichum* spp., *Gibberella* spp., *Histoplasma* spp., *Magnaporthe* spp., *Metarhizium* spp., *Monascus* spp., *Mycospaerella* spp., *Nectria* spp., *Neosartorya* spp., *Neurospora* spp., *Paecilomyces* spp., *Paracoccidioides* spp., *Penicillium* spp., *Phaeosphaeria* spp., *Phialemonium* spp., *Podospora* spp., *Pyrenophora* spp., *Sclerotinia* spp., *Scopulariopsis* spp., *Sporothrix* spp., *Stachybotrys* spp., *Stemphylium* spp., *Talaromyces* spp., *Trichophyton* spp., *Trichothecium* spp., *Tricoderma* spp., *Tuber* spp., *Uncinocarpus* spp., or *Verticillium* spp.), phylum Basidomycota (e.g., *Moniliophthora* spp., *Sporobolomyces* spp., *Trichosporon* spp., *Ustilago* spp., *Cryptococcus* spp. or *Rhodotorula* spp.), phylum Chytridiomycota, phylum Zygomycota (e.g., *Absidia* spp., *Amylomyces* spp, *Pilaira* spp., *Rhizomucor* spp., *Rhizopus* spp., or *Zygomycetes* spp.), and phylum Oomycota in the Stramenopila kingdom) by between 1% and 100% (e.g., 1%, 5%, 10%, 20%, 30%, 40%, 50%, 60%, 70%, 80%, 90%, 95%, 99%, or 100%) causing lysis of the pathogen and cell growth inhibition. Alternatively, a physician may monitor the responsiveness of a subject (e.g., a human) to treatment with an AMP described herein using established procedures. The responsiveness of the infecting pathogen (e.g., a bacteria or fungus) to the AMPs described herein may be monitored in vitro, wherein a sample of the pathogen is taken and grown in a laboratory setting in various concentrations of the AMP, (see, e.g., examples 11, 12, 14, and 16). Inhibition of cell growth, and the observations of the subject by a physician skilled in the art, will be indicate the responsiveness of the infection to the AMP.

Further, the AMPs described herein are capable of reducing an infection by an ESKAPE pathogen, commonly associated with antimicrobial resistance (e.g., *Enterococcus faecium*, *Staphylococcus aureus*, *Klebsiella pneumoniae*, *Acinetobacter baumannii*, *Pseudomonas aeruginosa*, *Enterobacter*) by between 1% and 100% (e.g., 1%, 5%, 10%, 20%, 30%, 40%, 50%, 60%, 70%, 80%, 90%, 95%, 99%, or 100%).

The AMPs described herein may be capable of reducing an infection by a fungus. The fungus may be a mold from phylum Ascomycota (e.g., *Ajellomyces* spp., *Alternaria* spp., *Aschersonia* spp., *Aspergillus* spp., *Arthroderma* spp., *Ascochyta* spp., *Bipolaris* spp., *Blastomyces* spp., *Botryotinia* spp., *Chaetomium* spp., *Cladosporium* spp., *Coccidioides* spp., *Curvularia* spp., *Emericella* spp., *Emmonsia* spp., *Epicoccum* spp., *Exophiala* spp., *Fusarium* spp., *Geomyces* spp., *Geotrichum* spp., *Gibberella* spp., *Histoplasma* spp., *Magnaporthe* spp., *Metarhizium* spp., *Monascus* spp., *Mycospaerella* spp., *Nectria* spp., *Neosartorya* spp., *Neurospora* spp., *Paecilomyces* spp., *Paracoccidioides* spp., *Penicillium* spp., *Phaeosphaeria* spp., *Phialemonium* spp.,

*Podospora* spp., *Pyrenophora* spp., *Sclerotinia* spp., *Scopulariopsis* spp., *Sporothrix* spp., *Stachybotrys* spp., *Stemphylium* spp., *Talaromyces* spp., *Trichophyton* spp., *Trichothecium* spp., *Tricoderma* spp., *Tuber* spp., *Uncinocarpus* spp., or *Verticillium* spp.), phylum Basidomycota (e.g., *Moniliophthora* spp., *Sporobolomyces* spp., *Trichosporon* spp., *Ustilago* spp., *Cryptococcus* spp. or *Rhodotorula* spp.), phylum Chytridiomycota, phylum Zygomycota (e.g., *Absidia* spp., *Amylomyces* spp, *Pilaira* spp., *Rhizomucor* spp., *Rhizopus* spp., or *Zygomycetes* spp.), and phylum Oomycota in the Stramenopila kingdom by between 1% and 100% (e.g., 1%, 5%, 10%, 20%, 30%, 40%, 50%, 60%, 70%, 80%, 90%, 95%, 99%, or 100%).

Also featured are peptidomimetics of the AMPs described herein, which include chemically modified peptides, peptide-like molecules containing non-naturally occurring amino acids, peptoids and the like. The AMP peptidomimetics retain the characteristics of antimicrobial peptides described herein, having antimicrobial activity. In particular, an AMP peptidomimetic retains the cytotoxicity and/or cytostatic properties of the peptide from which it is derived (e.g., activity against, e.g., a bacterial cell (e.g., *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *B. cepacia*, *Citrobacter freundii*, *Citrobacter koseri*, *Clostridium clostridioforme*, *Clostridium perfringens*, *C. sordellii*, *Enterobacter aerogenes*, *Enterobacter cloacae*, *Enterococcus faecalis*, *Enterococcus* spp. (vancomycin susceptible and resistant isolates), *Escherichia coli* (including ESBL and KPC producing isolates), *Eubacterium lentum*, *Fusobacterium* spp., *Haemophilus influenzae* (including beta-lactamase positive isolates), *Haemophilus parainfluenzae*, *Klebsiella pneumoniae* (including ESBL and KPC producing isolates), *Klebsiella oxytoca* (including ESBL and KPC producing isolates), *Legionella pneumophila*, *Moraxella catarrhalis*, *Morganella morganii*, *Mycoplasma* spp., *Peptostreptococcus* spp., *Porphyromonas saccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus* (methicillin susceptible and resistant isolates), *Staphylococcus epidermidis* (methicillin susceptible and resistant isolates), *Stenotrophomonas maltophilia*, *Streptococcus agalactiae*, *Streptococcus constellatus*, *Streptococcus pneumoniae* (penicillin susceptible and resistant isolates), *Streptococcus pyogenes*, or *Streptococcus pyogenes*), or a fungus (e.g., a mold pathogen, such as one from the phylum Ascomycota (e.g., *Ajellomyces* spp., *Alternaria* spp., *Aschersonia* spp., *Aspergillus* spp., *Arthroderma* spp., *Ascochyta* spp., *Bipolaris* spp., *Blastomyces* spp., *Botryotinia* spp., *Chaetomium* spp., *Cladosporium* spp., *Coccidioides* spp., *Curvularia* spp., *Emericella* spp., *Emmonsia* spp., *Epicoccum* spp., *Exophiala* spp., *Fusarium* spp., *Geomyces* spp., *Geotrichum* spp., *Gibberella* spp., *Histoplasma* spp., *Magnaporthe* spp., *Metarhizium* spp., *Monascus* spp., *Mycospaerella* spp., *Nectria* spp., *Neosartorya* spp., *Neurospora* spp., *Paecilomyces* spp., *Paracoccidioides* spp., *Penicillium* spp., *Phaeosphaeria* spp., *Phialemonium* spp., *Podospora* spp., *Pyrenophora* spp., *Sclerotinia* spp., *Scopulariopsis* spp., *Sporothrix* spp., *Stachybotrys* spp., *Stemphylium* spp., *Talaromyces* spp., *Trichophyton* spp., *Trichothecium* spp., *Tricoderma* spp., *Tuber* spp., *Uncinocarpus* spp., or *Verticillium* spp.), phylum Basidomycota (e.g., *Moniliophthora* spp., *Sporobolomyces* spp., *Trichosporon* spp., *Ustilago* spp., *Cryptococcus* spp. or *Rhodotorula* spp.), phylum Chytridiomycota, phylum Zygomycota (e.g., *Absidia* spp., *Amylomyces* spp, *Pilaira* spp., *Rhizomucor* spp., *Rhizopus* spp., or *Zygomycetes* spp.), and phylum Oomycota in the Stramenopila kingdom). In addition, the AMP peptidomimetic exhibits microbial specificity in the presence of eukaryotic cells (e.g., erythrocytes). Thus, AMPs and peptidomimetics thereof exhibit low or insignificant specificity or activity against mammalian cells.

Also featured are AMPs or analogs thereof having substantially the same effect as the AMPs described herein. Such AMPs include, but are not limited to, a substitution, addition, or deletion mutant of the AMPs described herein (e.g., in which one or two amino acids of the AMPs (e.g., the AMPs of SEQ ID NOs: 19-42) are substituted with another amino acid, are deleted, or in which one or two amino acids are added to the polypeptides). Also encompassed are peptides that are substantially homologous to the polypeptides. A variety of sequence alignment software programs are available in the art to facilitate determination of homology or equivalence of any protein to a protein of the invention.

In some AMPs described herein, D-amino acids may be used instead of or in addition to L-amino acids. Glycine does not have chirality due to two hydrogens. However, all other amino acids may be D-amino acids, including D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, AND D-VAL. In particular, one or more of the amino acids of the AMPs may be substituted with a D-amino acid.

The AMPs disclosed herein are a unique hybrid group of AMPs identified by their ability to solubilize cellular membranes of pathogens (e.g., bacterial pathogens, such as *P. aeruginosa* and *E. coli*, and fungal pathogens) in the presence of excess human biological samples (e.g., red blood cells, serum) and by their specificity for pathogen cellular membranes and low cytotoxicity to mammalian cells, such as red blood cells. AMPs are attractive drug candidates because of their potent antibacterial activity and low propensity for eliciting antibiotic resistant bacterial phenotypes. Further, the AMPs described herein were rationally designed to be active against pathogens even in the presence of eukaryotic cells, and to have a specificity for bacterial pathogens over eukaryotic cells.

Polynucleotides

The invention also features polynucleotides that encode the polypeptides described herein (e.g., peptides having 85% identity to one or more of the peptides listed in Table 1 or Table 3 (e.g., peptides of SEQ ID NOs: 1-10 and 19-42)). The term polynucleotide is used broadly and refers to polymeric nucleotides of any length (e.g., oligonucleotides, genes, small inhibiting RNA, fragments of polynucleotides encoding a protein, etc.). By way of example and not limitation, the polynucleotides of the invention may have a sequence encoding all or part of a CPP or AMP (e.g., the peptides of Table 1 and Table 3, respectively, and peptides having at least 85% sequence identity thereto (e.g., over at least 5, 10, or more amino acids (e.g., over the entire amino acid sequence))). The polynucleotide described herein may be, for example, linear, circular, supercoiled, single-stranded, double-stranded, branched, partially double-stranded or partially single-stranded. The nucleotides of the polynucleotide may be naturally occurring nucleotides or modified nucleotides.

Polynucleotides described herein encode for CPPs that exhibit one or more of the following characteristics: a fold increase over 15× and up to 1000× (e.g., 20×, 25×, 30×, 35×, 40×, 50×, 70×, 90×, 100×, 150×, 200×, 250×, 300×, 350×, 400×, 450×, 500×, 550×, 600×, 650×, 700×, 750×, 800×, 850×, 900×, 950×, 999×) efficiency in cellular membrane penetration over Tat or penetratin (SEQ ID NOs: 1 and 2, respectively), or the ability to internalize a cargo (e.g., a compound) with a fold increase over 15× and up to 1000× (e.g., 20×, 25×, 30×, 35×, 40×, 50×, 70×, 90×, 100×, 150×, 200×, 250×, 300×, 350×, 400×, 450×, 500×, 550×, 600×, 650×, 700×, 750×, 800×, 850×, 900×, 950×, 999×) efficiency in cellular membrane penetration over Tat or penetratin (SEQ ID NOs: 1 and 2, respectively).

Polynucleotides described herein encode for AMPs that maintain activity against microbial pathogens (e.g., fungal (e.g., yeast or mold), and bacterial infection) in the presence of eukaryotic cells, and decreased hemolytic activity and toxicity against eukaryotic cells.

Polynucleotide sequences that encode peptide variants within 85% sequence identity to any one of SEQ ID NOs: 1-10 and 19-42, having the characteristics of CPPs or AMPs described herein, may also be identified by methods known in the art. A variety of sequence alignment software programs are available to facilitate determination of homology or equivalence. Non-limiting examples of these programs are BLAST family programs including BLASTN, BLASTP, BLASTX, TBLASTN, and TBLASTX (BLAST is available from the worldwide web at ncbi.nlm.nih.gov/BLAST/), FastA, Compare, DotPlot, BestFit, GAP, FrameAlign, ClustalW, and PileUp. Other similar analysis and alignment programs can be purchased from various providers, such as DNA Star's MegAlign, or the alignment programs in Gene-Jockey. Alternatively, sequence analysis and alignment programs can be accessed through the World Wide Web at sites such as the CMS Molecular Biology Resource at sdsc.edu-fResTools/cmshp.html and ExPASy Proteomics Server at www.expasy.org/. Any sequence database that contains DNA or protein sequences corresponding to a gene or a segment thereof can be used for sequence analysis. Commonly employed databases include but are not limited to GenBank, EMBL, DDBJ, PDB, SWISS-PROT, EST, STS, GSS, and HTGS.

Parameters for determining the extent of homology set forth by one or more of the aforementioned alignment programs are well established in the art. They include but are not limited to p value, percent sequence identity and the percent sequence similarity. P value is the probability that the alignment is produced by chance. For a single alignment, the p value can be calculated according to Karlin et al., *Proc. Natl. Acad. Sci.* (*USA*) 87: 2246, 1990. For multiple alignments, the p value can be calculated using a heuristic approach such as the one programmed in BLAST. Percent sequence identify is defined by the ratio of the number of nucleotide or amino acid matches between the query sequence and the known sequence when the two are optimally aligned. The percent sequence similarity is calculated in the same way as percent identity except one scores amino acids that are different but similar as positive when calculating the percent similarity. Thus, conservative changes that occur frequently without altering function, such as a change from one basic amino acid to another or a change from one hydrophobic amino acid to another are scored as if they were identical.

Expression Vectors

Also featured are expression vectors containing at least one polynucleotide encoding a peptide of the invention or fragment thereof (e.g., a fragment that retains the ability to penetrate a cellular membrane, or a fragment of an AMP that retains activity against pathogens (e.g., in the presence of eukaryotic cells, such as red blood cells). For example, an expression vector includes a polynucleotide encoding one or more of the peptides of Table 1 or Table 3 and variants thereof having at least 85% sequence identity thereto. Furthermore, an expression vector can include polynucleotides encoding a peptide conjugate containing one or more of the peptides of Table 1, any fragments, variants, or derivatives thereof, and a polypeptide linked to the peptide of Table 1. Expression vectors are well known in the art and include, but are not limited to viral vectors and plasmids. Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127), adenovirus vectors, alphavirus-based vectors (e.g., Sindbis virus vectors, Semliki forest virus), Ross River virus, adeno-associated virus (AAV) vectors (see, e.g., PCT Publication Nos. WO 94/12649, WO 93/03769; WO 93/19191; WO 94/28938; WO 95/11984 and WO 95/00655), vaccinia virus (e.g., Modified Vaccinia virus Ankara (MVA) or fowlpox), Baculovirus recombinant system, and herpes virus.

Nonviral vectors, such as plasmids, are also well known in the art and include, but are not limited to prokaryotic and eukaryotic vectors (e.g., yeast- and bacteria-based plasmids), as well as plasmids for expression in mammalian cells. Methods of introducing the vectors into a host cell and isolating and purifying the expressed protein are also well known in the art (e.g., *Molecular Cloning: A Laboratory Manual*, second edition, Sambrook, et al., 1989, Cold Spring Harbor Press). Examples of host cells include, but are not limited to, mammalian cells, such as NS0, CHO cells, HEK and COS, and bacterial cells, such as *E. coli*.

By way of example, vectors containing the polynucleotide of the CPPs or AMPs described herein may further contain a tag polynucleotide sequence to facilitate protein isolation and/or purification. Examples of tags include but are not limited to the myc-epitope, S-tag, his-tag, HSV epitope, V5-epitope, FLAG and CBP (calmodulin binding protein). Such tags are commercially available or readily made by methods known to the art.

The vector may further include a polynucleotide sequence encoding a linker sequence. Generally the linking sequence is positioned in the vector between the CPP-encoding polynucleotide sequence and the polynucleotide tag sequence. Linking sequences can encode random amino acids or can contain functional sites. Examples of linking sequences containing functional sites include but are not limited to, sequences containing the Factor Xa cleavage site, the thrombin cleavage site, or the enterokinase cleavage site.

By way of example, and not limitation, a CPP or AMP may be generated as described herein using mammalian expression vectors in mammalian cell culture systems or bacterial expression vectors in bacterial culture systems. Primers may be used to amplify the desired sequence from a template.

Methods of Manufacture

The CPPs and AMPs described herein can be prepared by chemical peptide synthesis, such as by coupling different amino acids to each other through chemical conjugation. Chemical peptide synthesis is particularly suitable for the inclusion of, e.g., D-amino acids, amino acids with non-naturally occurring side chains, and natural amino acids with modified side chains, such as methylated cysteine. Chemical peptide synthesis methods are well known in the art. Peptide synthesis can be performed as solid phase peptide synthesis (SPPS) or contrary to solution phase peptide synthesis. The best known SPPS methods are T-Boc and Fmoc solid phase chemistry which is amply known to the skilled person. In addition, peptides can be linked to one other to form longer peptides using a ligation strategy (chemo selective coupling of two unprotected peptide fragments) as originally described by Kent (Schnolzer & Kent (1992) *Int. J. Pept. Protein Res.* 40, 190-193) and reviewed, for example, in Tam et al (2001) *Biopolymers* 60, 194-205. This provides the potential to achieve protein synthesis beyond the scope of SPPS. Many proteins with the size of 100-300 residues have been synthesized successfully by this method. Synthetic peptides have continued to play an ever increasing role in the research fields of biochemistry, pharmacology, neurobiology, enzymology, and molecular biology because of the advances in SPPS.

For recombinant production, one or more polynucleotides encoding the CPP, CPP-conjugate (e.g., a CPP linked to a peptide, polypeptide, or protein), AMP, or any fragment or variant or derivative thereof, can be inserted into one or more vectors for further cloning and/or expression in a host cell. Such polynucleotides may be readily isolated and sequenced using conventional procedures. For expression, a vector (e.g., an expression vector) containing one or more of the polynucleotides of the invention is provided. Methods which are well known to those skilled in the art can be used to construct expression vectors containing the coding sequence of the CPP, CPP-conjugate, AMP, or any fragment or variant or derivative thereof, along with appropriate transcriptional/translational control signals. These methods include in vitro recombinant DNA techniques, synthetic techniques, and in vivo recombination/genetic recombination. See, for example, the techniques described in Maniatis et al., *Molecular Cloning: A Laboratory Manual*, Cold Spring Harbor Laboratory, N.Y. (1989); and Ausubel et al., Current Protocols in Molecular Biology, Greene Publishing Associates and Wiley Interscience, N.Y. (1989). The expression vector can be part of a plasmid, virus, or can be a nucleic acid fragment. The expression vector includes an expression cassette into which the polynucleotide encoding the CPP, CPP-conjugate (e.g., a CPP linked to a peptide, polypeptide, or protein), AMP, or any fragment or variant or derivative thereof, (e.g., the coding region) is cloned into operable association with a promoter and or other transcription control elements. Two or more coding regions can be present in a single polynucleotide construct, e.g., on a single vector, or in separate polynucleotide constructs, e.g., on separate (different) vectors. Furthermore, any vector may contain a single coding region, or can have two or more coding regions, e.g., a vector described herein can encode one or more polypeptides, which are post- or co-translationally separated into the final polypeptide via proteolytic cleavage. In addition, a vector, polynucleotide, or nucleic acid described herein can contain heterologous coding regions, either fused or unfused to a polynucleotide encoding the CPP, CPP-conjugate (e.g., a CPP linked to a peptide, polypeptide, or protein), AMP, or any fragment or variant or derivative thereof. Heterologous coding regions include, for example, specialized elements or motifs, such as a secretory signal peptide or heterologous functional domain. An operable association is when a coding region for a gene product, (e.g., a polypeptide), is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that polynucleic acid. The promoter may be a cell-specific promoter that directs substantial transcription of the DNA only in predetermined cells. Other transcription control elements, besides a promoter, for example, are enhancers, operators, repressors, and transcription termination signals, can be operably associated with the polynucleotide to direct cell-specific transcription. A variety of transcription control regions are known to those skilled in the art. Examples of transcription control regions, which function in vertebrate cells, such as, but not limited to, promoter enhancer segments from cytomegaloviruses (e.g., the immediate early promoter, in conjunction with intron-A), simian virus 40 (e.g., the early promoter), and retroviruses (e.g., Rous sarcoma virus). Other transcription control regions include those derived from vertebrate genes such as actin, heat shock protein, bovine growth hormone and rabbit alpha-globin, as well as other sequences capable of controlling gene expression in eukaryotic cells. Additional suitable transcription control regions include tissue-specific promoters and enhancers as well as inducible promoters (e.g., promoter inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Once a CPP, CPP conjugate, or AMP, or any fragments thereof has been produced by recombinant expression, it can be purified by any method known in the art for purification of a peptide molecule, for example, by chromatography (e.g., ion exchange, affinity, and sizing column chromatography), centrifugation, differential solubility, or by any other standard technique for the purification of proteins. Further, the CPP, CPP conjugate, or AMP, or any fragments thereof can be fused to heterologous polypeptide sequences described herein or otherwise known in the art to facilitate purification or to produce therapeutic peptide.

Once isolated, a CPP, or CPP conjugate, or AMP, or any fragments thereof can, if desired, be further purified, e.g., by high performance liquid chromatography (see, e.g., Fisher, Laboratory Techniques in Biochemistry and Molecular Biology (Work and Burdon, eds., Elsevier, 1980); the disclosure of which is incorporated herein by reference), or by gel filtration chromatography, such as on a Superdex™ 75 column (Pharmacia Biotech AB, Uppsala, Sweden). Similar purification steps can be taken for CPPs, CPP conjugates, or AMPs, or any fragments thereof, produced through chemical peptide synthesis. Once cleaved form the resin, the isolated CPP, CPP conjugate, or AMP, or any fragment thereof, may be further purified as described above.

Methods of Conjugation

The CPPs described herein and manufactured as described above, by either chemical or recombinant methods, may be isolated and purified by methods known in the art. The isolated or purified peptides may further be conjugated to a cargo. For example, the cargo can be a compound, such as a small molecule, macromolecule (e.g., a peptide, a polypeptide, a protein, a nucleic acid, a polynucleic acid, a peptide nucleic acid, a poly nucleic acid analog, an antibody, a polymer, bioactive peptide, or any fragments thereof), or a fluorescent molecule, such as one or more of the agents described in Table 2 or herein. The compounds can be conjugated directly to the CPP described herein, or through a linker. The compound can be conjugated by a covalent bond. Covalent conjugation of a peptide and one or more compounds, either directly or through a linker, may be accomplished using well-known organic chemical synthesis techniques and methods or, if the conjugated cargo is a protein, the conjugate can be prepared by recombinant expression techniques as described herein. If prepared by chemical synthesis, complementary functional groups on the two components may react with each other to form a covalent bond. By way of example, and not limitation, complementary reactive functional groups include maleimide and cysteine, amide and activated carboxylic acid, thiol and maleimide, activated sulfonic acid and amine, isocyanate and amine, azide and alkyne, and alkene and tetrazine.

Other examples of functional groups capable of reacting with amino groups include, alkylating and acylating agents. Representative alkylating agents include: (i) an α-haloacetyl group (e.g., $XCH_2CO-$ (where X=Br, Cl, or I); (ii) a N-maleimide group, which may react with amino groups either through a Michael type reaction or through acylation by addition to the ring carbonyl group; (iii) an aryl halide (e.g., a nitrohaloaromatic group); (iv) an alkyl halide; (v) an aldehyde or ketone capable of Schiff's base formation with amino groups; (vi) an epoxide (e.g., an epichlorohydrin and a bisoxirane, which may react with amino, sulfhydryl, or phenolic hydroxyl groups; (vii) a chlorine-containing s-triazine, which is reactive towards nucleophiles such as amino, sulfhydryl, and hydroxyl groups; (viii) an aziridine, which is reactive towards nucleophiles such as amino groups by ring opening; (ix) a squaric acid diethyl ester; and (x) an α-haloalkyl ether.

Amino-reactive acylating groups include, e.g., (i) an isocyanate and isothiocyanate; (ii) a sulfonyl chloride; (iii) an acid halide; (iv) an active ester (e.g., a nitrophenylester of N-hydroxysuccinimidyl ester); (v) an acid anhydride (e.g., a mixed, symmetrical, or N-carboxyanhydride); (vi) an acylazide; and (vii) an imidoester. Aldehydes and ketones may be reacted with amines to form Schiff's bases, which may be stabilized through reductive amination.

It will be appreciated that certain functional groups may be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

Pharmaceutical Compositions

The polynucleotides, polypeptides, polypeptide conjugates, and antimicrobial peptides described herein can be prepared as compositions that contain a pharmaceutically acceptable carrier, excipient, or stabilizer known in the art (*Remington: The Science and Practice of Pharmacy* 20th Ed., 2000, Lippincott Williams and Wilkins, Ed. K. E. Hoover), in the form of a lyophilized formulation, or as an aqueous solution. Acceptable carriers, excipients, or stabilizers are non-toxic to recipients at the employed dosages and concentrations, and may include buffers such as phosphate, citrate, and other organic acids; antioxidants including ascorbic acid and methionine; preservatives (e.g., octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol); low molecular weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, marmose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

The compositions (e.g., when used in the methods described herein) generally include, by way of example and not limitation, an effective amount (e.g., an amount sufficient to mitigate disease, alleviate a symptom of disease and/or prevent or reduce the progression of disease) of a CPP conjugate or polynucleotide encoding the CPP-conjugate (e.g., a conjugate containing one or more of the CPPs of Table 1, a polynucleotide encoding the CPP, and variants thereof having at least 85% sequence identity thereto, and analogs thereof).

For example, the compositions can be formulated to include between about 1 μg/mL and about 1 g/mL of the CPP, CPP-conjugate, or AMP (e.g., between 10 μg/mL and 300 μg/mL, 20 μg/mL and 120 μg/mL, 40 μg/mL and 200 μg/mL, 30 μg/mL and 150 μg/mL, 40 μg/mL and 100 μg/mL, 50 μg/mL and 80 μg/mL, or 60 μg/mL and 70 μg/mL, or 10 mg/mL and 300 mg/mL, 20 mg/mL and 120 mg/mL, 40 mg/mL and 200 mg/mL, 30 mg/mL and 150 mg/mL, 40 mg/mL and 100 mg/mL, 50 mg/mL and 80 mg/mL, or 60 mg/mL and 70 mg/mL of the CPP, CPP-conjugate, or AMP).

The pharmaceutical composition can further include an additional agent that serves to enhance and/or complement the desired effect. By way of example, to enhance the efficacy of the one or more CPP-conjugates or fragments or combinations thereof, administered as a pharmaceutical composition, the pharmaceutical composition may further contain an adjuvant.

Also by way of example and not limitation, if the one or more CPPs, CPP conjugates, or fragments or combinations thereof of the invention is being administered to augment the immune response in a subject with cancer or suspected of having cancer, the composition can further include a therapeutic agent (e.g., anti-cancer, and/or immunotherapy agent). Examples of immunotherapy agents include, e.g., an anti-CTLA-4 agent, an anti-PD-1 agent, an anti-PD-L1 agent, an anti-PD-L2 agent, a TNF-α cross-linking agent, a TRAIL cross-linking agent, an anti-CD27 agent, an anti-CD30 agent, an anti-CD40 agent, an anti-4-1 BB agent, an anti-GITR agent, an anti-OX40 agent, an anti-TRAILR1 agent, an anti-TRAILR2 agent, an anti-TWEAKR agent, an anti-TWEAK agent, an anti-cell surface lymphocyte protein agent, an anti-BRAF agent, an anti-MEK agent, an anti-CD33 agent, an anti-CD20 agent, an anti-HLA-DR agent, an anti-HLA class I agent, an anti-CD52 agent, an anti-A33 agent, an anti-GD3 agent, an anti-PSMA agent, an anti-Ceacan 1 agent, an anti-Galedin 9 agent, an anti-HVEM agent, an anti-VISTA agent, an anti-B7 H4 agent, an anti-HHLA2 agent, an anti-CD155 agent, an anti-CD80 agent, an anti-BTLA agent, an anti-CD160 agent, an anti-CD28 agent, an anti-CD226 agent, an anti-CEACAM1 agent, an anti-TIM3 agent, an anti-TIGIT agent, an anti-CD96 agent, an anti-CD70 agent, an anti-CD27 agent, an anti-LIGHT agent, an anti-CD137 agent, an anti-DR4 agent, an anti-CR5 agent, an anti-TNFRS agent, an anti-TNFR1 agent, an anti-FAS agent, an anti-CD95 agent, an anti-TRAIL agent, an anti-DR6 agent, an anti-EDAR agent, an anti-NGFR agent, an anti-OPG agent, an anti-RANKL agent, an anti-LTβ receptor agent, an anti-BCMA agent, an anti-TACI agent, an anti-BAFFR agent, an anti-EDAR2 agent, an anti-TROY agent, or an anti-RELT agent. For example, the immunotherapy agent may be an anti-CTLA-4 antibody or antigen-binding fragment thereof, an anti-PD-1 antibody or antigen-binding fragment thereof, an anti-PD-L1 antibody or antigen-binding fragment thereof, an anti-PD-L2 antibody or antigen-binding fragment thereof, a TNF-α cross-linking antibody or antigen-binding fragment thereof, a TRAIL cross-linking antibody or antigen-binding fragment thereof, an anti-CD27 antibody or antigen-binding fragment thereof, an anti-CD30 antibody or antigen-binding fragment thereof, an anti-CD40 antibody or antigen-binding fragment thereof, an anti-4-1 BB antibody or antigen-binding fragment thereof, an anti-GITR antibody or antigen-binding fragment thereof, an anti-OX40 antibody or antigen-binding fragment thereof, an anti-TRAILR1 antibody or antigen-binding fragment thereof, an anti-TRAILR2 antibody or antigen-binding fragment thereof, an anti-TWEAKR antibody or antigen-binding fragment thereof, an anti-TWEAK antibody or antigen-binding fragment thereof, an anti-cell surface lymphocyte protein antibody or antigen-binding fragment thereof, an anti-BRAF antibody or antigen-binding fragment thereof, an anti-MEK antibody or antigen-binding fragment thereof, an anti-CD33 antibody or antigen-binding fragment thereof, an anti-CD20 antibody or antigen-binding fragment thereof, an anti-HLA-DR antibody or antigen-binding fragment thereof, an anti-HLA class I antibody or antigen-binding fragment thereof, an anti-CD52 antibody or antigen-binding fragment thereof, an anti-A33 antibody or antigen-binding fragment thereof, an anti-GD3 antibody or antigen-binding fragment thereof, an anti-PSMA antibody or antigen-binding fragment thereof, an anti-Ceacan 1 antibody or antigen-binding fragment thereof, an anti-Galedin 9 antibody or antigen-binding fragment thereof, an anti-HVEM antibody or antigen-binding fragment thereof, an anti-VISTA antibody or antigen-binding fragment thereof, an anti-B7 H4 antibody or antigen-binding fragment thereof, an anti-HHLA2 antibody or antigen-binding fragment thereof, an anti-CD155 antibody or antigen-binding fragment thereof, an anti-CD80 antibody or antigen-binding fragment thereof, an anti-BTLA antibody or antigen-binding fragment thereof, an anti-CD160 antibody or antigen-binding fragment thereof, an anti-CD28 antibody or antigen-binding fragment thereof, an anti-CD226 antibody or antigen-binding fragment thereof, an anti-CEACAM1 antibody or antigen-binding fragment thereof, an anti-TIM3 antibody or antigen-binding fragment thereof, an anti-TIGIT antibody or antigen-binding fragment thereof, an anti-CD96 antibody or antigen-binding fragment thereof, an anti-CD70 antibody or antigen-binding fragment thereof, an anti-CD27 antibody or antigen-binding fragment thereof, an anti-LIGHT antibody or antigen-binding fragment thereof, an anti-CD137 antibody or antigen-binding fragment thereof, an anti-DR4 antibody or antigen-binding fragment thereof, an anti-CR5 antibody or antigen-binding fragment thereof, an anti-TNFRS antibody or antigen-binding fragment thereof, an anti-TNFR1 antibody or antigen-binding fragment thereof, an anti-FAS antibody or antigen-binding fragment thereof, an anti-CD95 antibody or antigen-binding fragment thereof, an anti-TRAIL antibody or antigen-binding fragment thereof, an anti-DR6 antibody or antigen-binding fragment thereof, an anti-EDAR antibody or antigen-binding fragment thereof, an anti-NGFR antibody or antigen-binding fragment thereof, an anti-OPG antibody or antigen-binding fragment thereof, an anti-RANKL antibody or antigen-binding fragment thereof, an anti-LTβ receptor antibody or antigen-binding fragment thereof, an anti-BCMA antibody or antigen-binding fragment thereof, an anti-TACI antibody or antigen-binding fragment thereof, an anti-BAFFR antibody or antigen-binding fragment thereof, an anti-EDAR2 antibody or antigen-binding fragment thereof, an anti-TROY antibody or antigen-binding fragment thereof, or an anti-RELT antibody or antigen-binding fragment thereof. In some embodiments, the immunotherapy agent is an anti-cell surface lymphocyte protein antibody or antigen-binding fragment thereof, such as an antibody or antigen-binding fragment thereof that binds one or more of CD1, CD2, CD3, CD4, CD5, CD6, CD7, CD8, CD9, CD10, CD11, CD12, CD13, CD14, CD15, CD16, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49, CD50, CD51, CD52, CD53, CD54, CD55, CD56, CD57, CD58, CD59, CD60, CD61, CD62, CD63, CD64, CD65, CD66, CD67, CD68, CD69, CD70, CD71, CD72, CD73, CD74, CD75, CD76, CD77, CD78, CD79, CD80, CD81, CD82, CD83, CD84, CD85, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD108, CD109, CD110, CD111, CD112, CD113, CD114, CD115, CD116, CD117, CD118, CD119, CD120, CD121, CD122, CD123, CD124, CD125, CD126, CD127, CD128, CD129, CD130, CD131, CD132, CD133, CD134, CD135, CD136, CD137, CD138, CD139, CD140, CD141, CD142, CD143, CD144, CD145, CD146, CD147, CD148, CD149, CD150, CD151, CD152, CD153, CD154, CD155, CD156, CD157, CD158, CD159, CD160, CD161, CD162, CD163, CD164, CD165, CD166, CD167, CD168, CD169, CD170, CD171, CD172, CD173, CD174, CD175, CD176, CD177, CD178, CD179, CD180, CD181, CD182, CD183, CD184, CD185, CD186, CD187, CD188, CD189, CD190, CD191, CD192, CD193, CD194, CD195, CD196, CD197, CD198, CD199, CD200, CD201, CD202, CD203, CD204, CD205, CD206, CD207, CD208, CD209, CD210, CD211, CD212, CD213, CD214, CD215, CD216, CD217, CD218, CD219, CD220, CD221, CD222, CD223, CD224, CD225, CD226, CD227, CD228, CD229, CD230, CD231, CD232, CD233, CD234, CD235, CD236, CD237, CD238, CD239, CD240, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CD293, CD294, CD295, CD296, CD297, CD298, CD299, CD300, CD301, CD302, CD303, CD304, CD305, CD306, CD307, CD308, CD309, CD310, CD311, CD312, CD313, CD314, CD315, CD316, CD317, CD318, CD319, and/or CD320.

In some embodiments, the immunotherapy agent is an agent (e.g., a polypeptide, antibody, antigen-binding fragment thereof, a single-chain polypeptide, or construct) that binds a chemokine or lymphokine, such as a chemokine or lymphokine involved in tumor growth. For instance, the immunotherapy agent may be an agent (e.g., polypeptide, antibody, antigen-binding fragment thereof, single-chain polypeptide, or construct) that bind and inhibits the activity of one or more, or all, of CXCL1, CXCL2, CXCL3, CXCL8, CCL2 and CCL5. In some embodiments, the immunotherapy agent is an agent (e.g., a polypeptide, antibody, antigen-binding fragment thereof, a single-chain polypeptide, or construct) that binds and inhibits the activity of one or more, or all, of CCL3, CCL4, CCL8, and CCL22.

The immunotherapy agent may be capable of specifically binding one or more of the immunological targets described in Table 1 of Mahoney et al., *Cancer Immunotherapy*, 14:561-584 (2015), the disclosure of which is incorporated herein by reference in its entirety. For example, the immunotherapy agent may be an agent, such as an antibody or antigen-binding fragment thereof, that specifically binds one or more of OX40L, TL1A, CD40L, LIGHT, BTLA, LAGS, TIM3, Singlecs, ICOS, B7-H3, B7-H4, VISTA, TMIGD2, BTNL2, CD48, KIR, LIR, LIR antibody, ILT, NKG2D, NKG2A, MICA, MICB, CD244, CSF1R, IDO, TGFβ, CD39, CD73, CXCR4, CXCL12, SIRPA, CD47, VEGF, or neuropilin. In particular, the immunotherapy agent is an anti-PD-1 or anti-PDL1 antibody.

Additional examples of immunotherapy agents include, e.g., Targretin, Interferon-alpha, clobestasol, Peg Interferon (e.g., PEGASYS®), prednisone, Romidepsin, Bexarotene, methotrexate, Trimcinolone cream, anti-chemokines, Vorinostat, gabapentin, antibodies to lymphoid cell surface receptors and/or lymphokines, antibodies to surface cancer proteins, and/or small molecular therapies like Vorinostat.

A pharmaceutical composition of AMP may include a second antimicrobial agent. The second antimicrobial agent may be an antifungal agent. Antifungal agents that can be used with the AMPs described herein include those that are standardly used by medical professionals in the treatment of candidiasis including, for example, an azole (e.g., a triazole, such as fluconazole, albaconazole, efinaconazole, epoxiconazole, isavuconazole, itraconazole, posaconazole, propiconazole, ravuconazole, terconazole, and voriconazole; an imidazole, such as bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, and tioconazole; and a thiazole, such as abafungin), a polyene (e.g., amphotericin B, candicidin, filipin, hamycin, natamycin, nystatin, and rimocidin), an allylamine (e.g., amorolfin, butenafine, naftifine, and terbinafine), an echinocandin (e.g., anidulafungin, biafungin (e.g., CD101), caspofungin, and micafungin), lanosterol demethylase inhibitors (e.g., VT-1161) and other antifungal agents, including, but not limited to, benzoic acid, ciclopirox olamine, enfumafungin (e.g., SCY-078), 5-flucytosin, griseofulvin, haloprogin, tolnaftate, aminocandin, chlordantoin, chlorphenesin, nifuroxime, undecylenic acid, and crystal violet, and pharmaceutically acceptable salts or esters thereof.

The compositions (e.g., when used in the methods described herein) generally include, by way of example and not limitation, an effective amount (e.g., an amount sufficient to mitigate infection, and/or prevent or reduce the progression of the infection) of an AMP from Table 3, or any variants thereof having at least 85% sequence identity thereto, and analogs thereof).

The pharmaceutical composition can further include an additional agent that serves to enhance and/or complement the desired effect. By way of example, to enhance the efficacy of the one or more AMPs or fragments or combinations thereof, administered as a pharmaceutical composition, the pharmaceutical composition may further contain an antimicrobial or antifungal agent.

For example, as used herein, an antibacterial agent can be Afenide, Amikacin, Amoxicillin, Ampicillin, Arsphenamine, Augmentin, Azithromycin, Azlocillin, Aztreonam, Bacampicillin, Bacitracin, Balofloxacin, Besifloxacin, Capreomycin, Carbacephem (loracarbef), Carbenicillin, Cefacetrile (cephacetrile), Cefaclomezine, Cefaclor, Cefadroxil (cefadroxyl), Cefalexin (cephalexin), Cefaloglycin (cephaloglycin), Cefalonium (cephalonium), Cefaloram, Cefaloridine (cephaloradine), Cefalotin (cephalothin), Cefamandole, Cefaparole, Cefapirin (cephapirin), Cefatrizine, Cefazaflur, Cefazedone, Cefazolin (cephazolin), Cefcanel, Cefcapene, Cefclidine, Cefdaloxime, Cefdinir, Cefditoren, Cefedrolor, Cefempidone, Cefepime, Cefetamet, Cefetrizole, Cefivitril, Cefixime, Cefluprenam, Cefmatilen, Cefmenoxime, Cefmepidium, Cefmetazole, Cefodizime, Cefonicid, Cefoperazone, Cefoselis, Cefotaxime, Cefotetan, Cefovecin, Cefoxazole, Cefoxitin, Cefozopran, Cefpimizole, Cefpirome, Cefpodoxime, Cefprozil (cefproxil), Cefquinome, Cefradine (cephradine), Cefrotil, Cefroxadine, Cefsumide, Ceftaroline, Ceftazidime, Ceftazidime/Avibactam, Cefteram, Ceftezole, Ceftibuten, Ceftiofur, Ceftiolene, Ceftioxide, Ceftizoxime, Ceftobiprole, Ceftriaxone, Cefuracetime, Cefuroxime, Cefuzonam, Cephalexin, Chloramphenicol, Chlorhexidine, Ciprofloxacin, Clarithromycin, Clavulanic Acid, Clinafloxacin, Clindamycin, Cloxacillin, Colimycin, Colistimethate, Colistin, Crysticillin, Cycloserine 2, Demeclocycline, Dicloxacillin, Dirithromycin, Doripenem, Doxycycline, Efprozil, Enoxacin, Ertapenem, Erythromycin, Ethambutol, Flucloxacillin, Flumequine, Fosfomycin, Furazolidone, Gatifloxacin, Geldanamycin, Gemifloxacin, Gentamicin, Glycopeptides, Grepafloxacin, Herbimycin, Imipenem, Isoniazid, Kanamycin, Levofloxacin, Lincomycin, Linezolid, Lipoglycopeptides, Lomefloxacin, Meropenem, Meticillin, Metronidazole, Mezlocillin, Minocycline, Mitomycin, Moxifloxacin, Mupirocin, Nadifloxacin, Nafcillin, Nalidixic Acid, Neomycin, Netilmicin, Nitrofurantoin, Norfloxacin, Ofloxacin, Oxacillin, Oxazolidinones, Oxolinic Acid, Oxytetracycline, Oxytetracycline, Paromomycin, Pazufloxacin, Pefloxacin, Penicillin G, Penicillin V, Pipemidic Acid, Piperacillin, Piromidic Acid, Pivampicillin, Pivmecillinam, Platensimycin, Polymyxin B, Pristinamycin, Prontosil, Prulifloxacin, Pvampicillin, Pyrazinamide, Quinupristin/dalfopristin, Rifabutin, Rifalazil, Rifampin, Rifamycin, Rifapentine, Rosoxacin, Roxithromycin, Rufloxacin, Sitafloxacin, Sparfloxacin, Spectinomycin, Spiramycin, Streptomycin, Sulbactam, Sulfacetamide, Sulfamethizole, Sulfamethoxazole, Sulfanilimide, Sulfisoxazole, Sulphonamides, Sultamicillin, Teicoplanin, Telavancin, Telithromycin, Temafloxacin, Tetracycline, Thiamphenicol, Ticarcillin, Tigecycline, Tinidazole, Tobramycin, Tosufloxacin, Trimethoprim, Trimethoprim-Sulfamethoxazole, Troleandomycin, Trovafloxacin, Tuberactinomycin, Vancomycin, Viomycin, or pharmaceutically acceptable salts thereof, or a combination thereof.

Anti-fungal agents are known to the art. The art generally recognizes several categories of anti-fungal agents including (1) azoles (imidazoles), (2) antimetabolites, (3) allylamines, (4) morpholine, (5) glucan synthesis inhibitors (echinocandins), (6) polyenes, (7) benoxaaborale; (8) other antifungal/onychomycosis agents, and (9) new classes of antifungal/onychomycosis agents.

For example, as used herein, an anti-fungal agent can be Abafungin, Albaconazole, Amorolfin, Amphotericin B, Anidulafungin, Bifonazole, Butenafine, Butoconazole, Candicidin, Caspofungin, Ciclopirox, Clotrimazole, Econazole, Fenticonazole, Filipin, Fluconazole, Flucytosine, Griseofulvin, Haloprogin, Hamycin, Isavuconazole, Isoconazole, Itraconazole, Ketoconazole, Micafungin, Miconazole, Naftifine, Natamycin, Nystatin, Omoconazole, Oxiconazole, Polygodial, Posaconazole, Ravuconazole, Rimocidin, Sertaconazole, Sulconazole, Terbinafine, Terconazole, Tioconazole, Tolnaftate, Undecylenic Acid, Voriconazole, or pharmaceutically acceptable salts thereof, or a combination thereof.

Methods of Treatment

CPPs

Generally, a composition containing a CPP conjugated to a cargo (e.g., a compound, such as a therapeutic agent) can be administered (e.g., intravenously) to a subject (e.g., a patient in need thereof) as a medicament (e.g., for treating a medical condition). The CPP can be conjugated to a specific therapeutic agent (e.g., a hormone, a protein, an antibody, etc.) to treat a medical condition (e.g., those conditions described herein, such as diabetes, cancer, etc.). Non-limiting examples of therapeutic agents that can be conjugated to a CPP described herein for treatment of a medical condition are provided in Table 2.

For example, a CPP conjugate described herein may be administered to a subject in need thereof (e.g., a subject who has been diagnosed with a medical condition) by a variety of routes, such as local administration at or near the site affected by the medical condition (e.g., injection near a cancer, injection to a joint for treating rheumatoid arthritis, injection into the subretinal space for treating wet age-related macular degeneration, direct administration to the central nervous system (CNS) (e.g., intracerebral, intraventricular, intrathecal, intracisternal, or stereotactic administration) for treating a neurological medical condition, such as Parkinson's disease, direct injection into the cardiac muscle for treating cardiac infarction), intravenous, parenteral, intradermal, transdermal, intramuscular, intranasal, subcutaneous, percutaneous, intratracheal, intraperitoneal, intraarteial, intravascular, inhalation, perfusion, lavage, topical, and oral administration. The most suitable route for administration in any given case may depend on the particular CPP-conjugate or composition administered, the subject, pharmaceutical formulation methods, administration methods (e.g., administration time and administration route), the subject's age, body weight, sex, severity of the disease being treated, the subject's diet, and the subject's excretion rate. Compositions may be administered once, or more than once (e.g., once annually, twice annually, three times annually, bi-monthly, monthly). For local administration, CPP conjugates may be administered by any means that places the CPP conjugates in a desired location, including catheter, syringe, shunt, stent, microcatheter, pump, implantation with a device, or implantation with a scaffold.

Featured CPPs can promote the internalization of a cargo (e.g., a compound) into a tissue, organ, or living cell. Examples of a tissue, organ, or living cell are the liver or liver cells (e.g., hepatocytes), a kidney or kidney cell, a tumor or tumor cell, the CNS or CNS cells (central nervous system (e.g., brain and/or spinal cord), the PNS of PNS cells (Peripheral Nervous System), a lung or lung cells, the vasculature or vascular cells, the skin or skin cells (e.g., dermis cells and/or follicular cells), the eye or ocular cells (e.g., macula, fovea, cornea, retina), bone, gall bladder, spleen, small intestine, large intestine, stomach, pancreas, appendix, urinary bladder, heart or cardiac cells, and an ear or cells of the ear (e.g., cells of the inner ear, middle ear, and/or outer ear).

The CPP conjugates can be used to deliver a biologically active agent (e.g., a PNA which inhibits protein expression) to cells of the subject, such as cells of the immune system. CPP conjugates can also deliver a biologically active agent to liver cells (e.g., hepatocytes), or a tumor or tumor cells (e.g., a primary tumor or metastatic cancer cells), or to skin, adipose tissue, muscle tissue, and lymph nodes.

For delivery of a biologically active agent to the liver or liver cells, a composition containing a CPP conjugate described herein is contacted with the liver or liver cells of a subject as is generally known in the art, such as via parenteral administration (e.g., intravenous, intramuscular, subcutaneous administration) or local administration (e.g., direct injection, portal vein injection, catheterization, or stenting), to facilitate delivery.

For delivery of a biologically active agent to the kidney or kidney cells, a composition comprising a CPP conjugate described herein is contacted with the kidney or kidney cells of a subject as is generally known in the art, such as via parenteral administration (e.g., intravenous, intramuscular, or subcutaneous administration) or local administration (e.g., direct injection, catheterization, or stenting), to facilitate delivery.

For delivery of a biologically active agent to the tumor or tumor cells, a composition comprising a CPP conjugate described herein is contacted with the tumor or tumor cells of a subject as is generally known in the art, such as via parenteral administration (e.g., intravenous, intramuscular, or subcutaneous administration) or local administration (e.g., direct injection, catheterization, or stenting), to facilitate delivery.

For delivery of a biologically active agent to the CNS or CNS cells (e.g., brain cells and/or spinal cord cells), a composition comprising a CPP conjugate described herein is contacted with the CNS or CNS cells (e.g., brain cells and/or spinal cord cells) of a subject as is generally known in the art, to facilitate delivery.

For delivery of a biologically active agent to the PNS or PNS cells, a composition comprising a CPP conjugate described herein is contacted with the PNS or PNS cells of a subject as is generally known in the art, such as via parenteral administration (e.g., intravenous, intramuscular, or subcutaneous administration) or local administration (e.g., direct injection), to facilitate delivery.

For delivery of a biologically active agent to the lung or lung cells, a composition comprising a CPP conjugate described herein is contacted with the lung or lung cells of a subject as is generally known in the art, such as by inhalation or administration (e.g., pulmonary administration directly to lung tissue and cells), to facilitate delivery.

For delivery of a biologically active agent to the vasculature or vascular cells, a composition comprising a CPP conjugate described herein is contacted with the vasculature or vascular cells of the subject as is generally known in the art, such as via parenteral administration (e.g., intravenous, intramuscular, subcutaneous administration) or local administration (e.g., clamping, catheterization, or stenting), to facilitate delivery.

For delivery of a biologically active agent to the skin or skin cells (e.g., dermis cells and/or follicular cells), a composition comprising a CPP conjugate described herein is contacted with the skin or skin cells (e.g., dermis cells and/or follicular cells) of the subject as is generally known in the art, such as via parenteral administration (e.g., intravenous, intramuscular, subcutaneous administration) or local administration (e.g., direct dermal application, or iontophoresis), to facilitate delivery.

For delivery of a biologically active agent to an eye or ocular cells (e.g., macula, fovea, cornea, retina), a composition comprising a CPP conjugate described herein is contacted with the eye or ocular cells (e.g., macula, fovea, cornea, retina) of the subject as is generally known in the art, such as via parenteral administration (e.g., intravenous, intramuscular, subcutaneous administration) or local administration (e.g., direct injection, intraocular injection, periocular injection, subretinal, iontophoresis, use of eyedrops, implants), to facilitate delivery.

For delivery of a biologically active agent to an ear or cells of the ear (e.g., cells of the inner ear, middle ear and/or outer ear), a composition comprising a CPP conjugate described herein described herein contacted with the ear or cells of the ear (e.g., cells of the inner ear, middle ear and/or outer ear) of the subject as is generally known in the art, such as via parenteral administration (e.g., intravenous, intramuscular, subcutaneous administration) or local administration (e.g., direct injection), to facilitate delivery.

AMPs

The methods described herein may involve coordinated administration of (i) an AMP, and (ii) an antimicrobial agent (e.g., an agent which treats fungal, (e.g., yeast, or mold) or bacterial infection). The AMP and antibacterial agent are generally as described elsewhere herein, but can be, as examples, D-NOGCON (SEQ ID NO: 37), and/or variants thereof, and colistin.

There are many different approaches to coordinated administration of an AMP and an antimicrobial agent that can be used in the intervention of infection. For instance, the method may include treatment with an antimicrobial agent prior to AMP administration. Taking this approach enables treatment of an acute episode quickly with the antimicrobial agent, while supplementing the action of the antimicrobial agent with the AMP in addressing the acute attack.

In one example, a subject is treated with an antimicrobial agent 1-4 (e.g., 2-3) times before AMP administration, and the antimicrobial treatment takes place, for example, within a time frame of 1, 2, or 3 weeks prior to AMP administration. Thus, in a specific example, a treatment with an antimicrobial agent can be carried out on days −14, −11, and −8 relative to day 0, which is the day on which administration of the AMP takes place. Any of the antimicrobial treatment and/or AMP treatment can vary (e.g., 1 or 2 days) before or after the days noted above.

In another example, antimicrobial treatment takes place concurrently with AMP administration, in addition to (or instead of) prior antimicrobial treatment according to, for example, a schedule as noted above. Thus, in one specific example, antimicrobial treatment takes place on days −14, −11, and −8 (±1 or 2 days for each day of administration), and also on day 0, the same day as AMP administration. The simultaneous treatment with an antimicrobial agent and an AMP described herein, can continue, and be monitored by one skilled in the art, until effective treatment of the infection.

The AMP described herein may be used for a treatment of an infection after the treatment with traditional antimicrobials has failed.

Compositions as described herein can be delivered to a mammalian subject (e.g., a human or other mammal) using a variety of known routes and techniques. For example, a composition can be provided as an injectable solution, suspension, or emulsion, and administered via intramuscular, subcutaneous, intradermal, intracavity, parenteral, epidermal, intraarterial, intraperitoneal, or intravenous injection using conventional methods, such as a syringe, or using a liquid jet injection system. Compositions can also be administered topically to skin or mucosal tissue, such as nasally, intratracheally, intestinal, rectally, or vaginally, or provided as a finely divided spray suitable for respiratory or pulmonary administration. Other modes of administration include oral administration, suppositories, and active or passive transdermal delivery techniques.

The compositions described herein can be administered to a subject (e.g., a human subject that has or is at risk of developing a microbial infection) in an amount that is compatible with the dosage formulation and that will be prophylactically and/or therapeutically effective. An appropriate effective amount will fall in a relatively broad range but can be readily determined by one of skill in the art by routine trials. The "Physician's Desk Reference" and "Goodman and Gilman's The Pharmacological Basis of Therapies" are useful for the purpose of determining the amount needed. An adequate dose of the active antimicrobial agents described herein may vary depending on such factors as preparation method, administration method, severity of symptoms, administration time, administration route, rate of excretion, and responsivity. Generally, the antimicrobial agent will be administered according to the label approved by the relevant regulatory authority. An adequate dose of the AMPs described herein may vary depending on the administration route, age of the subject, the severity of infection, and the identity of the infecting pathogen. A physician of ordinary skill in the art can determine the administration dose effective for treatment.

Methods of Diagnosing a Medical Condition

The CPPs described herein may be conjugated to a reporter to diagnose a medical condition (e.g., a disease). For example, a reporter can be a compound, such as a polypeptide, antibody, small molecule, or fluorescent molecule, wherein the signal from the reporter can be measured. The presence, absence, or difference in signal compared to a control cell without a medical condition could be used to diagnose the subject as having a disease.

For example, the reporter conjugated to a CPP can be the substrate of an enzyme that is not produced in a metabolic disease. Contacting the CPP-conjugate with the enzyme substrate in the sample (e.g., cells or tissue) from the subject will result in the absence of, or reduced cleavage of the substrate conjugated to the CPP in a subject with the metabolic disease, and cleavage of the substrate in a subject without the disease. This readout can be used to diagnose the presence or absence of the metabolic disease.

In one example, the reporter conjugated to a CPP can be an enzyme that is not produced in the sample from the subject due to the diseased state (e.g., the absence of the enzyme glucocerebrosidase in Gaucher disease, which results in excessive accumulation of lysosomal glucocerebroside). The effect following the internalization of the CPP-enzyme conjugate within the cell can be observed, such as the production of a cleavage product of the enzyme, which would indicate that the subject has the metabolic condition.

Dosage and Administration

The pharmaceutical compositions described herein can be administered to a subject (e.g., a human) in a variety of ways. For example, the pharmaceutical compositions may be formulated for and/or administered orally, buccally, sublingually, parenterally, intravenously, subcutaneously, intramedullary, intranasally, as a suppository, using a flash formulation, topically, intradermally, subcutaneously, via pulmonary delivery, via intra-arterial injection, ophthalmically, optically, intrathecally, or via a mucosal route.

In general, the dosage of a pharmaceutical composition or the active agent (e.g., a CPP, CPP-conjugate, or AMP described herein) in a pharmaceutical composition described herein may be in the range of from about 1 pg to about 10 g (e.g., 1 pg-10 pg, e.g., 2 pg, 3 pg, 4 pg, 5 pg, 6 pg, 7 pg, 8 pg, 9 pg, 10 pg, e.g., 10 pg-100 pg, e.g., 20 pg, 30 pg, 40 pg, 50 pg, 60 pg, 70 pg, 80 pg, 90 pg, 100 pg, e.g., 100 pg-1 ng, e.g., 200 pg, 300 pg, 400 pg, 500 pg, 600 pg, 700 pg, 800 pg, 900 pg, 1 ng, e.g., 1 ng-10 ng, e.g, 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., 100 ng-1 µg, e.g., 200 ng, 300 ng, 400 ng, 500 ng, 600 ng, 700 ng, 800 ng, 900 ng, 1 µg, e.g., 1-10 µg, e.g., 1 µg, 2 µg, 3 µg, 4 µg, 5 µg, 6 µg, 7 µg, 8 µg, 9 µg, 10 µg, e.g., 10 µg-100 µg, e.g., 20 µg, 30 µg, 40 µg, 50 µg, 60 µg, 70 µg, 80 µg, 90 µg, 100 µg, e.g., 100 µg-1 mg, e.g., 200 µg, 300 µg, 400 µg, 500 µg, 600 µg, 700 µg, 800 µg, 900 µg, 1 mg, e.g., 1 mg-10 mg, e.g., 2 mg, 3 mg, 4 mg, 5 mg, 6 mg, 7 mg, 8 mg, 9 mg, 10 mg, e.g., 10 mg-100 mg, e.g., 20 mg, 30 mg, 40 mg, 50 mg, 60 mg, 70 mg, 80 mg, 90 mg, 100 mg, e.g., 100 mg-1 g, e.g., 200 mg, 300 mg, 400 mg, 500 mg, 600 mg, 700 mg, 800 mg, 900 mg, 1 g, e.g., 1 g-10 g, e.g., 2 g, 3 g, 4 g, 5 g, 6 g, 7 g, 8 g, 9 g, 10 g).

The pharmaceutical composition may also be administered in a unit dose form or as a dose per mass or weight of the subject from about 0.01 mg/kg to about 100 mg/kg (e.g., 0.01-0.1 mg/kg, e.g., 0.02 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg). The dose may also be administered as a dose per mass or weight of the subject per unit day (e.g., 0.1-10 mg/kg/day).

The dosage regimen may be determined by the clinical indication being addressed, as well as by various subject variables (e.g., weight, age, sex) and clinical presentation (e.g., extent or severity of disease). Furthermore, the pharmaceutical compositions may be administered continuously or divided into dosages given per a given time frame. The composition may be administered, for example, every hour, day, week, month, or year.

Kits

CPPs

Also featured are kits containing a CPP or CPP-conjugatedescribed herein, e.g., for use in the instant methods. Kits of the invention include one or more containers comprising, for example, CPPs, polynucleotides encoding one or more CPPs or conjugates, combinations thereof, and fragments thereof, and, optionally, instructions for use in accordance with any of the methods described herein.

Generally, these instructions comprise a description of administration or instructions for performance of an assay. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also envisioned.

The kits may be provided in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (e.g., the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). Kits may optionally provide additional components such as buffers and interpretive information. Normally, the kit comprises a container and a label or package insert(s) on or associated with the container.

AMPs

Also featured are kits containing an AMP described herein, e.g., for use in the instant methods. Kits of the invention include one or more containers comprising, for example, AMPs, polynucleotides encoding one or more AMPs, combinations thereof, and fragments thereof, and, optionally, instructions for use in accordance with any of the methods described herein.

Generally, these instructions comprise a description of administration or instructions for performance of an assay. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also envisioned The kits may be provided in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (e.g., the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). Kits may optionally provide additional components such as buffers and interpretive information. Normally, the kit comprises a container and a label or package insert(s) on or associated with the container.

EXAMPLES

The following examples are put forth to provide those of ordinary skill in the art with a description of how the compositions and methods described herein may be used, made, and evaluated, and are intended to be purely exemplary of the invention and are not intended to limit the scope of what the inventors regard as their invention.

Example 1

Figure 2:
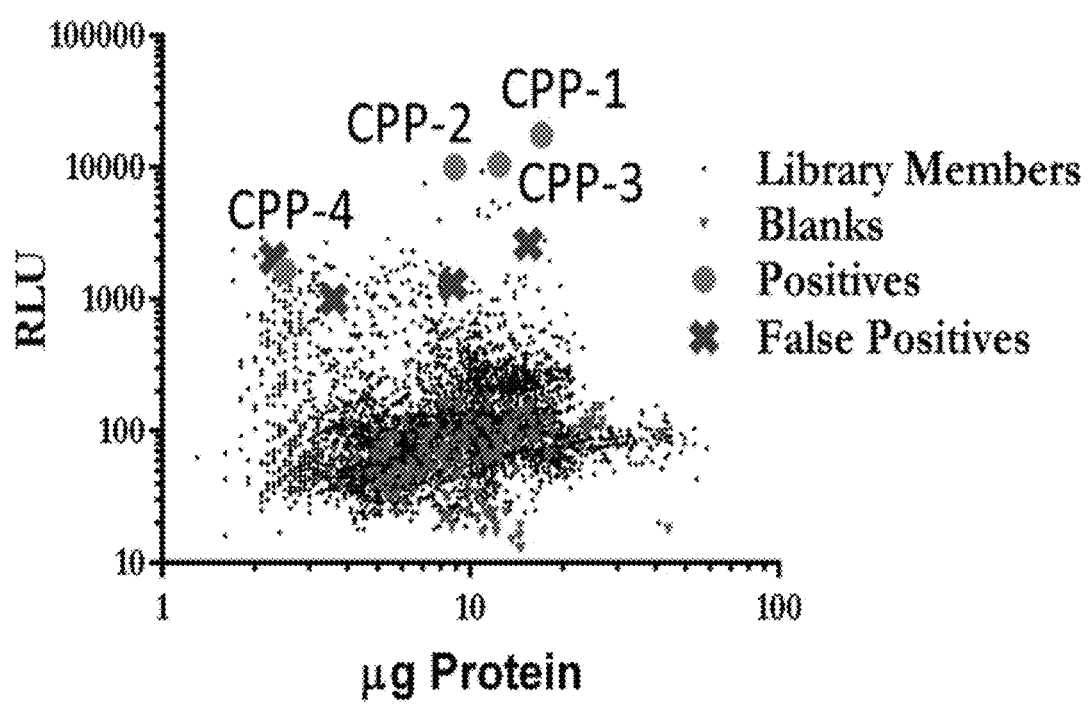
FIG. 2 is a graph showing the results from a 96-well plate with those corresponding to positive beads selected for sequencing highlighted. Relative luminescent units from the luciferase assay are plotted against the µg protein per well. Positive sequences have high luminescent values with protein values suggesting that the treatment did not inhibit cell growth during the recovery period. Points in green are positive sequences, points designated by purple "X"s are false positive sequences, and points in red are negative controls.
Figure 3:
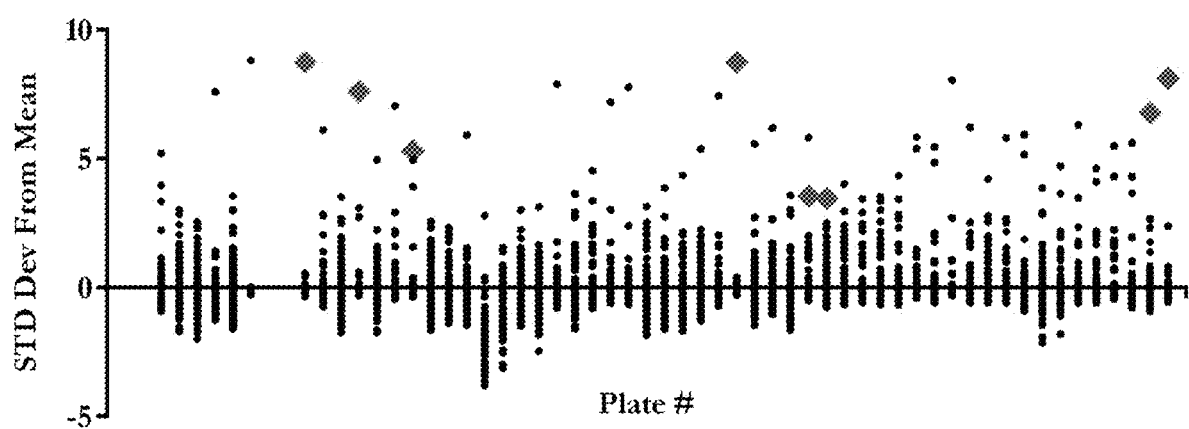
FIG. 3 is a graph of the number of standard deviations of each well from the plate mean from the 96-well plate of FIG. 2. This allows for selection of positive sequences while eliminating bias resulting from plate to plate experimental variability. All positive sequences selected for future study featured RLU/µg protein values that were at least three standard deviations above the plate mean.

We identified improved CPPs by their ability to deliver a PNA cargo, (SEQ ID NO: 11), which is an 18-mer sequence that sterically blocks an aberrant splice site in HeLa cells stably transfected with a luciferase transgene containing a human β-globin intronic insert with a T705G mutation (FIG. 2 and FIG. 3). We screened these sequences for the ability to deliver a splice-correcting peptide nucleic acid (PNA) sequence to the interior of cells. PNAs are synthetic nucleic acid analogues possessing a peptide bond linked N-(2-aminoethyl) glycine backbone with the nucleobase (A/T/C/G) attached via methylene carbonyl bonds. These molecules are resistant to enzymatic degradation, stably bind complimentary nucleic acids with high specificity and affinity using Watson-Crick base pairing, and are easily conjugated to amino acid sequences, fluorescent molecules, and other molecules. As antisense gene therapy agents, they can inhibit transcription, artificially initiate transcription, inhibit translation, inhibit replication, modify splicing, and isolate specific active genes. The splice correcting PNA705 sequence makes an ideal cargo for this study because i) it requires nuclear delivery, ii) delivery results in a concentration dependent luminescent signal, iii) cytotoxic CPP sequences are selected against as transcription would be attenuated, iv) it is possible to later change the PNA target without dramatically changing the physicochemical properties of the cargo (modularity), and v) resistance of PNA to enzymatic degradation means that any impact of proteolysis on the splice correcting ability of the hybrid construct will be constrained to the peptide sequence.

Peptide Library Design and Synthesis

To evolve gain of function from the known Tat (SEQ ID NO: 1) and penetratin (SEQ ID NO: 2) sequences a peptide library of Tat/penetratin hybrid sequences on the N-terminus of the PNA705 (SEQ ID NO: 11) was created. When aligned, the 13 residue Tat sequence and 16 residue penetratin sequence share a lysine at position 4 and an arginine at position 10. We allowed for a hydrophobic Leu option at position 10 while Lys at position 4 is common in all sequences. The three additional residues of Penetratin, Trp-Lys-Lys, were randomly present as a cassette or absent, resulting in 13 variable positions in peptides of 13 or 16 residues. The peptide library was a one-bead-one-peptide library, synthesized using a split and recombine approach. The strategy generated 8,192 members in the peptide library containing a C-terminal photo-labile linker followed by the 18-residue PNA705 sequence and the N-terminal CPP library member (FIG. 1). The library members were synthesized on TENTAGEL® Megabead MB NH$_2$ resin beads (Raap Polymere MB300002), coupled to it by a UV-cleavable photo linker, 4-(4-[1-(9-Fluorenylmethyloxycarbonylamino)ethyl]-2-methoxy-5-nitrophenoxy) butanoic acid. After synthesis, sidechains were deprotected with a mixture of trifluoroacetic acid and scavengers. Beads were then washed extensively and stored dry at −20° C. prior to use.

To cleave the photolabile linker and release the library members, beads were first suspended in methanol and dispersed onto a glass plate. The beads were dried thoroughly and then exposed to UV light at 365 nm for 4 hours with illumination from plate top and bottom. One day prior to screening, beads were placed into the wells of a 96-well plate, one bead per well. Water and hexafluoroisopropanol (25 μL each) were added to each well, and the plates were exposed to 365 nm UV light for an additional 3 hours, releasing and extracting the peptide while also evaporating the solvent. Finally, 25 μL of water was added to each well and plates were incubated overnight for peptide solubilization. About 0.5 nmol of peptide was extracted from each bead, as quantified by tryptophan fluorescence.

Identifying Effective CPPs

Following side-chain deprotection and cleavage from the resin with uv light, the CPP-PNA705 constructs were dissolved in ddH2O and added to Hela pLuc705 cells in serum free media in 96-well plate format. Cells were incubated for 1 hour at 37° C., then topped with an equal volume of 2× complete DMEM. The CPP-PNA705 concentration in each well was 5-10 μM. After 24 hours, cells were lysed and analyzed for functional luciferase and total protein (FIG. 2 and FIG. 3). Positives were defined as sequences whose relative luminescent units (RLU)/μg protein values were at least 3 standard deviations above the plate mean. Beads, which contained a residual amount of the CPPs, were sequenced by Edman degradation. Following a preliminary assessment of eight potential positives, we selected four out of the eight sequences, called CPP-3, CPP-1, CPP-2 and CPP-4, for subsequent detailed analysis (FIG. 4).

Example 2. Cytotoxity Analysis

Figure 5A:
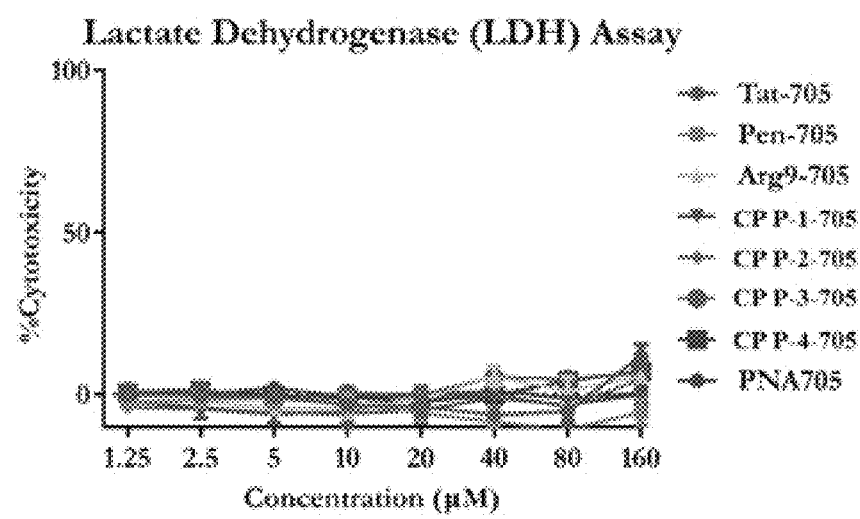
FIG. 5A is a graph depicting the results of HeLa pTRE-LucIVS2-705 cells treated with varying concentrations of peptides from FIG. 4 linked to PNA705 (SEQ ID NO: 11) and analyzed using a lactate dehydrogenase (LDH) assay.
Figure 5B:
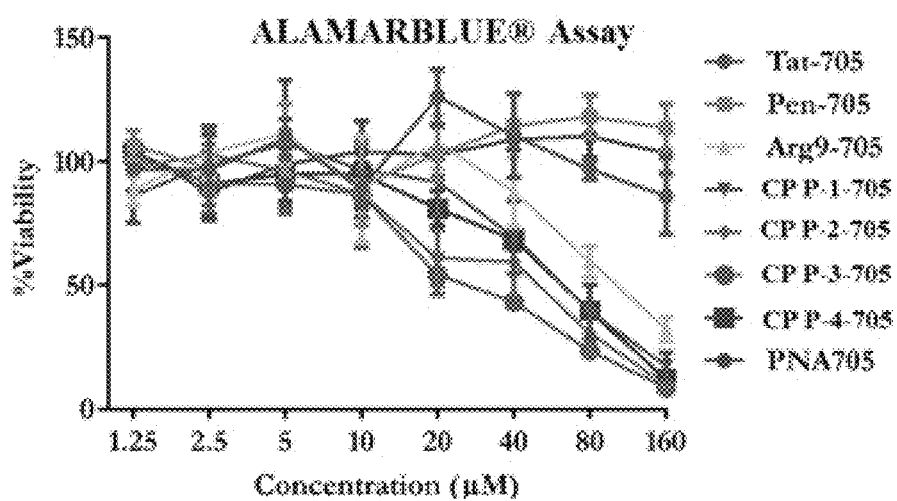
FIG. 5B is a graph depicting the results of HeLa pTRE-LucIVS2-705 cells treated with ALAMARBLUE® cell viability reagent after treatment with CPP peptides of FIG. 4 linked to PNA705.
Figure 5C:
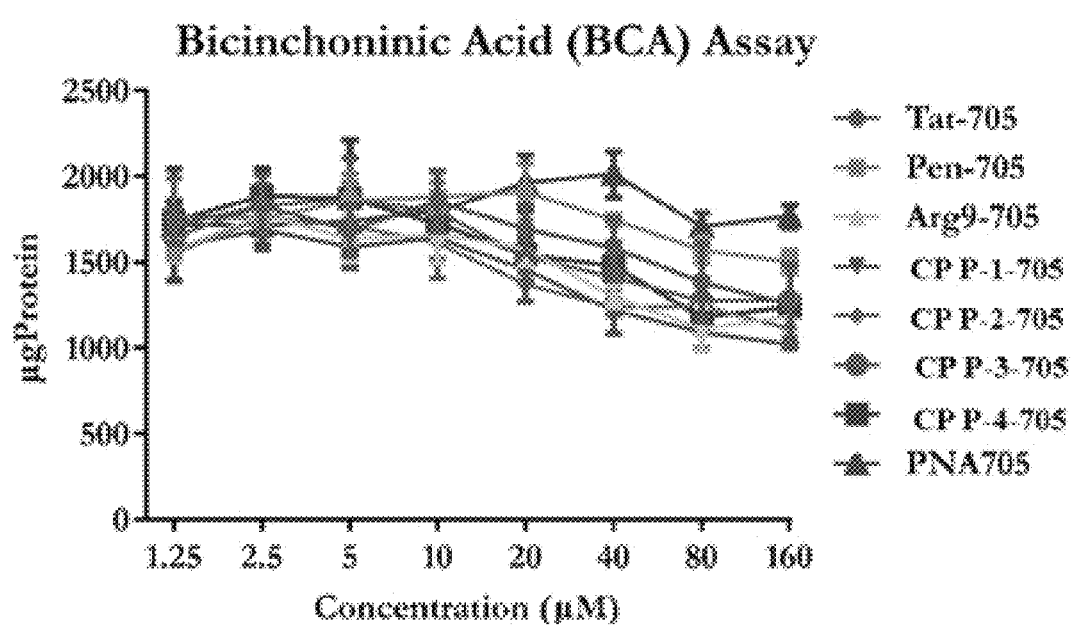
FIG. 5C is a graph showing the results of HeLa pTRE-LucIVS2-705 cells in a bicinchoninic acid (BCA) assay.

CPP-PNA705 cytotoxicity was assessed using several methods known in the art. A Lactate Dehydrogenase (LDH) assay (FIG. 5A) measured the acute cytotoxicity and detects LDH released by cells because of membrane damage resulting from exposure to the CPPs. An ALAMARBLUE® assay (FIG. 5B) and a Bicinchoninic Acid (BCA) Assay (FIG. 5C) both measure the impact of exposure after 24 hours. In the ALAMARBLUE®, assay some reduction in metabolic activity was detected in Hela705 cells treated with 20 μM CPP-PNA705 concentrations for 1 hour. After 24 hours, cells treated with 10 μM CPP-1 and CPP-2 showed a 20% and 10% reduction in metabolic activity respectively, while CPP-3 and CPP-4 showed little effect. No effect was observed at 5 μM or lower for any CPP-PNA conjugate.

Example 3. Cargo Delivery in Cell Culture to the Nucleus

Figure 6:
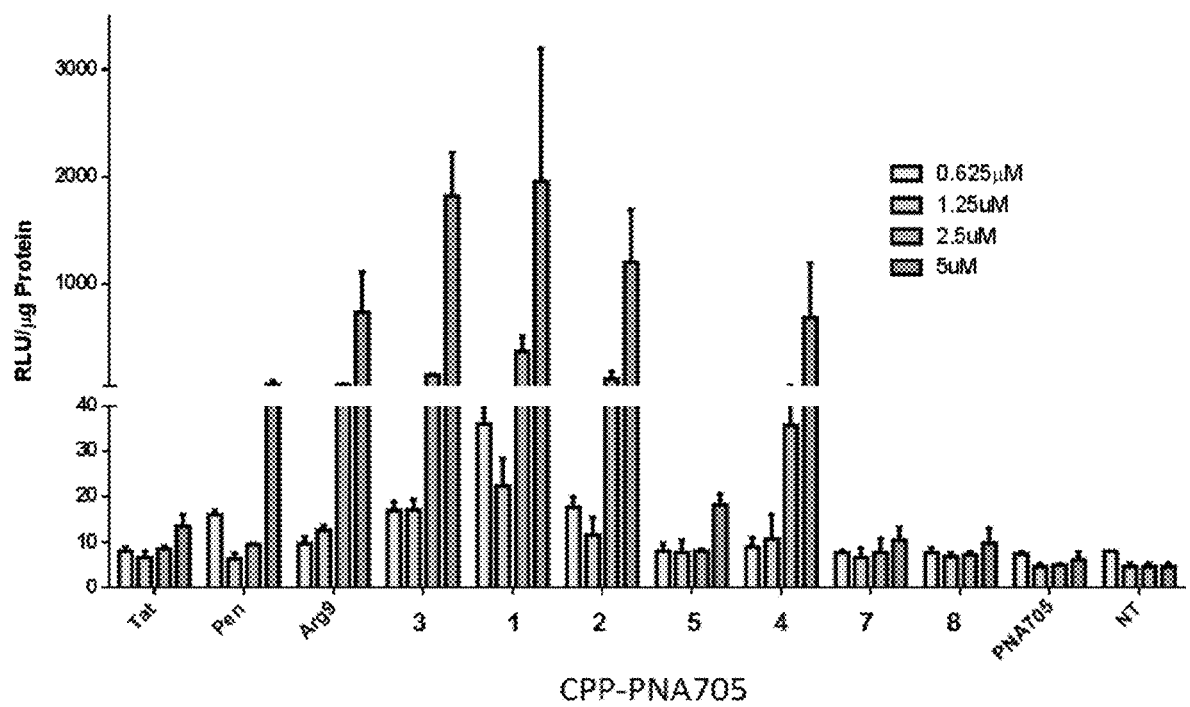
FIG. 6 is a graph showing HeLa pTRE-LucIVS2-705 cells after treatment with varying concentrations of CPP peptides of FIG. 4 linked to PNA705 for 30 minutes at 37° C. and allowed to recover for 24 hours. Included in the analysis were PNA705 conjugated parent sequences Tat and penetratin as well as the Tat analog Arg9 (SEQ ID NO: 13). Untreated cells and cells treated with PNA705 served as negative controls.
Figure 7:
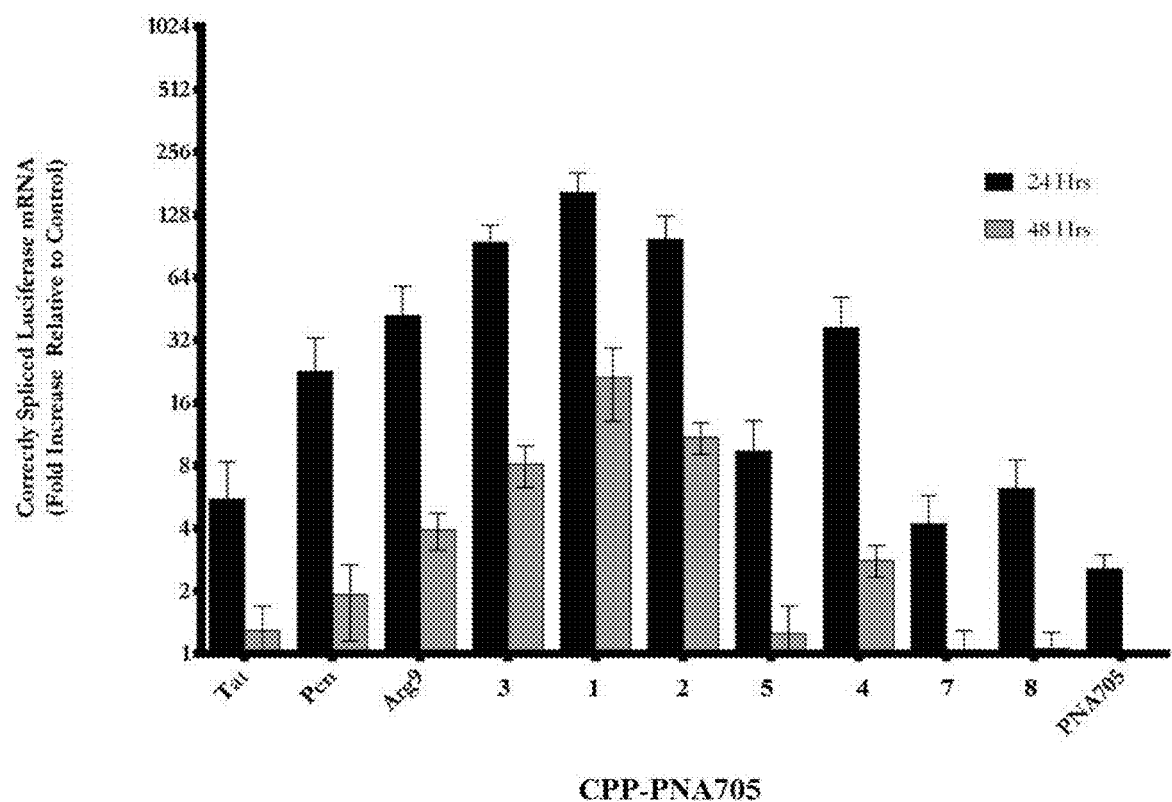
FIG. 7 is a graph showing the results from HeLa pTRE-LucIVS2-705 cells treated with 5 µM of CPP of FIG. 4 linked to PNA705 for 30 minutes at 37° C. and allowed to recover for 24 or 48 hours in complete media. Following lysis and RNA purification, primers targeting the splice junction of functional luciferase mRNA were used in a qRT-PCR assay to quantify the fold increase in corrected mRNA following nuclear delivery.

To assess nuclear cargo delivery and splice correction, PNA705 (SEQ ID NO: 11) was used. Luciferase production was quantified at both the protein (FIG. 6) and mRNA levels (FIG. 7). To quantify functional luciferase levels following splice correction, Hela pLuc705 cells were treated with a 2× serial dilution starting at 5 μM of CPP-PNA705 for 30 minutes in serum free DMEM at 37° C., washed in PBS, and allowed to recover for 24 hours in complete media. To assess the impact of endosomal entrapment and subsequent lysosomal degradation, some cells were co-treated with the endosomal acidification inhibitor chloroquine (120 μM) along with 5 μM CPP-PNA705. Cell lysates were assayed for luciferase by luminescence. To control for total cell density, lysates were also analyzed for total protein by the BCA assay.

All CPP sequences delivered PNA705 much more efficiently in cell culture than their parents, with CPP-1-PNA705≈CPP-2-PNA705>CPP-3-PNA705>CPP-4-PNA705. At 5 μM, the top performing CPP, CPP-1-PNA705, produced 33× and 145× higher RLU/μg protein values, respectively, than the parent sequences penetratin and tat. At concentrations as low as 625 nM, CPP-1-PNA705 was still 3× above the background signal. Interestingly, the canonical tat analog Arg9 delivered PNA705 much better than Tat, yet the sequences CPP-3-PNA705, CPP-1-PNA705, and CPP-2-PNA705 outperformed Arg9 by 2.5×, 2.7×, and 1.7× respectively at 5 µM. Chloroquine treatment moderately increased the RLU/µg protein values for CPP-3-PNA705 by +44%, CPP-2-PNA705 by +81%, and CPP-4-PNA705 by +173%, but decreased the delivery of CPP-1-PNA705 by 29%, suggesting sequence specific levels of endosomal entrapment.

Figure 8:
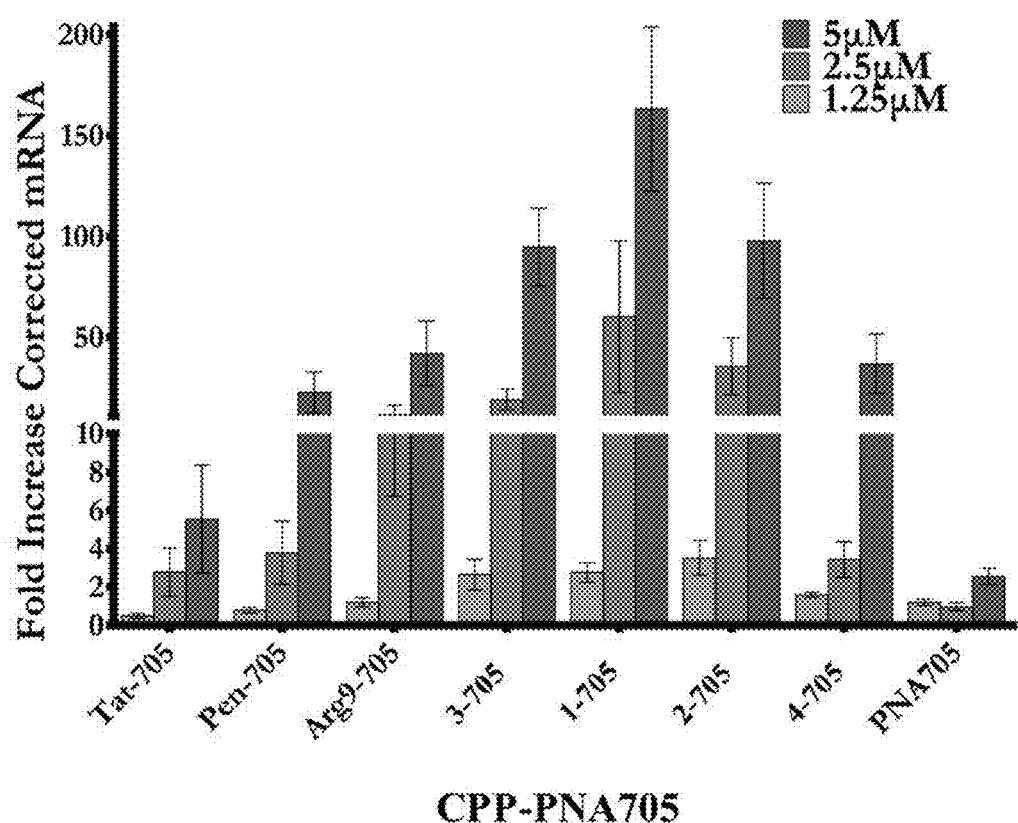
FIG. 8 is a graph showing the results from HeLa pTRE-LucIVS2-705 cells treated with varying concentrations of CPPs of FIG. 4 linked to PNA705 for 30 minutes at 37° C. and allowed to recover for 24 hours in complete media. Following lysis and RNA purification, primers targeting the splice junction of functional luciferase mRNA were used in a qRT-PCR assay to quantify the fold increase in corrected mRNA.
Figure 9:
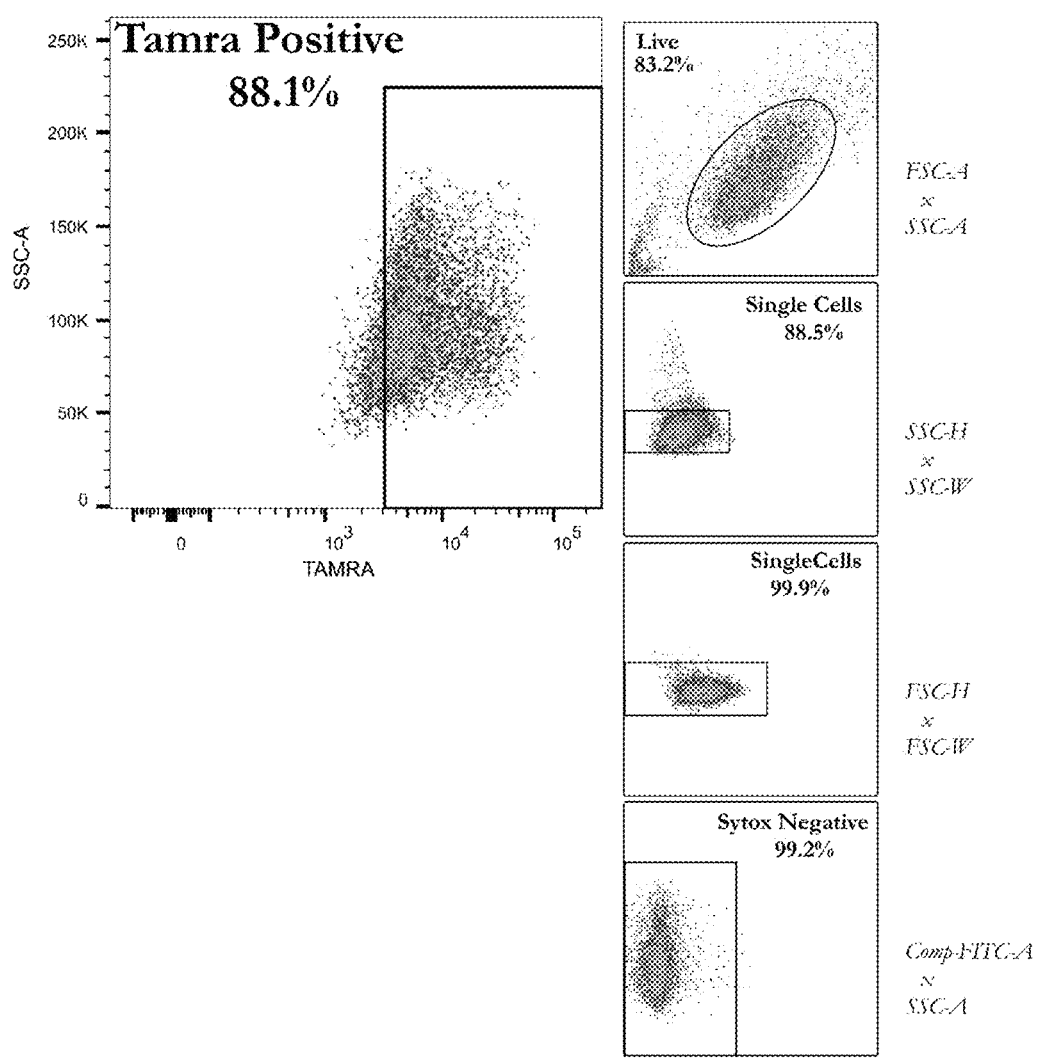
FIG. 9 is a plot showing the flow cytometry gating strategy for cells treated with CPPs of FIG. 4 C-terminally linked to TAMRA (CPP-C-TA). Here, HeLa cells were treated with 5 µM CPP-C-TA for 30 minutes at 37° C. Live cells were identified by forward and side scatter. Doublets were excluded in two gating steps using SSC-H×SSC-W and FSC-H×FSC-W. Cells with compromised membranes permitting SYTOX green entry were excluded. The percent of the remaining cells testing positive for TAMRA fluorescence were defined as those with a fluorescence value≥3000. Additionally, the mean fluorescence for all SYTOX negative cells was recorded.
Figure 10A:
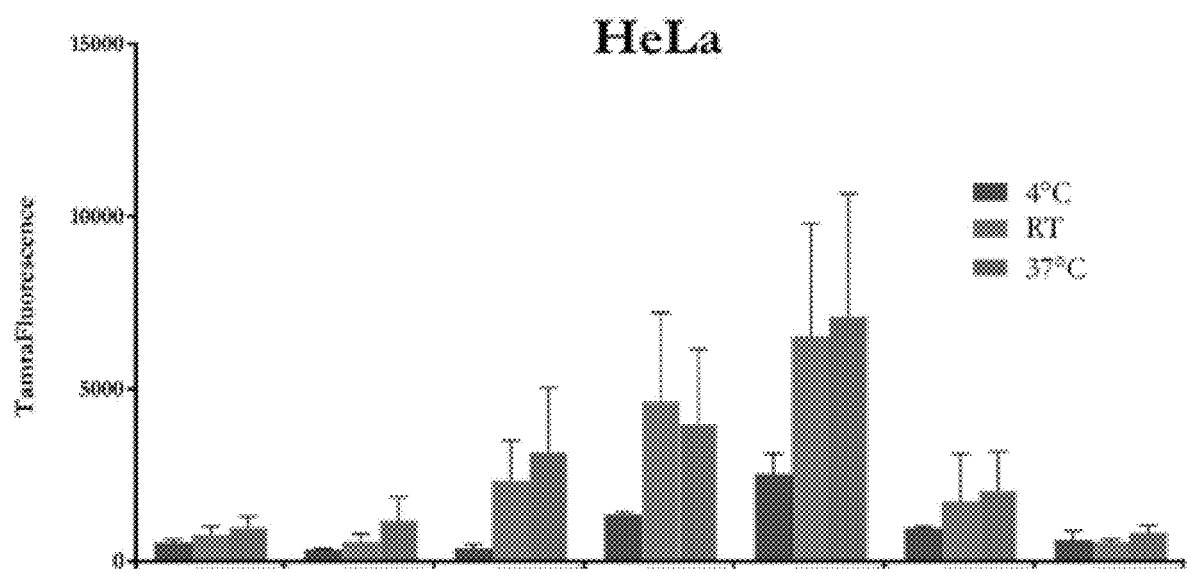
FIGS. 10A-10C show the results of flow cytometric and confocal microscopy experiments. HeLa cells incubated with 0.5 µM CPP-C-TA+4.5 µM CPP-C at 4° C., 22° C., and 37° C.
Figure 10B:
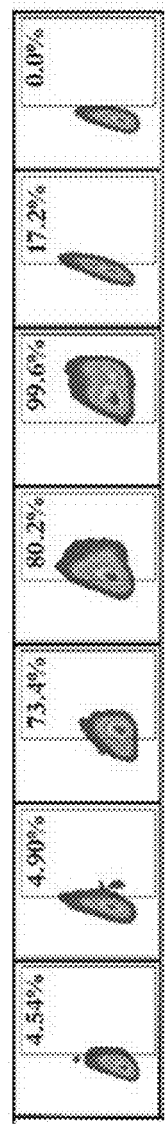
Figure 10C:
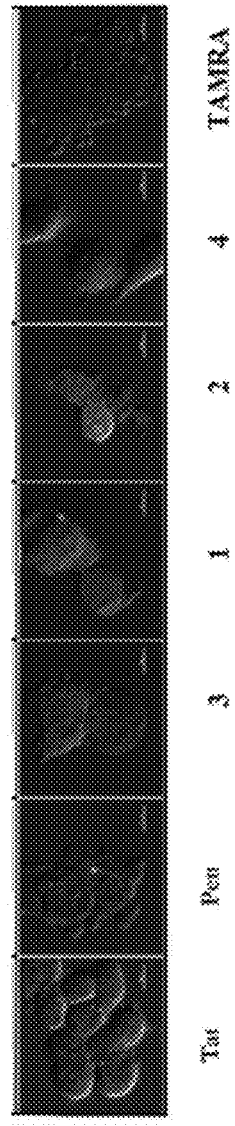
Figure 11A:
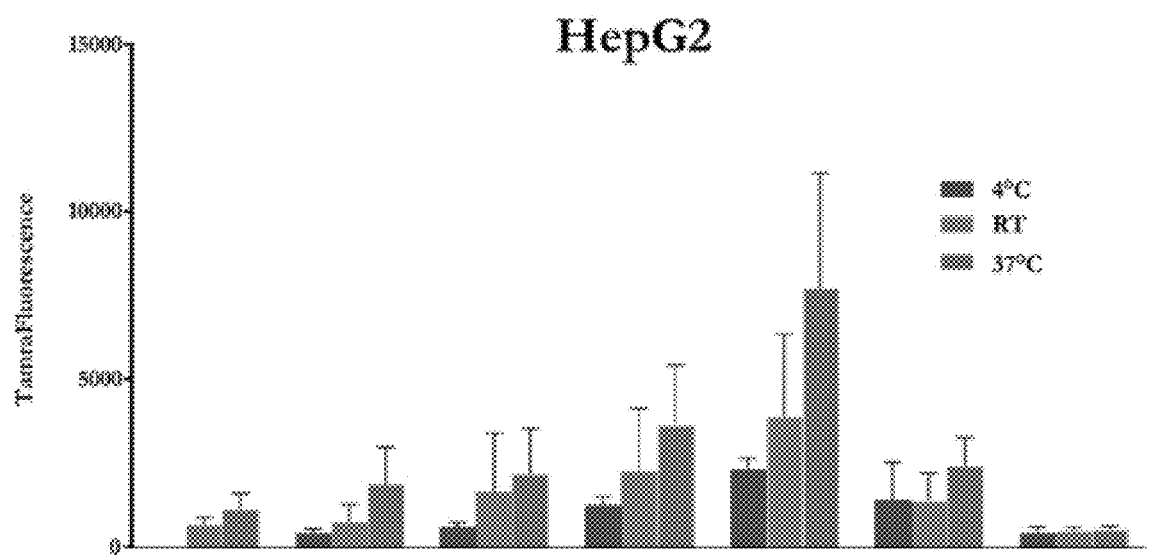
FIGS. 11A-11C show the results of flow cytometric and confocal microscopy experiments. HepG2 cells were incubated with 0.5 µM CPP-C-TA+4.5 µM CPP-C at 4° C., 22° C., and 37° C.
Figure 11B:
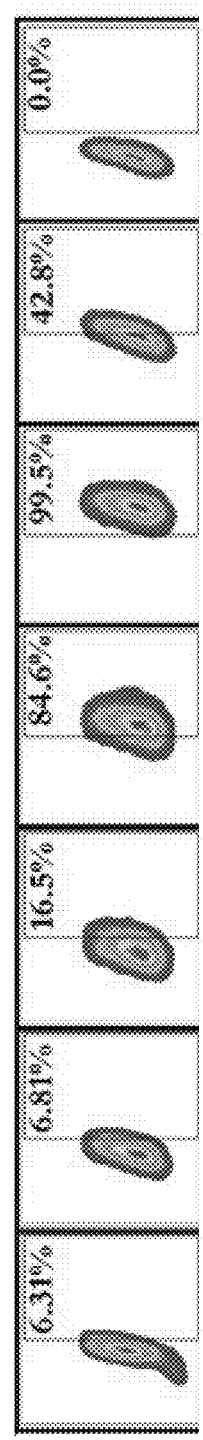
Figure 11C:
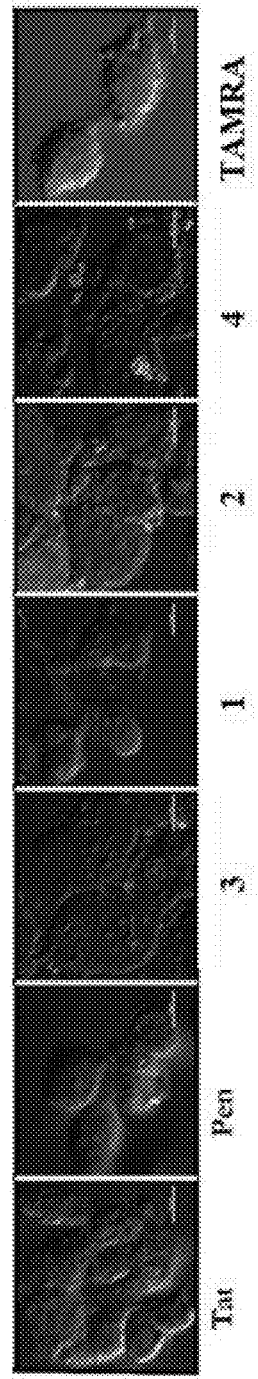
Figure 12A:
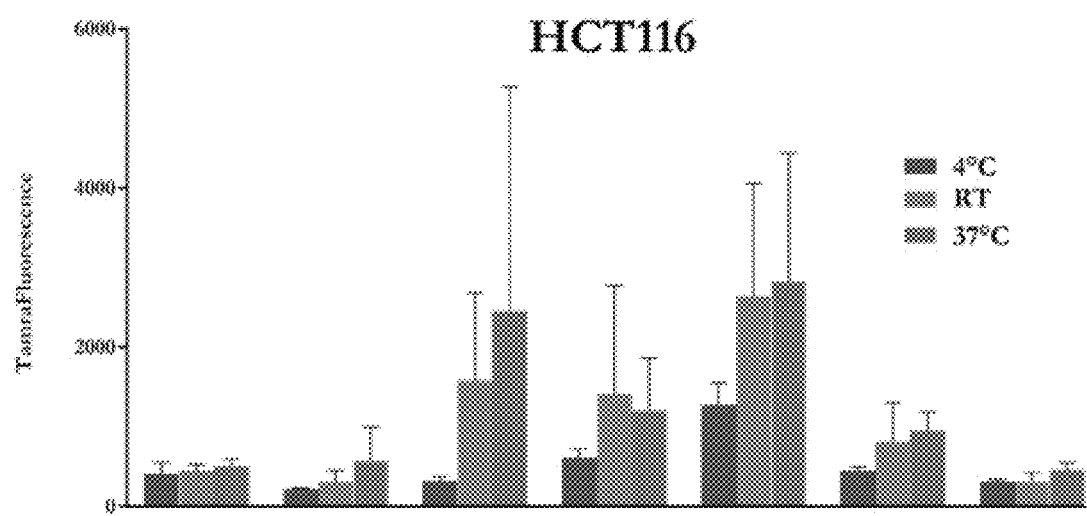
FIGS. 12A-12C show the results of flow cytometric and confocal microscopy experiments. HCT116 cells were incubated with 0.5 µM CPP-C-TA+4.5 µM CPP-C at 4° C., 22° C., and 37° C.
Figure 12B:
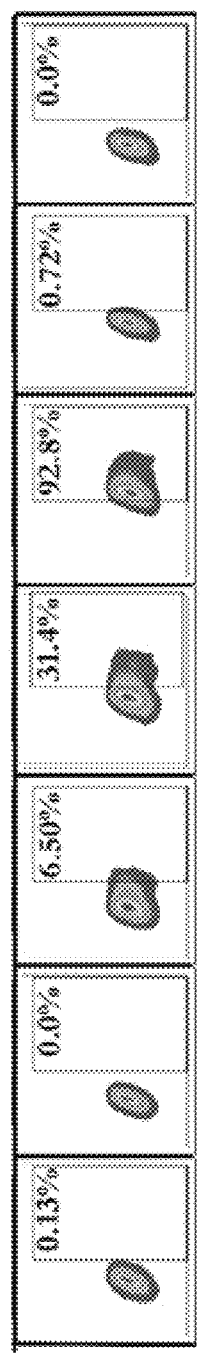
Figure 12C:
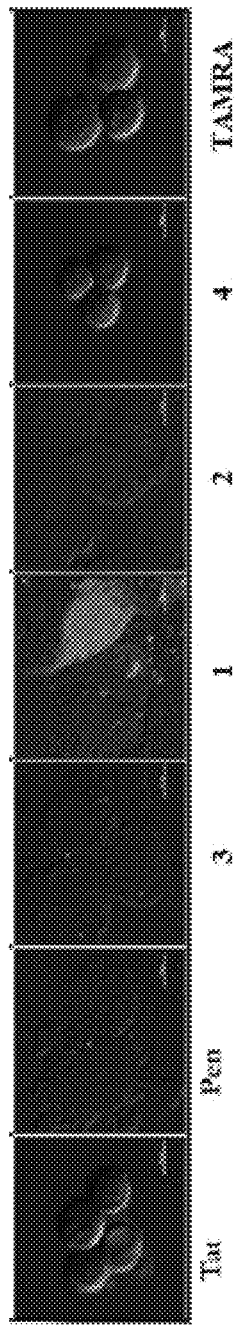
Figure 13A:
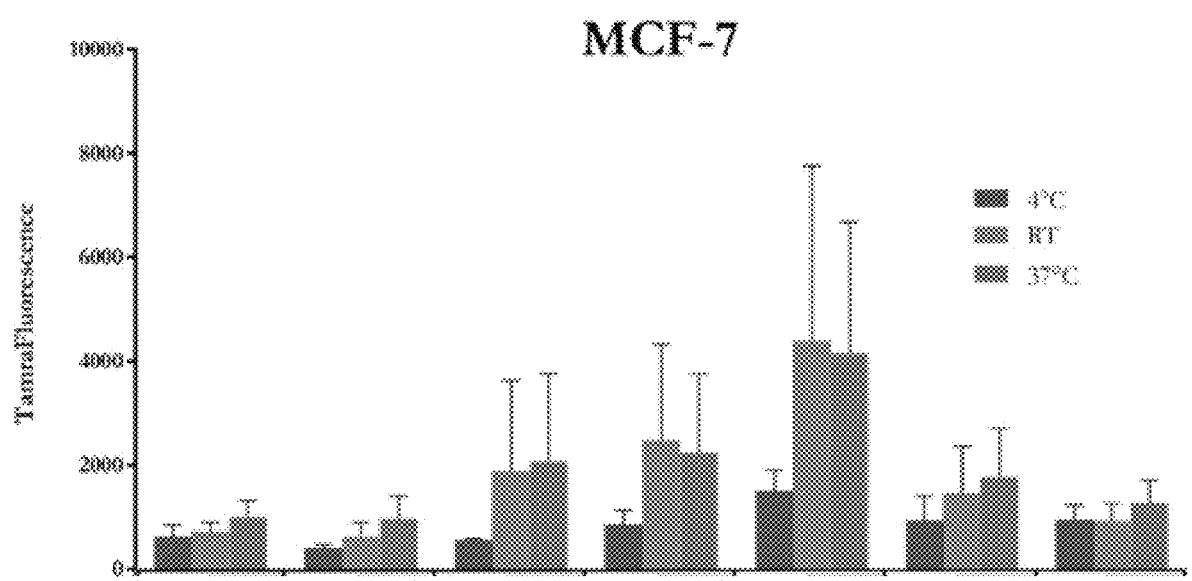
FIGS. 13A-13C show the results of flow cytometric and confocal microscopy experiments. MCF-7 cells were incubated with 0.5 µM CPP-C-TA+4.5 µM CPP-C at 4° C., 22° C., and 37° C.
Figure 13B:
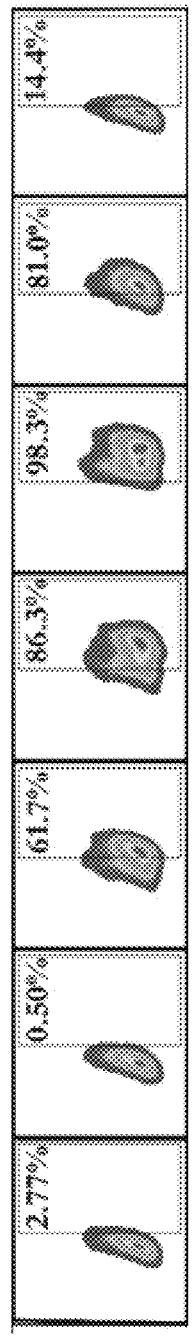
Figure 13C:
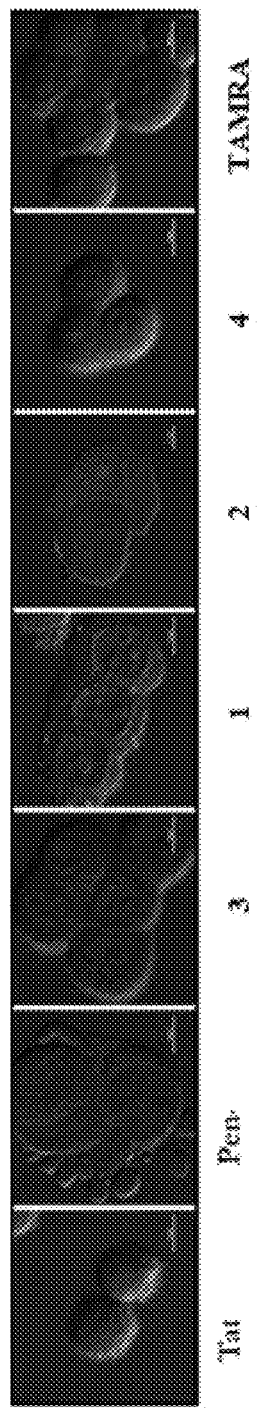
Figure 14A:
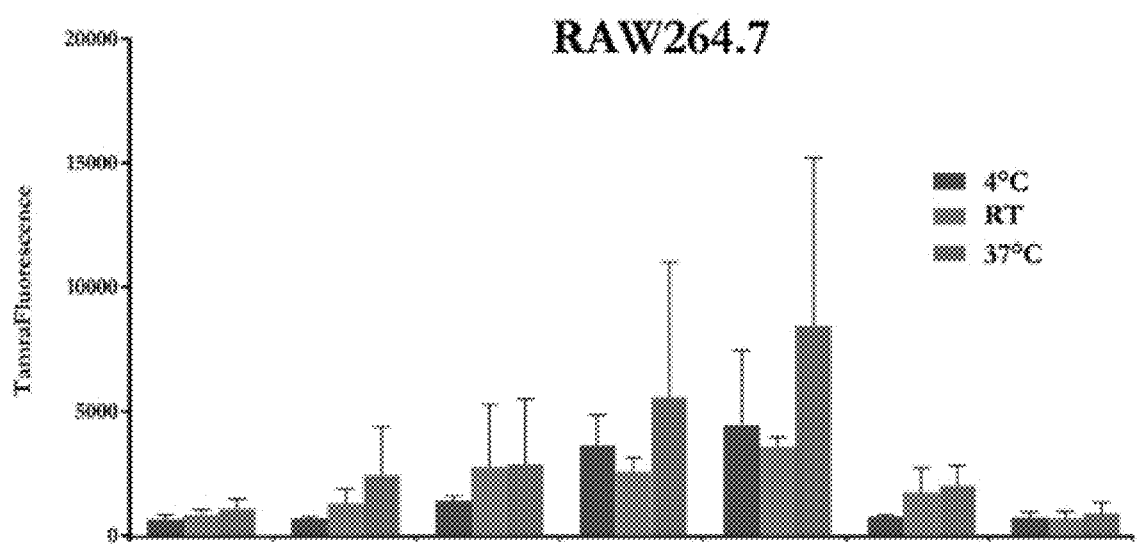
FIGS. 14A-14C show the results of flow cytometric and confocal microscopy experiments. RAW264.7 cells were incubated with 0.5 µM CPP-C-TA+4.5 µM CPP-C at 4° C., 22° C., and 37° C.
Figure 14B:
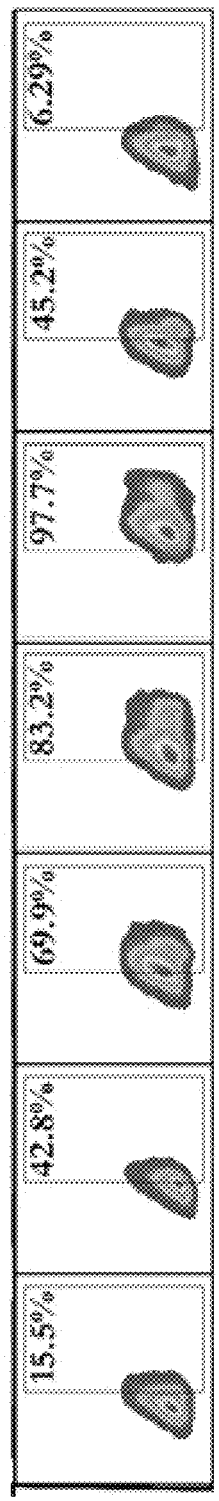
Figure 14C:
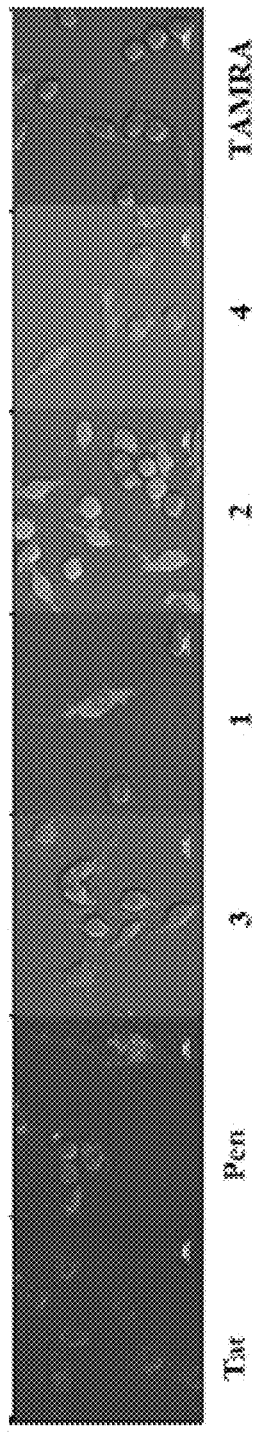
Figure 15:
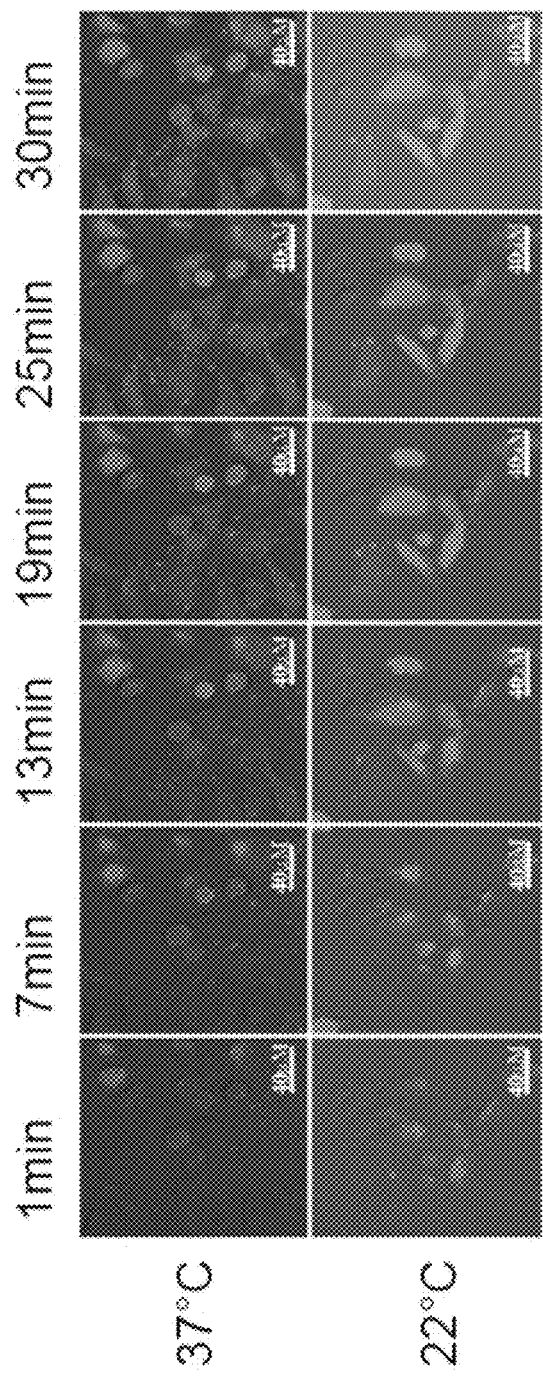
FIG. 15 are photomicrographs showing confocal microscopy images of the results of HeLa cells treated with 0.5 µM CPP-2-C-TA+4.5 µM CPP-2-C at 22° C., and 37° C. in serum free DMEM. Confocal images were acquired at 30 second intervals for 30 minutes. 125 nm SYTOX Green is included in the incubation medium to identify cells with compromised membranes.
Figure 16:
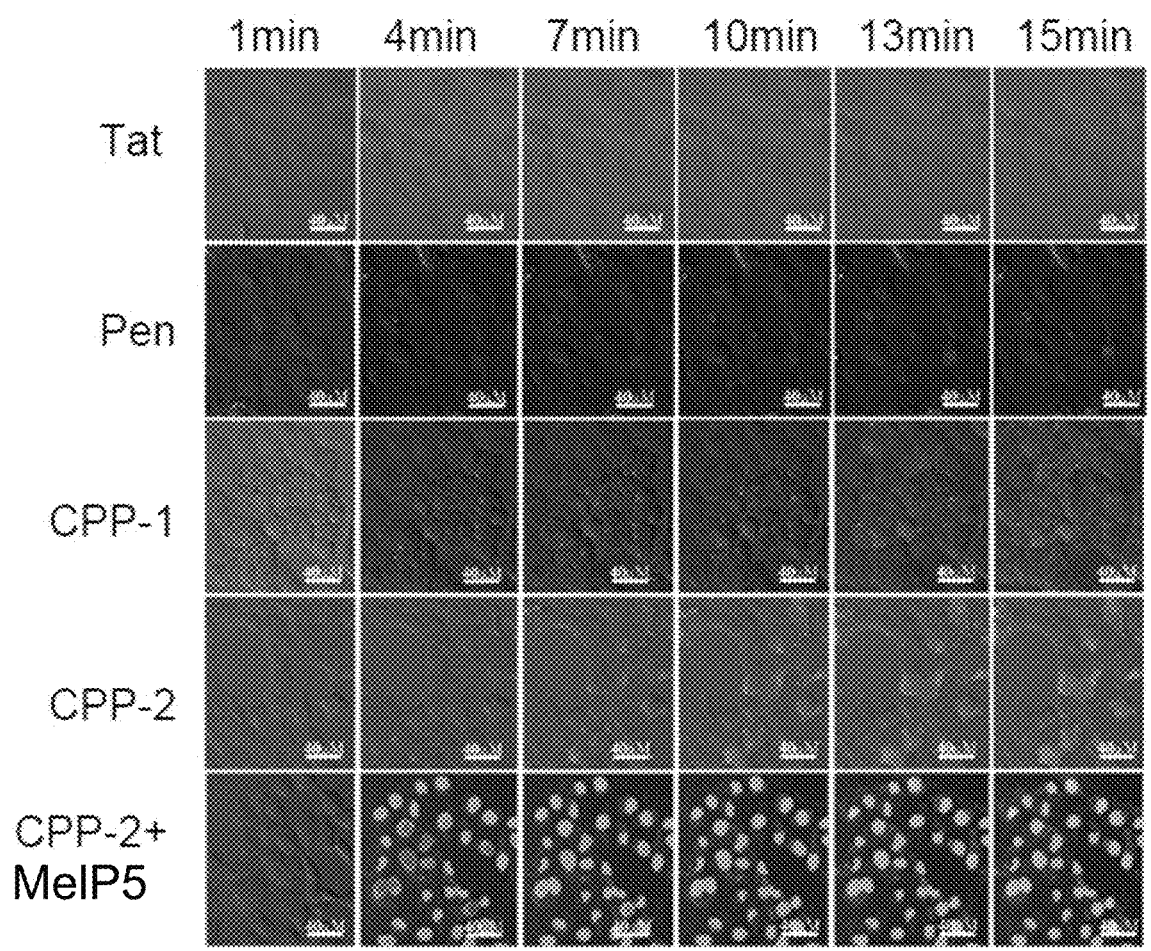
FIG. 16 are photomicrographs showing confocal microscopy images of the results of HeLa cells treated with 0.5 µM CPP-C-TA+4.5 µM CPP-C at 37° C. in serum free DMEM. Confocal microscopy images were acquired at 30 second intervals for 15 minutes. 125 nm SYTOX Green is included in the incubation medium to identify cells with compromised membranes. As a positive control for membrane disruption, the lytic peptide MelP5 has been added to 0.5 µM CPP-2-C-TA.

To quantify splice correction at the mRNA level we designed qRT-PCR primers to target the splice junction of the properly spliced mRNA transcript. We measured the levels of functional luciferase mRNA after 30-minute incubations followed by a 24 and 48-hour recovery period with 5 µM, 2.5 µM, and 1.25 µM CPP-705 (FIG. 8). These data validate the luciferase assay results. We observe a 163× increase in properly spliced luciferase mRNA in cells treated with CPP-1-PNA705 relative to control, which is 7.2× more than penetratin and 30× more than Tat. At 2.5 µM, the increase over control is 60× which is 15.9-fold higher than penetratin and 21.7-fold higher than TAT. At 5 µM, CPP-3-PNA705, CPP-1-PNA705, and CPP-2-PNA705 outperformed Arg9 by 2.3×, 3.9×, and 2.3× respectively.

These data show that CPPs can be used to deliver nucleic acids, such as peptide nucleic acids, to an intracellular domain, such as the nucleus, without altering the functionality of the nucleic acids.

Example 4. Delivery of a Diagnostic Fluorophore

To determine the effect of the PNA cargo on delivery, we labeled CPPs, lacking the PNA705 cargo, with the fluorophore TAMRA on a C-terminal cysteine residue (CPP-TA) and measured delivery to multiple cell types. TAMRA-labelled CPPs, mixed with unlabeled CPPs at a 1:10 ratio in serum-free DMEM for a final concentration of 5 µM total peptide, was added to HeLa, RAW264.7, HepG2, and MCF-7 cells in 12-well cell culture plates and incubated for 30 minutes at 4° C., 22° C., or 37° C. prior to flow cytometric analysis (FIGS. 9-16). Time lapse confocal microscopy at 23° C. shows rapid internalization of CPP-TAMRA constructs with maximum intensity reached by 30 minutes. While there was variability between cell types and incubation temperatures, CPPs consistently delivered TAMRA to a significantly larger percentage of treated cells than either parent, Tat or penetratin. Furthermore, the mean TAMRA fluorescence shows the CPPs effectively delivered more TAMRA cargo to cells than the parent CPPs. In most experiments, CPP-2»CPP-3=CPP-1>CPP-4>TAT=penetratin which is similar to the efficiency of PNA705 delivery, except that CPP-1 is most efficient at PNA delivery. Co-incubation with Sytox green at 125 nM shows negligible membrane lysis or acute cytotoxicity. Delivery of TAMRA was verified by confocal microscopy for each cell type. The diffuse staining pattern obtained following room temperature incubations with CPP-TAMRA conjugates in less than 15 minutes suggests an energy independent mechanism of entry directly through the plasma membrane. This is consistent with the fact that similar delivery was observed at 37° C., permissive for endocytosis, and at 4° C. and 22° C., conditions under which endocytosis is inhibited.

These data show that the CPPs can be used to deliver a fluorophore (e.g., TAMRA) to an intracellular domain of multiple cell types.

Example 5. Delivery of a Polypeptide

Figure 17A:
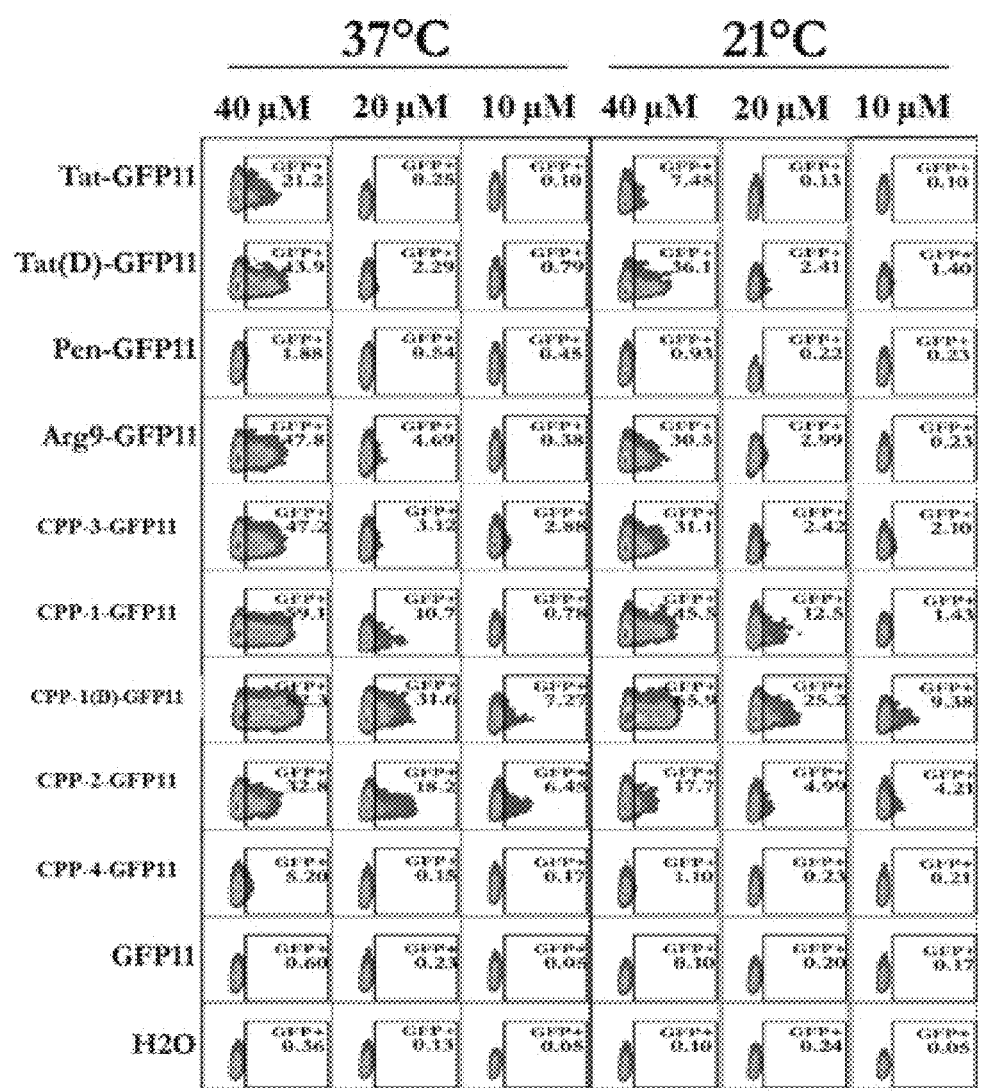
FIGS. 17A-17B show the results of CPP-GFP-11 delivery to cells.
Figure 17B:
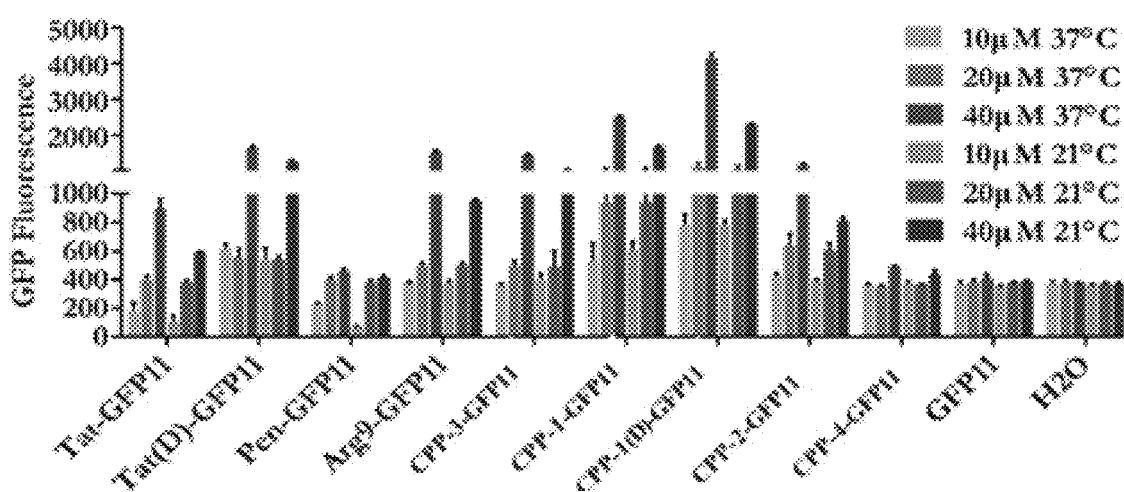

To test the ability of CPPs to deliver other cargoes, specifically a protease-sensitive peptide cargo, we modified the well-known split-GFP assay. CPPs were tested for the ability to deliver the polar 16-residue GFP-11 peptide across the membrane barrier. This peptide rescues the fluorescence of the cytosolic endogenous, non-fluorescent GFP1-10 protein. Here, we stably transfected Hela cells with a plasmid containing the full length mCherry and the non-fluorescent GFP1-10. Following incubation with CPP-GFP-11 constructs at multiple concentrations and temperatures for 30 minutes in serum free DMEM, cells were analyzed by flow cytometry for mCherry and GFP fluorescence (FIG. 17). Live cells expressing mCherry (~50% of the total cells) were gated and their GFP fluorescence was analyzed. Unlike the luciferase splice correction assay where a single corrected mRNA transcript serves as template for many molecules of functional luciferase, the split GFP assay is stoichiometric; a single GFP-11 peptide can bind to a single GFP1-10 protein producing a finite fluorescent response.

At 40 µM peptide-GFP-11, the highest concentration tested, the parent peptide Tat delivers GFP-11 to 21% and 7% of mCherry positive cells at 37° C. and 22° C., respectively. The other parent peptide, penetratin, does not measurably deliver GFP-11 under any conditions studied. The CPPs 3, 1 and 2 deliver GFP-11 to more cells than Tat and penetratin at all concentrations tested and at both temperatures tested. In fact, CPPs have a significant delivery capability at 20 and 10 µM, where both parent peptides are essentially inactive. Furthermore, the average GFP fluorescence in CPP-GFP-11 treated cells is 3-10 fold higher than Tat-GFP-11 treated cells even at 40 µM. At 20 µM, CPP-3-GFP-11, CPP-2-GFP-11, and CPP-1-GFP-11 are 6-26 fold better than Tat at 37° C. and 5-29 fold better than Tat at 22° C. At 10 µM, CPP-3-GFP-11 and CPP-2-GFP-11 treated cells exhibit background fluorescence levels however CPP-1-GFP-11 remains 44% above background at 37° C. and 72% above background at room temperature. CPP-1 is most efficient at GFP-11 delivery, followed by CPP-3 and CPP-2. Interestingly, CPP-4 does not deliver GFP-11 or TAMRA significantly, although it successfully delivers PNA705.

To test the effect of CPP proteolysis on delivery, we included in this assay D-amino acid versions of both Tat and CPP-1 attached to normal L-amino acid GFP-11 In both cases, the D-form CPPs outperformed the L-form CPPs by a moderate amount, indicating that proteolytic sensitivity has some role in delivery efficiency. At 40 µM, Tat(D)-GFP-11 outperformed Tat-GFP-11 by 2× at both 37° C. and 22° C. GFP fluorescence just above background was observed at lower concentrations for Tat(D)-GFP-11 Similarly, CPP-1 (D)-GFP-11 outperformed CPP-1-GFP-11 under all other conditions. In fact, CPP-1(D)-GFP-11 was active at 10 µM with 2.1-fold fluorescence, over background, at 37° C. and 2.2 fold increase at 22° C.

These data show that CPPs can be used to deliver polypeptides (e.g., a protein or fragment thereof) to an intracellular domain of a cell without altering the polypeptides functionality.

Example 6. Materials and Methods

Synthesis of PNA/Peptide Polymers
CPP-PNA Library
CPP-PNA library synthesis was performed using the split and combine synthesis strategy on TENTAGEL® MB NH$_2$ resin (MB300_002) loaded with Fmoc-photolabile linker (Advanced ChemTech RT1095) using standard Solid Phase Peptide Synthesis (SPPS) protocols. FMOC protected peptide (Advanced ChemTech)/PNA monomers (PNABio FMA001, FMT001, FMG001, FMC001, FM0001) were dissolved in DMF at 3× molar excess relative to the manufacturers' stated loading capacity. The reaction was catalyzed by the addition of 0.9× molar HBTU/HOBt or 0.9× molar HATU for peptides or PNAs respectively. All bases were double coupled (2×20-minute reactions) and reaction completion was demonstrated with the Kaiser test for amines. Following the addition of each base, remaining reactive sites were capped with 50× molar acetic anhydride and DIPEA. Between the peptide and the PNA, two [2-(2-(Fmoc-amino)ethoxy)ethoxy]acetic acid spacer moieties were added. Following acid deprotection in Reagent B (88% v/v trifluoroacetic acid, 5% v/v phenol, 5% v/v ddH2O, 2% v/v triisopropylsilane) supplemented with 2.5% v/v m-cresol, beads were washed thoroughly in dimethylformamide and dichloromethane and dry-cleaved from the solid support under UV light for 4 hours to produce amidated sequences. Individual beads were placed in 96-well plates, suspended in 200 µl hexafluoro-2-propanol, and placed under UV until completely dry. Cleaved peptide-PNA sequences were dissolved in 100 µl ddH$_2$O and used in subsequent luciferase/BCA assays.

CPP-PNA Positives

CPP-705 constructs and controls were synthesized using the SPPS protocols detailed previously with the following changes: 1) TENTAGEL® XV resin was used to minimize aggregation and maximize yield of the growing polymer 2) The photolabile linker was omitted 3) Following acid cleavage in Reagent B with 2.5% m-cresol, polymers were precipitated and washed 4× in ether 4) Purity and mass were verified by HPLC and MALDI-TOF 5) Constructs were lyophilized from acetic acid to remove TFA ions and stored at −20° C.

CPP—C, CPP-GFP-11 and Controls

Sequences were synthesized (Bio-Synthesis Inc.) and delivered lyophilized at a purity>90% verified by MS/HPLC. Working stocks were prepared at ~1 mM and stored at −20° C.

Tetramethylrhodamine Labeling

CPP-C sequences and controls were dissolved in DMF. Tetramethylrhodamine-5-maleimide (ThermoFisher T6027) was added at 10× molar excess and allowed to react with the sulfhydryl group of the c-terminal cysteine at room temperature for 2 hours. Excess dye was removed using cationic exchange resin (PolyLC TT1000CAT). Purity and mass were verified by HPLC and MALDI-TOF. Concentrations were determined by absorbance at 556 nm using C=89 (L/mmol*cm).

Cell Culture

Hela, RAW264.7, HCT116, HepG2, and MCF-7 cells in this study were cultured at 37° C. with 5% CO2 in Dulbecco's Modified Eagle's Medium (DMEM, Gibco) supplemented with 10% fetal bovine serum (Gibco), 1% Antibiotic-Antimycotic (Gibco), and 1% non-essential amino acids (Gibco). All assays were conducted on cells passaged fewer than 10×.

PNA705 Mediated Luciferase Splice Correction

Hela pTRE-LucIVS2-705 cells were seeded on flat-bottom 96-well plates at 10,000 cells per well in 200 µl complete DMEM. The following day, cells were washed in phosphate buffered saline and topped with premixed 50 µl 2× serum/phenol red free DMEM (Gibco)+50 µl peptide cleavage solution (ddH2O+peptide). Cells were transfected for 30 min at 37° C. with 5% CO2. The transfection solution was removed, cells were washed with PBS, and topped with 100 µl complete DMEM. The next day (24 hour recovery) cells were washed in PBS and lysed in 20 µl reporter lysis buffer (Promega E4030) following the manufacturers protocol. 10 µl of the lysate was removed and total protein concentration was determined using the bicinchoninic acid assay (Pierce BCA Protein Assay-ThermoFisher 23225). The 96-well plate containing the remaining 10 µl lysate was analyzed for luminescence using the Luciferase Assay System (Promega E1500) on a BioTek SYNERGY™ 2 plate reader with injector ports. Data was expressed as Relative Luminescence Units/µg Protein (RLU/µg Protein) and positive wells were defined as those whose RLU/µg Protein values exceeded the average for the plate by at least three standard deviations. Subsequent PNA705 delivery experiments were conducted as described above except that volumes were adjusted for 24-well plate volumes.

ALAMARBLUE° Toxicity Assay

Hela pTRE-LucIVS2 cells were plated in 96-well plates at 10,000 cells/well. After 24 hours, cells were treated with CPP constructs for 1 Hr in sfDMEM at 37° C., washed in PBS, and allowed to recover for 24 hours in 100 µl complete media. 10 µl ALAMARBLUE® (ThermoFisher) was added to each well and cells were incubated fo4r 2 Hrs at 37° C. Reduction of ALAMARBLUE® was determined by fluorescence at Em 540/Ex 590.

qRT-PCR

Hela pTRE-LucIVS2 cells treated as described above with CPP-PNA705 constructs at varying concentrations. RNA was extracted using the DIRECT-ZOL™ RNA purification system (Zymo Research) and reverse transcribed with the ISCRIPT™ cDNA synthesis kit (Bio-Rad), and mRNA splice correction was detected using PowerUp SYBR® Green master mix (ThermoFisher) on an APPLIED BIOSYSTEMS™ QUANTSTUDIO™ 6 using the following primers sets: ACTB1: 5'-CCTTGCACATGCCGGAG-3', ACTB2: 5'-ACAGAGCCTCGCCTTTG-3' pTRE-Luc IVS2 Insert: 5'-ACAGTGATAATTTCTGGGTTAAGGC-3', pTRE-Luc IVS2 Downstream: 5'-TCAATCAGAGTG-CTTTTGGCG-3', pTRE-Luc IVS2-Bridge: 5'-TTAC-GATCCCTTCAGGATTACAA-3'. The relative quantification of correctly spliced mRNA over background was calculated using the Pfaffl model.

TAMRA Delivery Assay

Hela, RAW264.7, HCT116, HepG2, and MCF-7 cells were plated in 12-well plates at 100,000 cells/well. After 24 hours, cells were gently washed in PBS, topped with 500 µl of CPP-TA solution containing 0.5 µM CPP-TA+4.5 uM CPP-C in sfDMEM without phenol red, and incubated for 30 min at either 4° C., 23° C., or 37° C. The incubation solution was aspirated and cells were treated with 100 µl 0.025% Trypsin for 3 minutes at 23° C. 500 µl DMEM containing 2% FBS, 125 nM Sytox Green, and 20 mM HEPES was used to suspend the cells. Cells were transferred to a filter-topped flow cytometry tube and analyzed on a BD™ LSR II flow cytometer. Cells displaying a normal morphology were gated and first analyzed for GFP fluorescence using the 488 nM laser. GFP negative cells were used to generate a histogram of TAMRA fluorescence, measured with the 543 nM laser. The calculated mean of this distribution and the percentage of cells exhibiting TAMRA fluorescence values higher than $10^3$ was recorded.

Confocal Microscopy

Cells were treated as described above for the TAMRA delivery assay and immediately imaged to avoid artifacts resulting from fixation. The distribution of TAMRA and Sytox Green was analyzed using a confocal scanning Nikon Eclipse Ti2 inverted microscope using a 40× oil-immersion objective. Sytox Green was excited using the 488 nM laser and TAMRA was excited using the 543 nM laser.

Split GFP Assay

Hela cells were transfected with p_mCherry-GFP1-10 (Addgene plasmid #78591) using LIPOFECTAMINE® 3000 (ThermoFisher). Single mCherry positive cells were sorted into 96-well plates using a BD™ FACSARIA™ cell sorter and colonies were maintained under G418 selection at 600 nM. Stably transfected cells were plated in 12-well plates at 100,000 cells/well and grown overnight in complete DMEM. Cells were washed in PBS and incubated in 500 µl of CPP-GFP-11 solution at variable concentrations at 23° C. and 37° C. for 30 minutes. The CPP-GFP-11 solution was aspirated and 100 µl of 0.025% trypsin solution was added to each well. After detachment, cells were suspended in 500 µL of PBS+2% FBS and 20 mM HEPES. Cells were analyzed using a BD™ LSRII flow cytometer. Cells displaying a normal morphology were gated and first analyzed for mCherry fluorescence using the 543 nM laser. mCherry+ cells were used to generate a histogram of GFP fluorescence measured with the 488 nM laser. The calculated mean of this distribution and the percentage of cells exhibiting GFP fluorescence values higher than $10^3$ was recorded.

Example 7. Diagnosing a Medical Condition Using a CPP Conjugate

A CPP bound to a cargo, including but not limited to a therapeutic or imaging agent, can be used to diagnose the presence of a medical condition (e.g., a disease) in a subject. For example, the cargo of the CPP can an agent that can act as a reporter in a cell that signifies the presence of a medical condition. The CPP-conjugate with a reporter can be incubated with a sample (e.g., cells or tissue) from the subject suspected to have or at risk of having the medical condition (e.g., a metabolic condition in which the subject lacks a functional enzyme that results in toxic accumulation of a substrate of the enzyme).

For example, the reporter conjugated to a CPP can be an enzyme that is not produced in the sample from the subject due to the diseased state (e.g., the absence of the enzyme glucocerebrosidase in Gaucher disease, which results in excessive accumulation of lysosomal glucocerebroside). The effect following the internalization of the CPP-enzyme conjugate within the cell can be observed, such as the production of a cleavage product of the enzyme, which would indicate that the subject has the metabolic condition.

In another example, the reporter conjugated to a CPP can be the substrate of an enzyme that is not produced in a metabolic disease. Contacting the CPP-conjugate with the enzyme substrate in the sample (e.g., cells or tissue) from the subject will result in the absence of, or reduced cleavage in a subject with the metabolic disease, and cleavage of the substrate in a subject without the disease. This readout can be used to diagnose the presence or absence of the metabolic disease.

Example 8. Treating Cancer Using a CPP Conjugate

A CPP bound to a cargo, including but not limited to a therapeutic or imaging agent, can be used to treat a subject that has been diagnosed with a medical condition (e.g., a cancer). For example, a subject having glioblastoma, a cancer which is characterized by an up regulation of miR-10b, can be treated by the administration of a CPP conjugated to an antisense miR-10b nucleotide. Upon administering the CPP-antisense miR-10b conjugate to the subject, the CPP antisense miR-10b conjugate would be internalized into the cell, bind to, and down regulate, the miR-10b of the glioblastoma, thus treating the glioblastoma.

Example 9. Treating a Metabolic Disorder Using a CPP Conjugate

A CPP-conjugate can also be used to treat a metabolic disorder. For example, aberrant cholesterol export can lead to the accumulation of toxic levels of cholesterol within peripheral cells. Cholesterol transport is mediated by ATP-binding cassette transporters, which can be down regulated by excess miR-33a in certain metabolic disorders. A subject diagnosed with a metabolic disorder characterized by an over expression of miR-33a could be treated by a CPP-antisense miR-33a conjugate. The CPP-miR-33 conjugate could be administered to a subject in an effective amount (e.g., an amount sufficient to mitigate disease, alleviate a symptom of disease and/or prevent or reduce the progression of disease). The effect following cellular internalization would be inhibition of miR-33, and an improvement in the symptoms and/or reduction in the progression of the disease.

Following administration of the CPP conjugate to a subject, a practitioner skilled in the art can monitor the subject's improvement in response to the therapy by a variety of methods. For example, a physician can monitor the overall cholesterol levels or the symptoms of aberrant lipid metabolism (e.g., the expression of ABC transporters, HDL generation, and fatty acid degredation).

Example 10. AMP Library Synthesis

Figure 18:
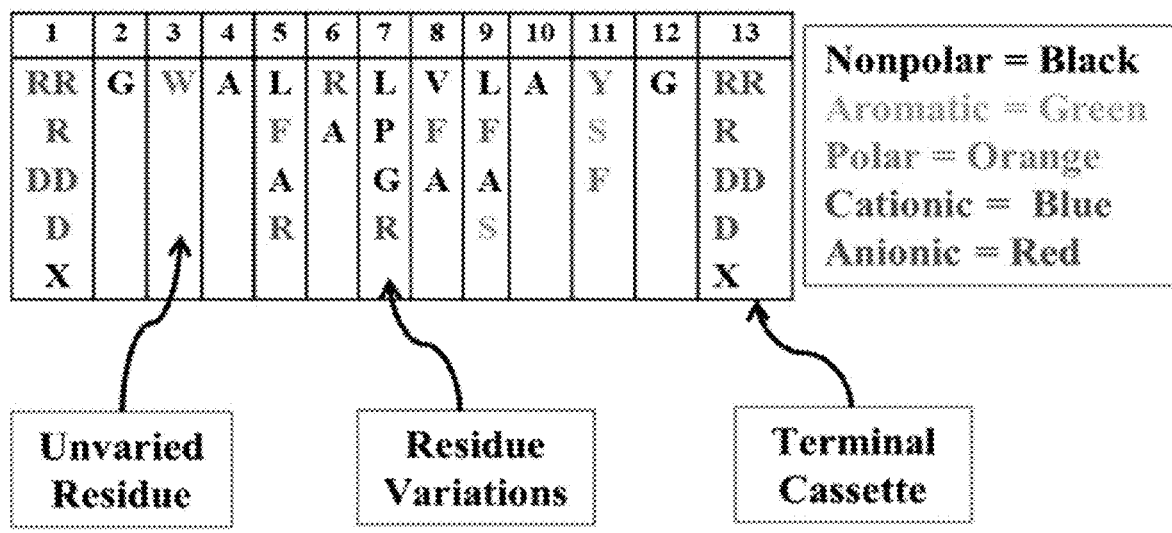
FIG. 18 is a schematic showing the ARVA (SEQ ID NO: 40)-based iterative combinatorial library. The library has 8 potential combinatorial sites yielding a total of 28,800 unique members. Members were synthesized using SPPS principles for Fmoc-protected amino acids. To enable separation of individual peptides macro-sized solid support resin was used.
Figure 19:
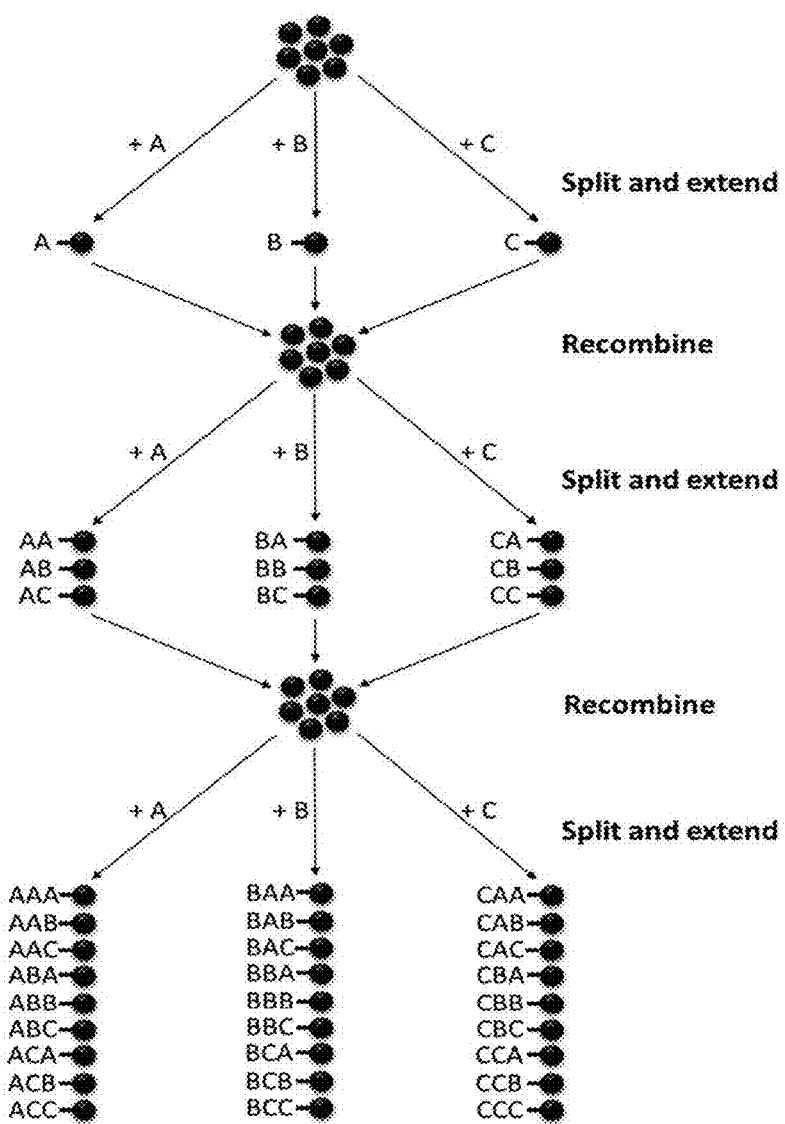
FIG. 19 a schematic showing the split and recombine approach to peptide synthesis. Library synthesis begins with a single pool of synthesis resin that is physically composed of small (~0.3 mm) spherical beads. When a residue is added the full pool is split into a set of sub-pools equal to the number of possible residues, in this example 3. A unique residue is coupled to each sub-pool, after which the pools are recombined into a single unit. The end result of three unique residues for a three amino acid peptide is 27 (3×3×3).
Figure 20A:
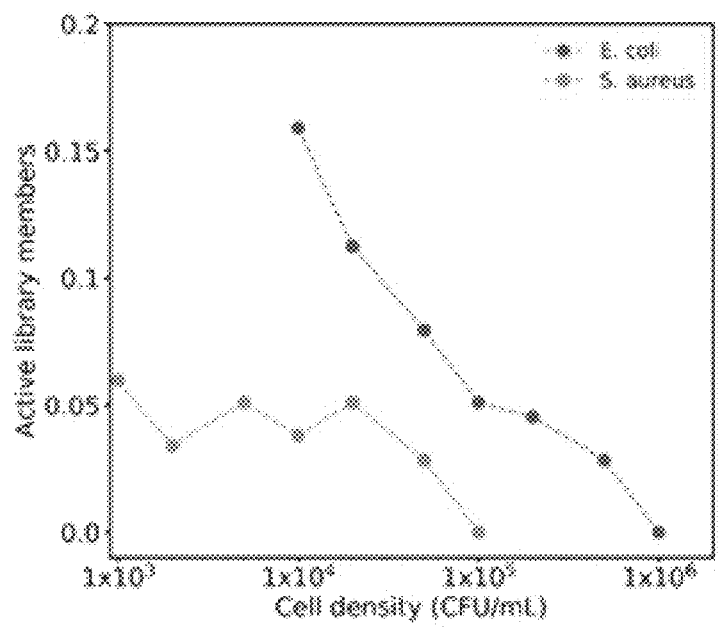
FIGS. 20A-20C show plots profiling the activity of the peptide library by the number of peptides with sterilizing activity.
Figure 20B:
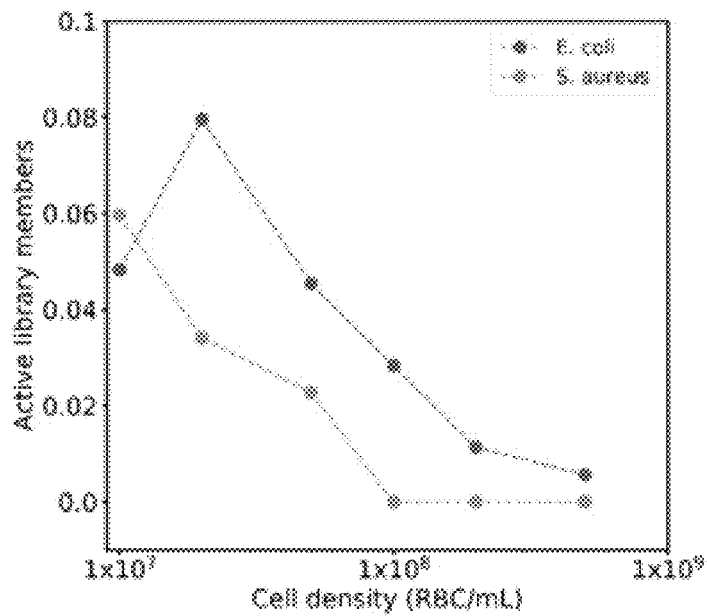
Figure 20C:
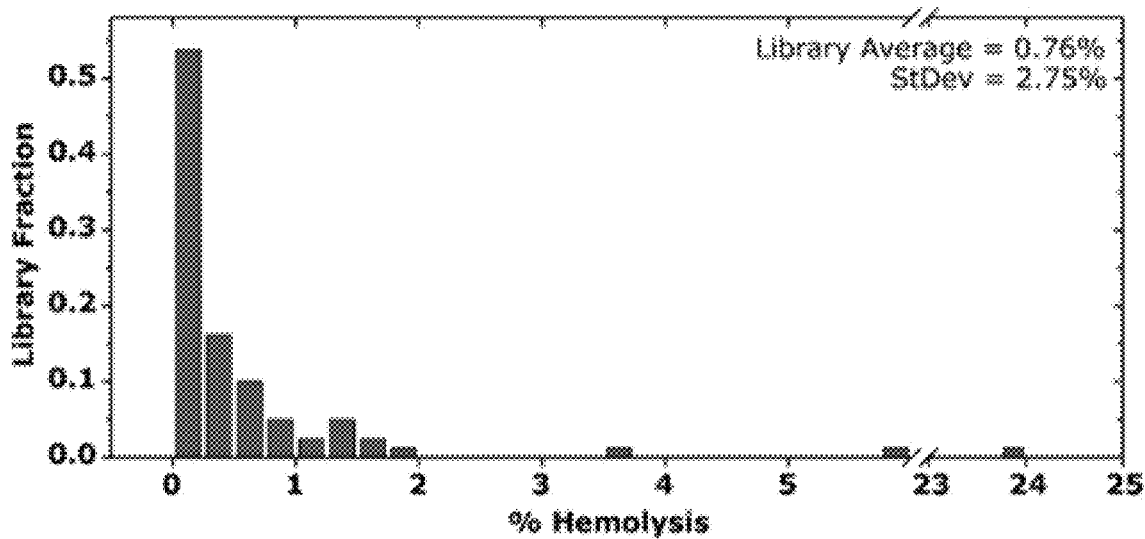
Figure 21A:
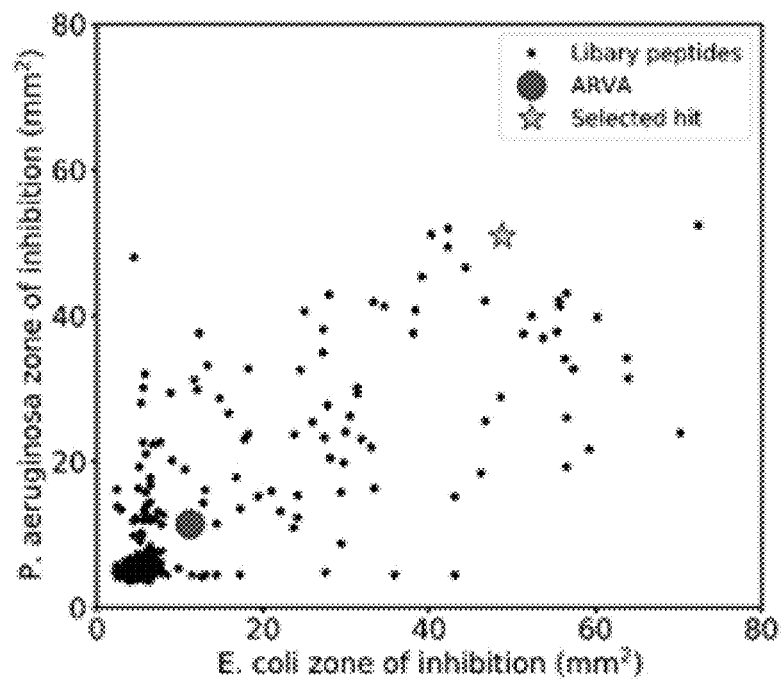
FIGS. 21A-21D are plots showing the results of peptide library screening using radial diffusion assays. Extracted peptides were divided into equal aliquots and incubated for 30 minutes with either PBS or RBCs at a concentration of $1\times10^8$ cells/mL. After incubation, the solutions were transferred to a 96-well agarose plate to assess their ability to inhibit the growth of bacteria. Two iterations of the screen were performed, one against *E. coli* and *P. aeruginosa* and another against *P. aeruginosa* and methicillin-resistant *S. aureus* (MRSA). A total of 768 peptides were assayed, 384 in each screen. Two peptides were isolated and are indicated by star symbols in these plots.
Figure 21B:
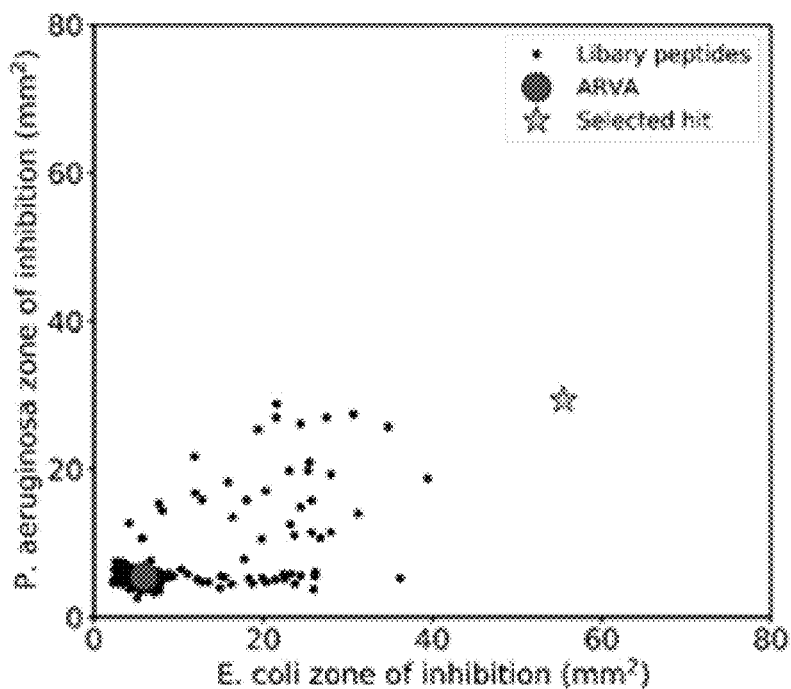
Figure 21C:
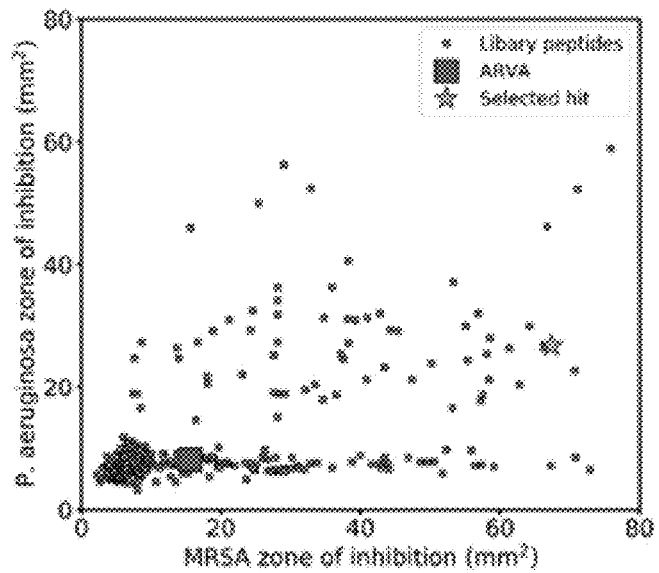
Figure 21D:
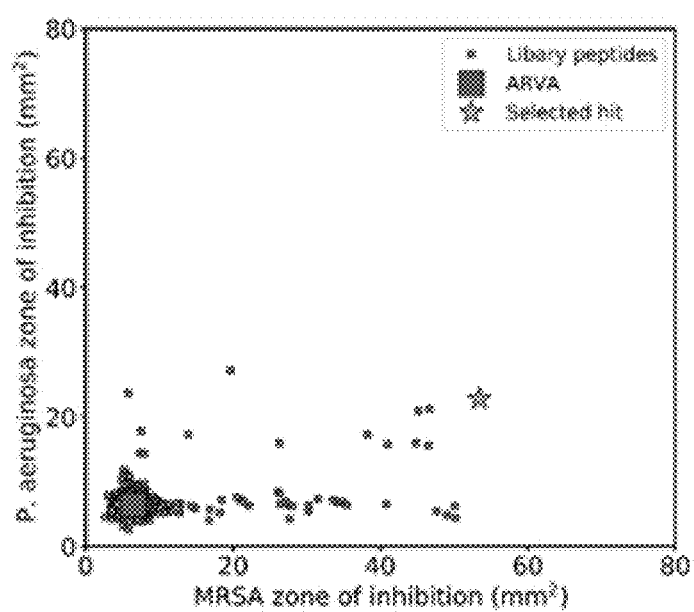

The combinatorial peptide library was synthesized on TENTAGEL® mega beads from Rapp Polymere. Before library synthesis, the loading capacity of the resin was amplified by the conjugation of lysine dendrimers. After each lysine is added, the side chain and N-terminal protecting groups were removed such that two additional lysine residues could be added. This process was repeated three times to increase the loading capacity of the bead eight-fold. Prior to addition of amino acids, a UV-sensitive photo-labile linker was added to allow the peptides to be cleaved from the resin by exposure to UV-light. The library was synthesized using the split-combine strategy for combinatorial sites (FIGS. 18-19). Residues were added using standard SPPS principles for FMOC protected amino acids. Briefly, FMOC is removed from the N-terminus of the growing peptide by treatment with 30% piperdine in DMF. The C-terminus of the next residue is activated in situ with HBTU/HOBt in DIPEA/DMF. When synthesis is complete, the side chains are deprotected with Reagent B (triflouroacetic acid (88%), phenol (5%), water (5%), triisopopylsilane (2%)).

Example 11. Minimum Sterilizing Concentration in the Presence of RBCs

Antibiotics were prepared at 5-times the final concentration needed in 0.025% acetic acid in H2O. The antibiotics were serially diluted by a factor of 2:3 horizontally across a 96-well, canonical-bottomed plate, 25 µL per well. One column was reserved for controls. RBCs at 0, $2.5 \times 10^9$, w.$5 \times 10^8$, and $2.5 \times 10^7$ cells/mL were added in 50 µL aliquots to the appropriate wells. Following a 30-minute incubation, 50 µL of TSB, inoculated with $5 \times 10^5$ CFU/mL, was added to all wells, and plates were incubated overnight at 37° C. To assess bacterial growth, a second inoculation was performed with 10 µL of solution from the original plate added to 100 µL of sterile TSB. Following overnight incubation at 37° C., the OD600 was measured (values of less than 0.1 were considered sterilized). (FIGS. 20, 24, 25, and 27)

Example 12. Radial Diffusion in the Presence of RBCs

Underlay agarose was prepared by adding 5 g of low EEO agarose and 0.03 g of TSB to 500 mL of 10 mM phosphate buffer (pH=7.4). Overlay agarose was prepared by adding 5 g of low EEO agarose and 30 g of TSB to 500 mL of 10 mM phosphate buffer (pH=7.4). Both solutions were heated until the agarose melted and then were autoclaved. To a rectangular, one-well plate, 20 mL of underlay agarose, inoculated with $8\times10^6$ CFUs of bacteria, was added. A sterile, 96-well plate replicator from Sigma-Aldrich was set in the molten agarose and removed one the agarose solidified. Antibiotic was prepared at 4 times the final desired concentration. For the antibiotic standard, a serial dilution of 3:4 across a 96-well plate was performed followed by 1:4 dilution with PBS. Otherwise, the peptide was diluted to 20 µM with RBCs and/or serum to give between 2% ($1\times10^8$ cells/mL) and 20% ($1\times10^9$ cells/mL). Solutions were incubated with gentle shaking for 30 minutes at 37° C. for 3 hours. Overlay was added, and the plate was incubated upside down overnight. Surface growth was cleared, the plates were sterilized with 25% methanol and 5% acetic acid. Zones of inhibition were photographed and analyzed using ImageJ. (FIG. 21)

Example 13. Hemolysis Assay

Figure 22A:
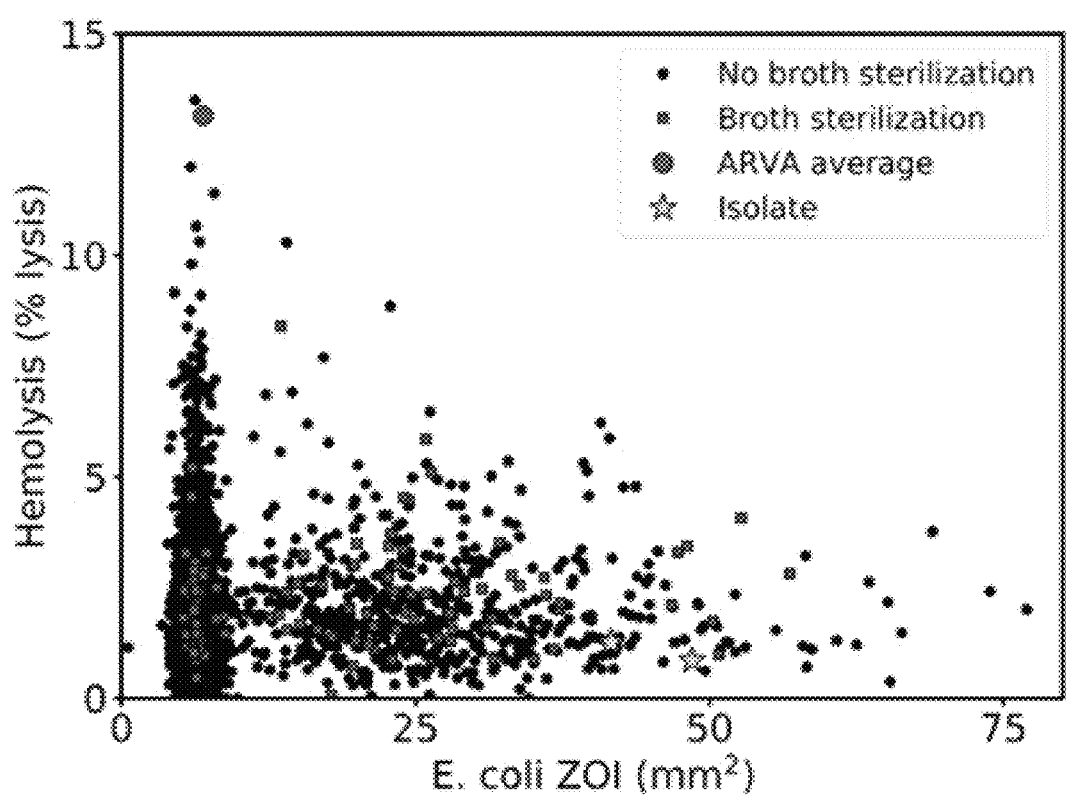
FIGS. 22A-22C AMP library screening with radial diffusion and broth dilution.
Figure 22B:
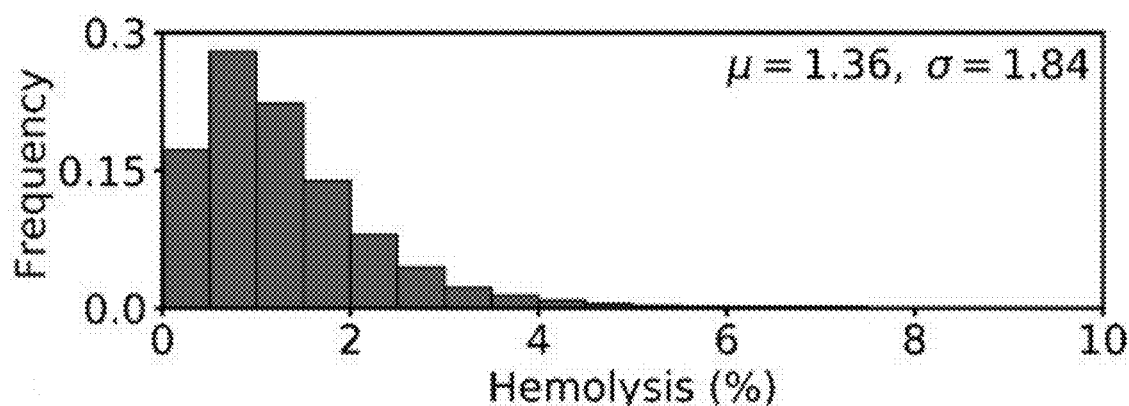
Figure 22C:
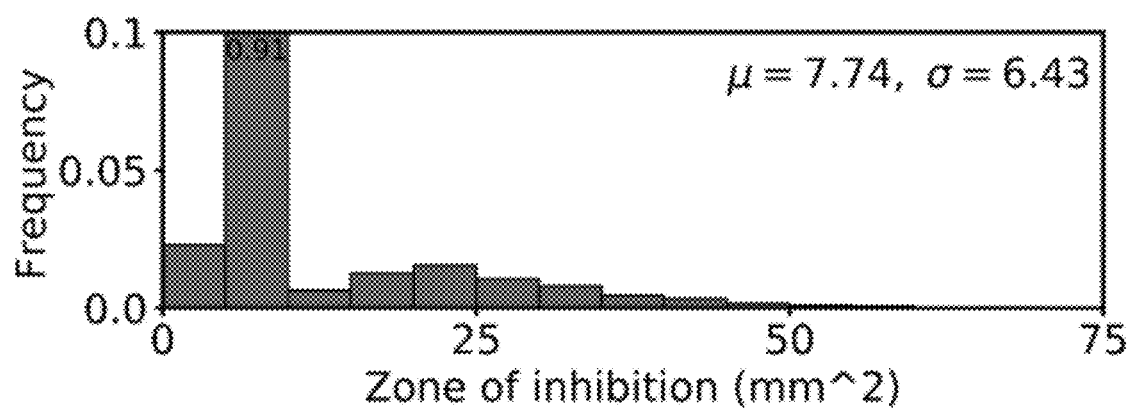
Figure 23:
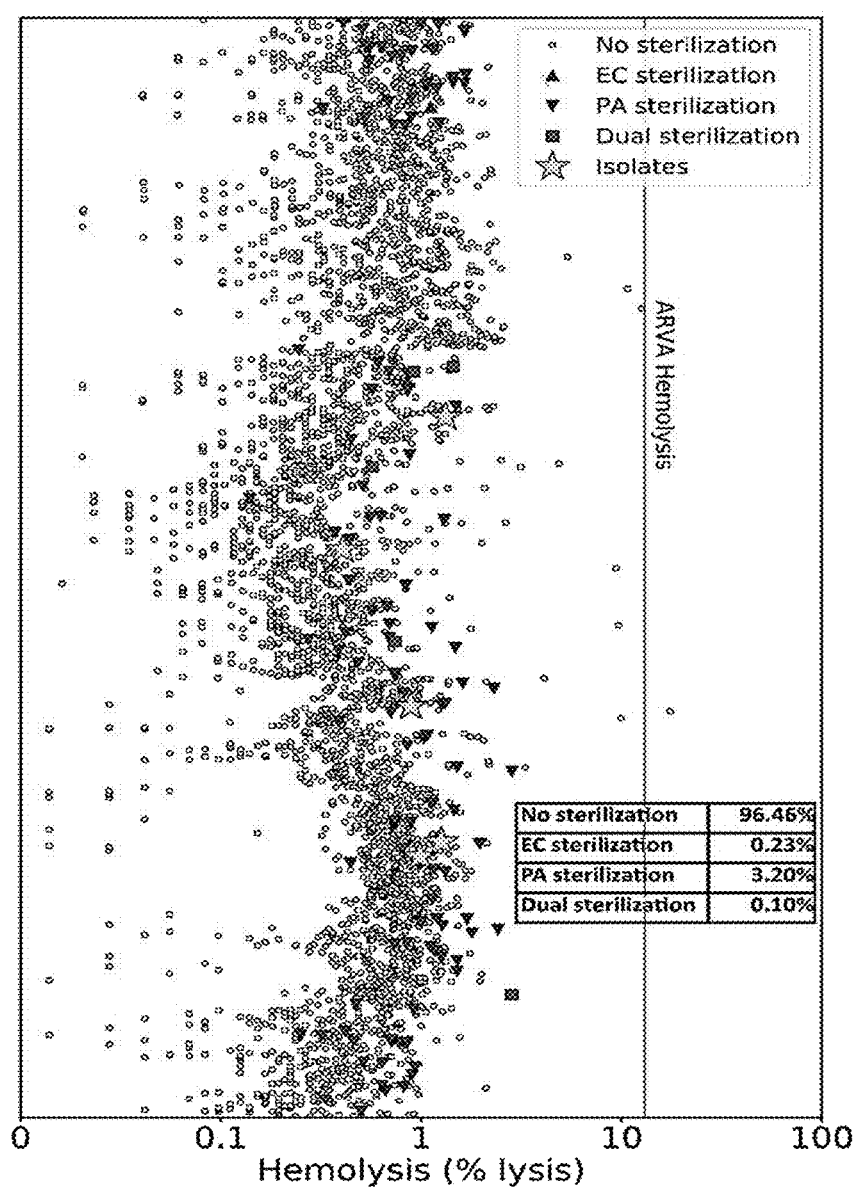
FIG. 23 is a plot showing the results of a library screening using only broth dilution in the presence of RBCs.
Figure 24A:
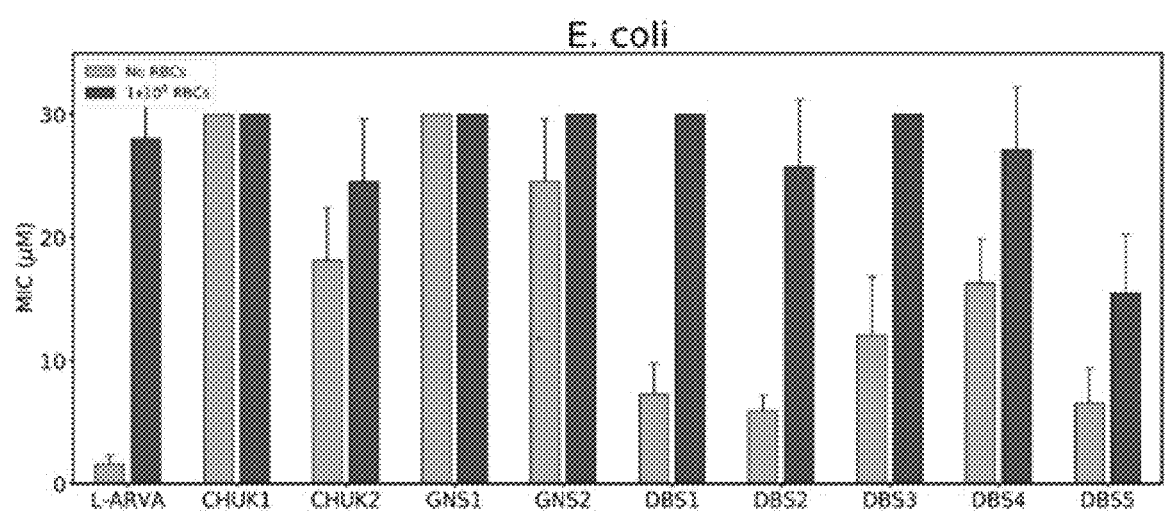
FIGS. 24A-24C show the activity of selected AMPs against microbial growth.
Figure 24B:
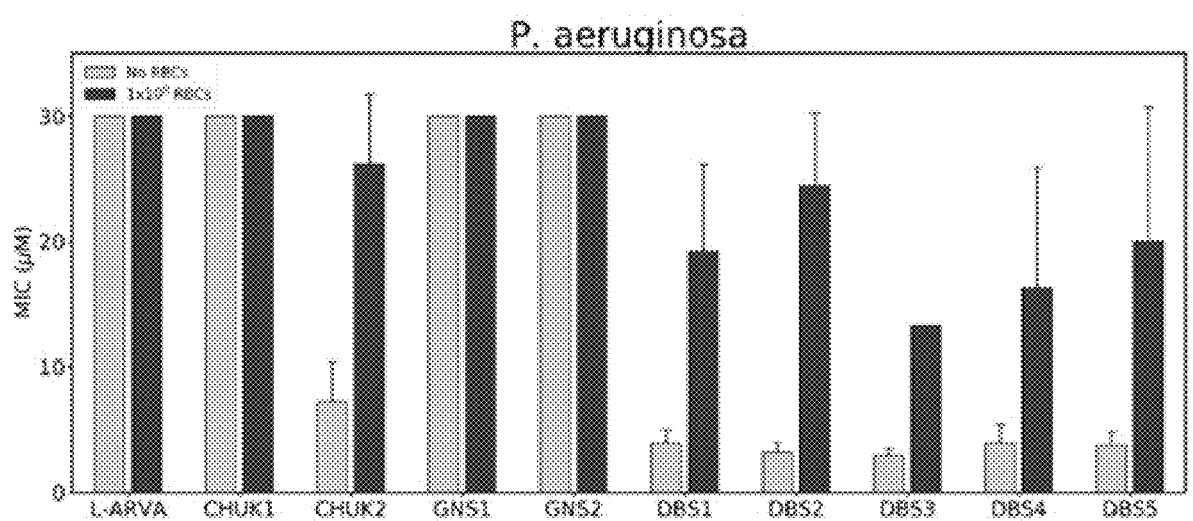
Figure 24C:
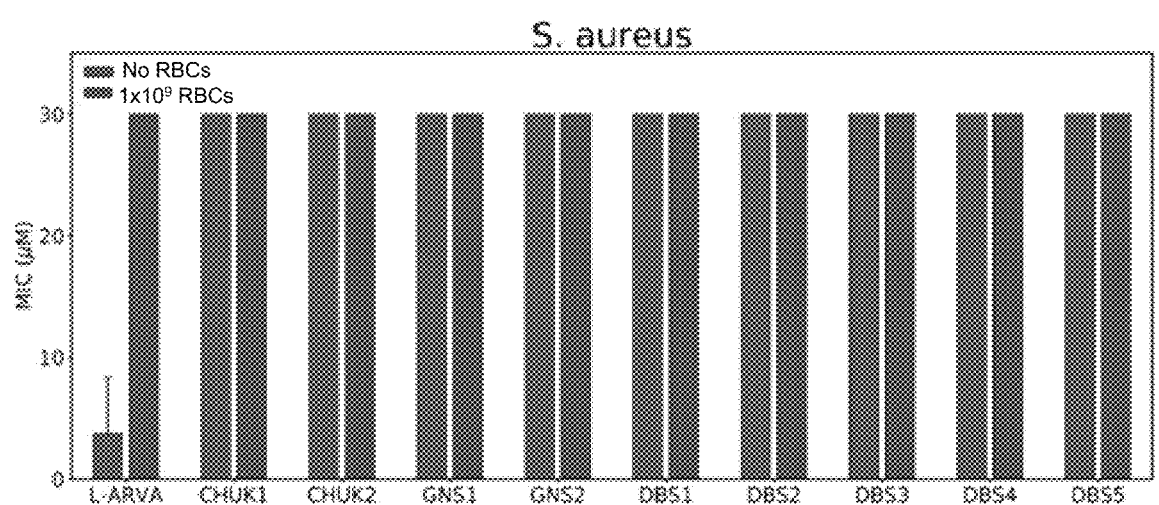
Figure 25A:
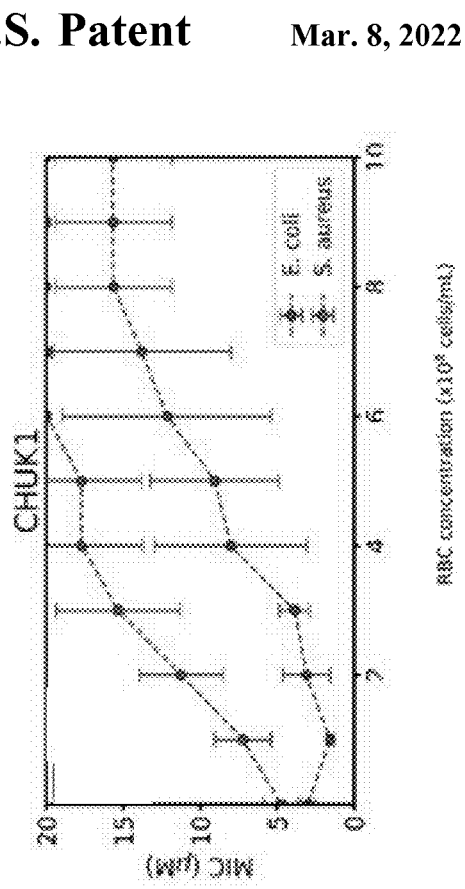
FIGS. 25A-25J show post-screening characterization of isolated amps in radial diffusion assays.
Figure 25B:
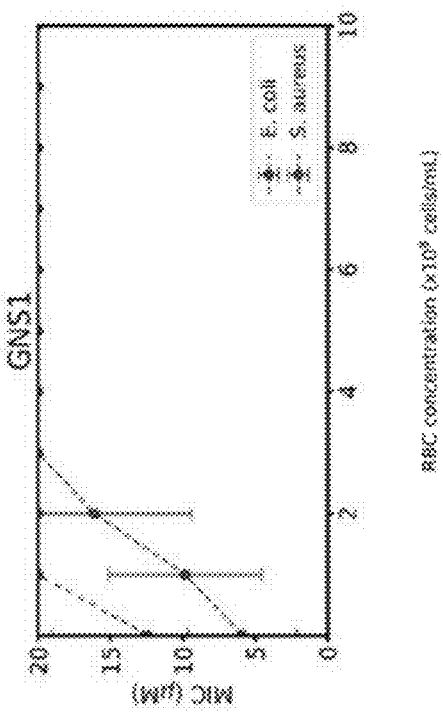
Figure 25C:
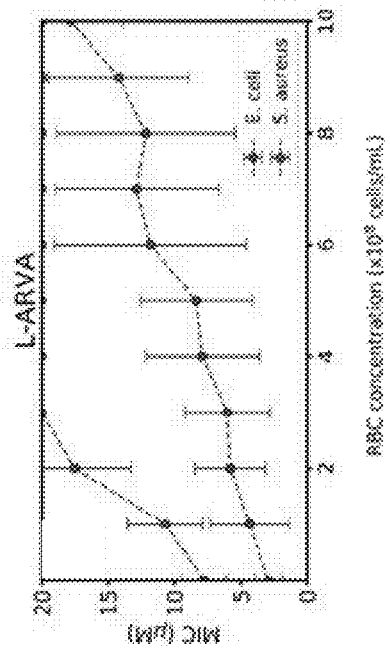
Figure 25D:
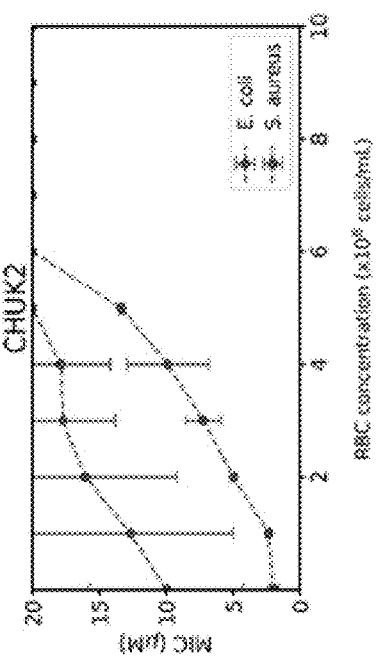
Figure 25E:
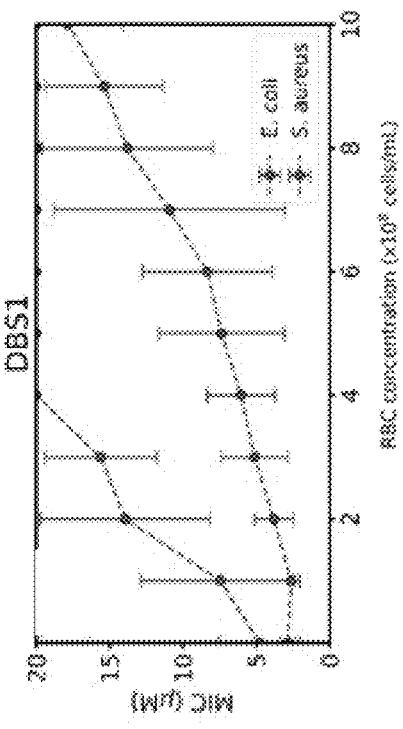
Figure 25F:
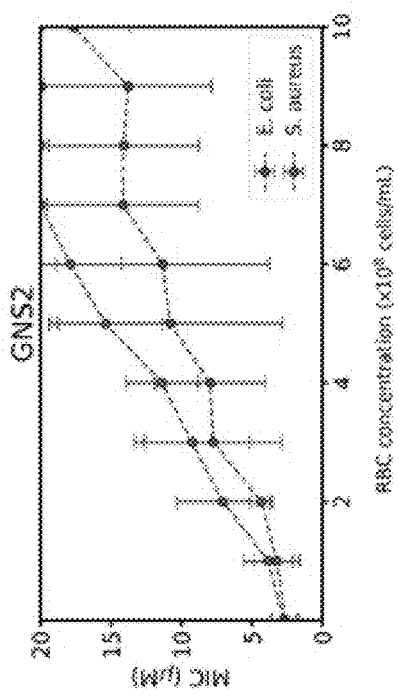
Figure 25G:
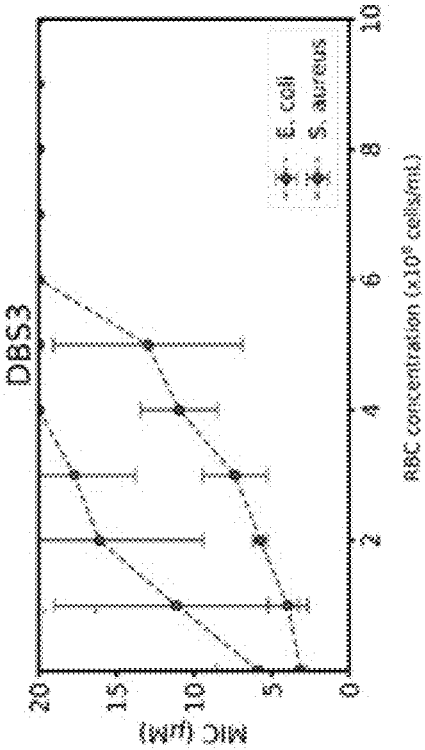
Figure 25H:
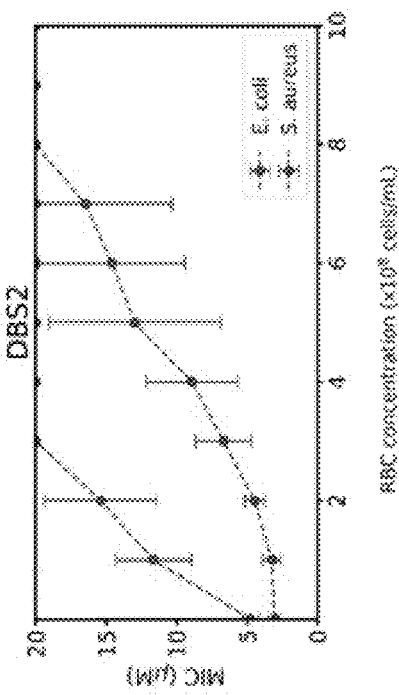
Figure 25J:
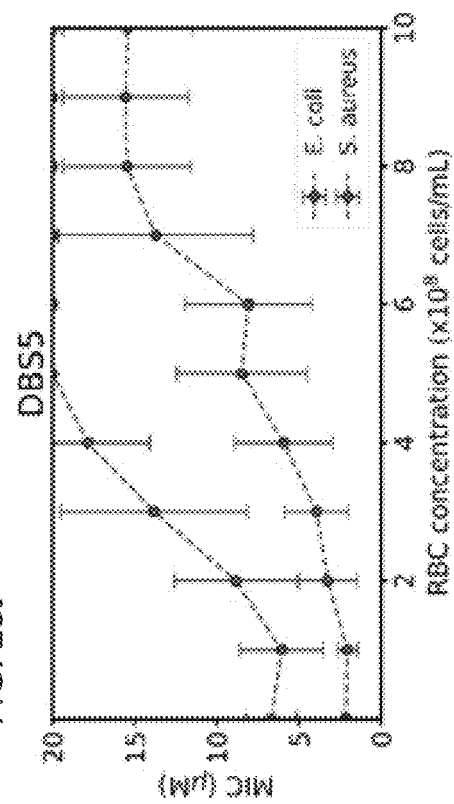
Figure 25I:
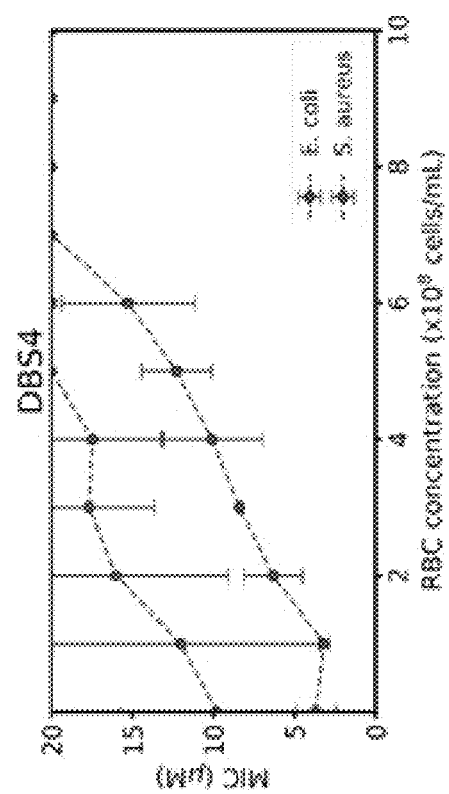
Figure 26A:
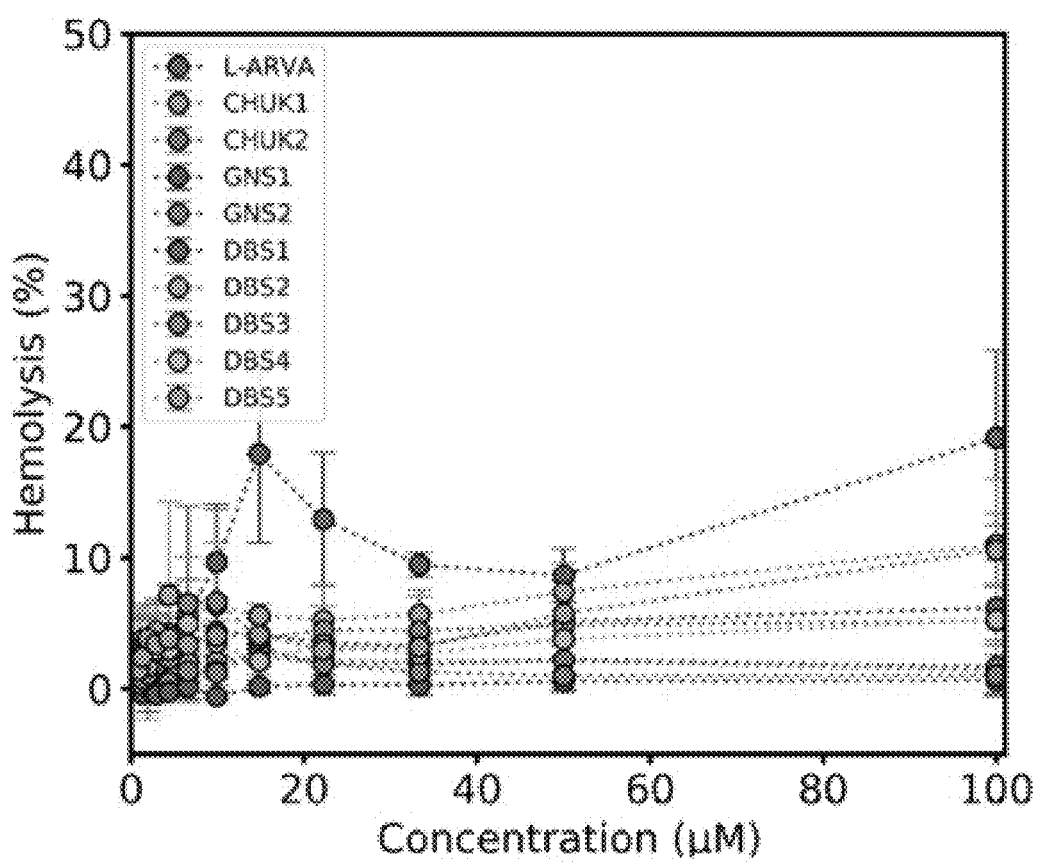
FIGS. 26A-26B show post-screening cytotoxicity assays of library isolates. The peptides isolated from the library were assayed for toxicity.
Figure 26B:
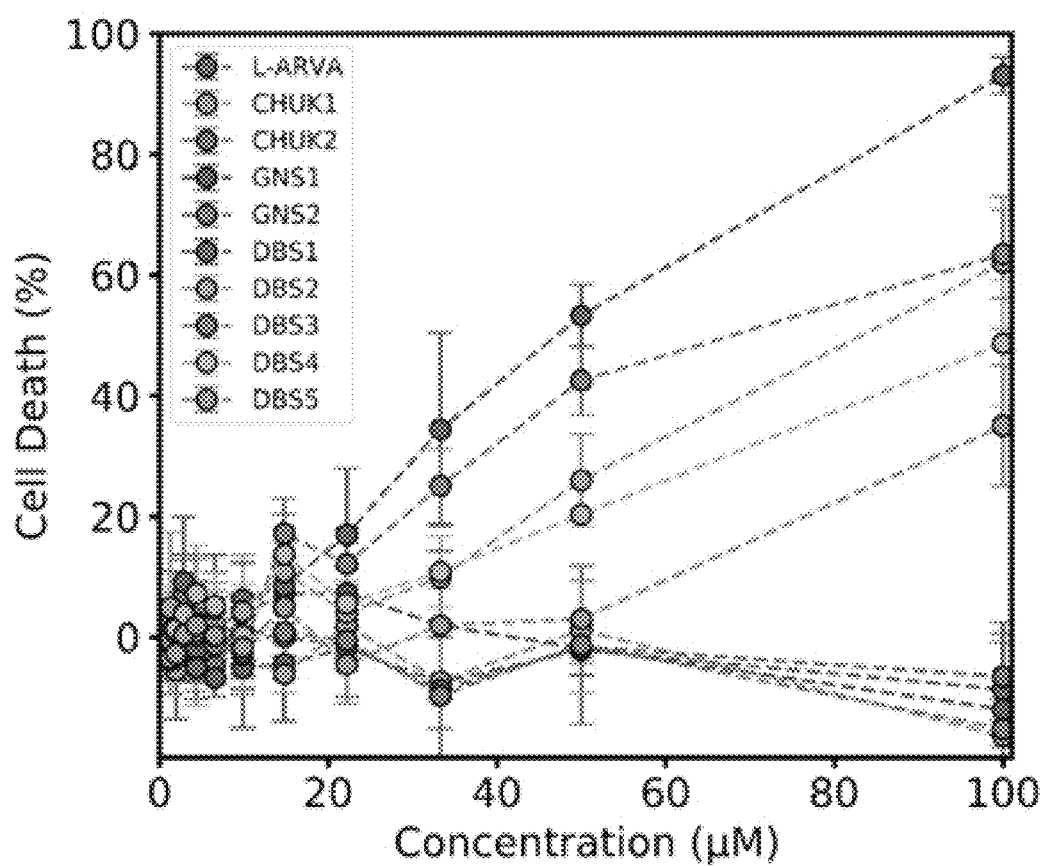
Figure 27A:
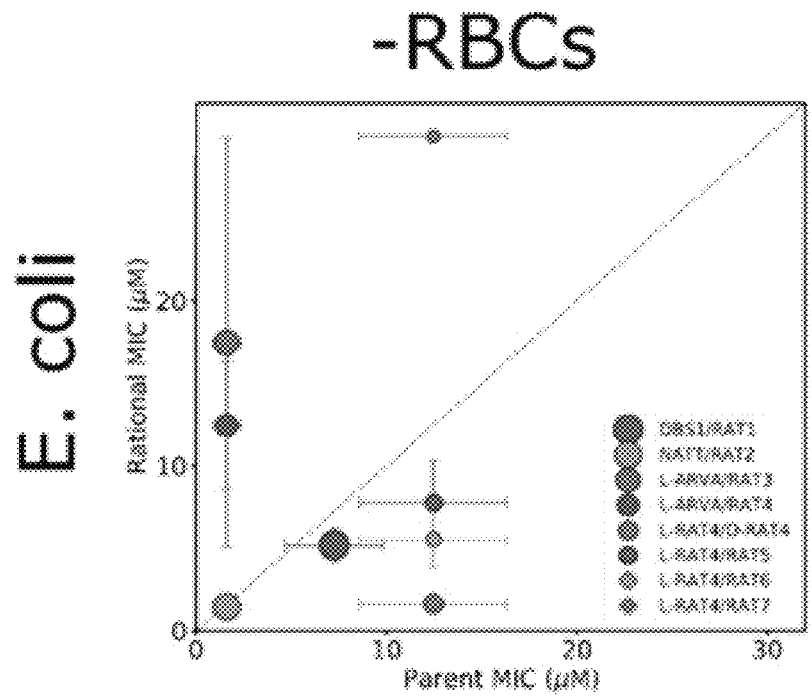
FIGS. 27A-27F are plots showing the results from a broth-based MIC assay. AMPs were tested to determine the minimum inhibitory concentrations in the absence and presence of $1\times10^9$ RBCs/mL. The MIC values of the parent peptides are plotted on the x-axis and the engineered sequences on the y-axis. Improvements in the peptide MIC are apparent in points plotted below the gray-dashed line (y=x).
Figure 27B:
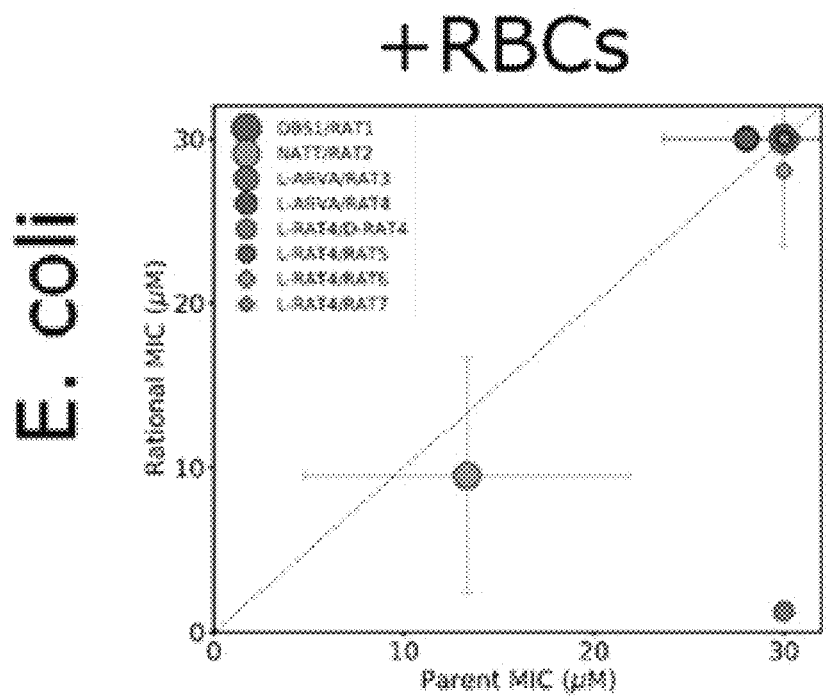
Figure 27C:
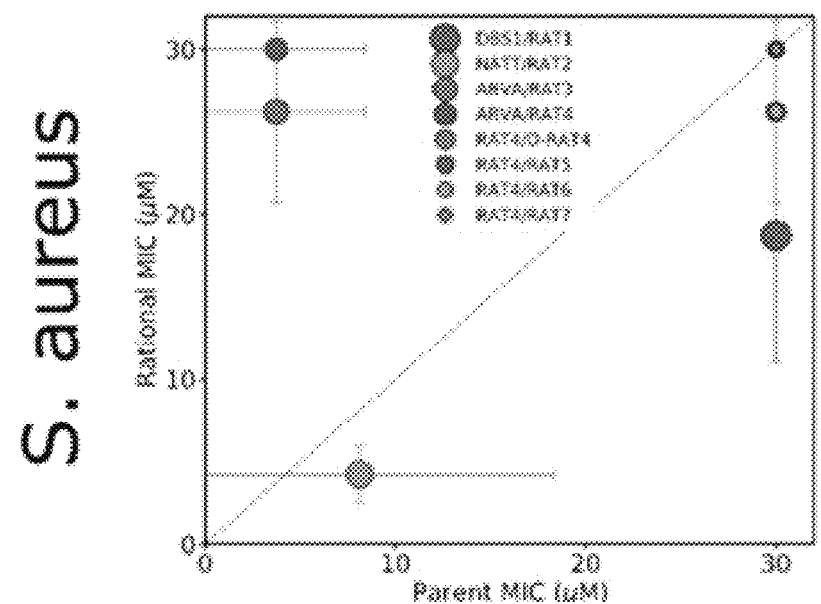
Figure 27D:
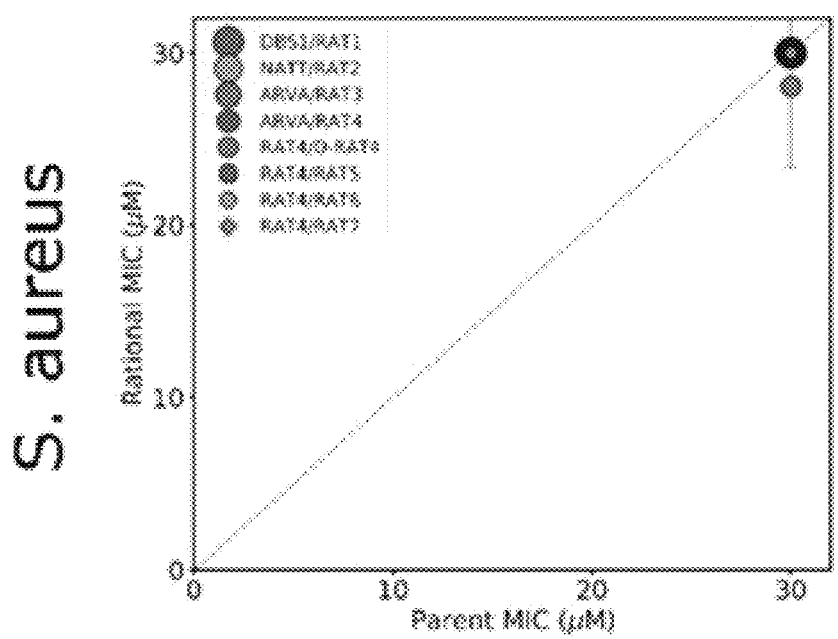
Figure 27E:
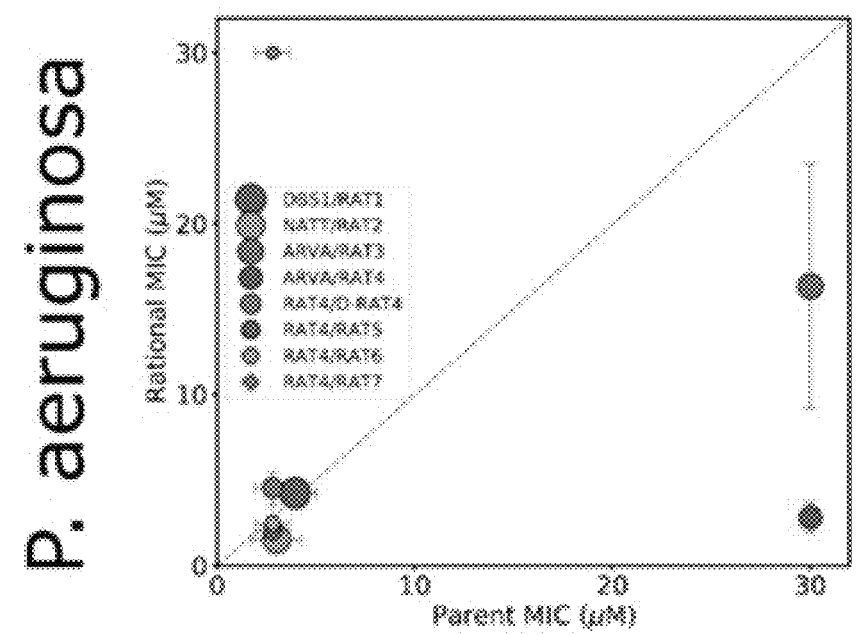
Figure 27F:
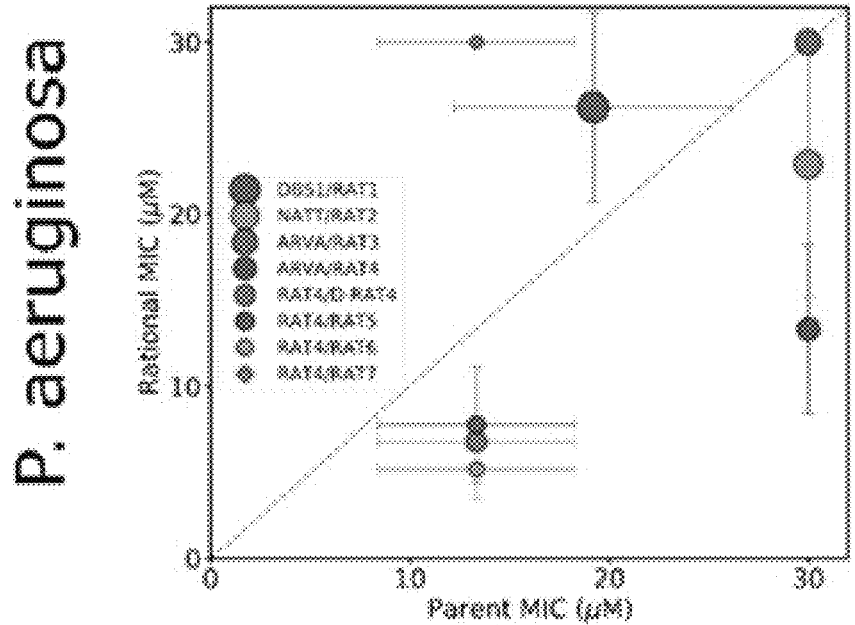

Peptide was serially diluted in PBS starting at a concentration of 100 µM. The final volume of each peptide in each well was 50 µL. To each well, 50 µL of RBCs in PBS at $2\times10^8$ cells/mL was added. As a positive lysis control, 1% TRITON™ was used. The mixtures were incubated at 37° C. for 1 hour, after which they were centrifuged at 1000×g for 5 minutes. After centrifugation, 10 µL of supernatant was transferred to 90 µL of DI $H_2O$ in a fresh 96-well plate. The absorbance of released hemoglobin at 410 nm was recorded and the fractional hemolysis was calculated based on the 100% and 0% lysis controls. (FIGS. 22, 23, and 26)

Example 14. CFU Reduction Assay

Peptide was prepared at 5× the final concentration in 0.025% acetic acid and 30 µL was added to a single well of a 96-well plate. A bacterial suspension was prepared in PBS at $2.5\times10^9$ cells/mL. PBS or RBCs at $2.5\times10^9$ cells/mL were added to peptide in a volume of 60 µL. The plates were then incubated at 37° C. for 1 hour. The mixtures were then serially diluted 1:10 and the dilutions were spotted on TSB agar. The agar plates were incubated at 37° C. overnight and colonies were counted the next day to determine the efficacy of the AMPs in the presence and absence of RBCs.

Example 15. Peptide Extraction

Beads were affixed to petri dishes by adding a small amount of methanol to a pool of resin beads and allowing it to evaporate. The beads were then "pre-cleaved" by exposure to UV light for five hours. Prior to use in an antimicrobial assay(s), 30 µL of 0.025% acetic acid is added to each well of a 96-well plate. Individual beads are picked from the petri dish using forceps and placed in a well (one bead per well). To each well, 30 µL of HFIP was added, and the plate was then incubated under UV-light with shaking for 2 hours (until the solvent evaporated). Next, 35 µL of PBS was added to all wells and the plates were placed on a shaker overnight. Prior to an assay, the peptide solutions were transferred to a fresh 96-well plate to separate peptide solution from synthesis resin and the extraction plates were stored for indexing. The average concentration of extracted peptide was ~15 µM.

Example 16. Mixed Radial Diffusion Broth Dilution Screen

To 30 µL of extracted peptide in a 96-well plate, 6 µL of RBCs at $6\times10^9$ cells/mL was added and the plates were incubated for 1 hour with shaking at room temperature. Following incubation, the plates were centrifuged at 1000×g for five minutes to pellet the cells. Five microliters of supernatant was removed from the plate and added to 60 µL of PBS in a second plate. This plate was read at 410 nm for hemolysis. Next, the cells were resuspended and 10 µL of the solution were added to a radial diffusion plate harboring E. coli. These plates were process as described above in Example 12. To the remaining 20 µL of peptide/RBC solution, 20 µL of P. aeruginosa at $5\times10^5$ CFU/mL in 1% TSB in PBS was added. The plate was allowed to incubate for 3 hours at 37° C. Following incubation, 40 µL of 2×TSB was added and the plate was incubated at 37° C. overnight. Because of the presence of dense RBCs, inhibition of bacterially growth was initially detected by a lack of deoxygenation in the wells (as evidenced by RBC coloration). Wells that were suspected to have been inhibited had an aliquot removed and spread on a TSA plate. These plates were incubated at 37° C. to verify the presence/absence of microbes.

Example 17. Sequence Identification

The synthesis resin of peptides selected from the screen was retained from the indexing plate. Each positive bead was analyzed via Edman degredation.

Example 18. Cytotoxicity Assay(s)

CCLP-1 cells were grown to confluency in T-75 flasks in complete DMEM (10% FBS). The day prior to cytotoxicity experiments, cells were trypsinized, removed from the flask, and pelleted at 1000×g. The trypsin and spent media were discarded and the cells were resuspended in complete DMEM. The cell count was obtained using a standard hemocytometer. The cells were then seeded at a density of $3.5\times10^4$ cells/well in a 96-well tissue-culture plate. In a separate 96-well plate, peptide was serially diluted in serum-free DMEM starting at a concentration of 100 µM. The final volume of peptide in each well was 100 µL. To perform the cytotoxicity assay, media was removed from the wells and replaced with the peptide/DMEM solutions. No peptide and 20 µM melittin in serum-free media were used as negative and positive controls, respectively. The cells were then incubated for one hour in a standard tissue-culture incubator. After this incubation, 10 µL of ALAMARBLUE® assay reagent was added to each well in the plate and the plate was returned to the incubator. After two hours of additional incubation, the plate was read for fluorescence with an excitation wavelength of 530 nm and an emission wavelength of 590 nm. The cytotoxicity was calculated based on the 100% and 0% lysis controls. (FIG. 26).

Example 19. Sequence Design, Underlying Hypotheses, and Statistical Analysis for Rationally Engineered Peptides The engineered peptide sequences and their derivation from parent sequences is shown, along with the underlying hypothesis described for the first set of peptides (Table 4) and the second set (Table 5). We performed statistical testing for performance in antimicrobial assays in the presence and absence of RBCs, as well as for cytotoxicity. The broth dilution results were tested using a two sample t-test (N=6-22). The radial diffusion results were tested using a paired t-test (N=4). The cytotoxicity results were tested using a paired t-test (N=3). The ↑ represents the improvement in performance that would be desired for a viable in vivo antimicrobial peptide. This corresponds to a decrease in MIC values (increased potency) and decreased cytotoxicity. The symbol represents a regression in desired behavior. (*=p<0.05, =p<0.01, *=p<0.001). Our results show the promise for rationally designed peptides, and the efficiency in experimental deisng.

TABLE 4

| Peptide | Sequence | Hypothesis | Significant Results |
| --- | --- | --- | --- |
| RAT1 | (DBS1)<br>RRGWARRLFFAYGRR<br>↓<br>RRWARRLFFAYRR | The presence of glycine in the sequence of DBS1 is not necessary and increases the complexity of synthesis. Removal of G will not reduce the activity of the peptide and may actually increase the activity by increasing both hydrophobicity and positive charge, relative to the length of the sequence. | ↑Broth vs.<br>S. aureus (−RBC)<br>↑Radial Diffusion vs.<br>S. aureus<br>↑Radial Diffusion vs.<br>E. coli*<br>↑Cytotoxicity vs.<br>CCLP-1** |
| RAT2 | (NATT)<br>RRGWNLALTLTYYGRR<br>↓<br>RRWNLALTLTYYRR | The presence of glycine in the sequence of NATT is not necessary and increases the complexity of synthesis. Removal of G will not reduce the activity of the peptide and may actually increase the activity by increasing both hydrophobicity and positive charge relative to the length of the sequence. | ↑Broth vs.<br>P. aeruginosa (−RBC)*<br>↑Broth vs.<br>P. aeruginosa (+RBC)*<br>↓Hemolysis* |
| RAT3 | (ARVA)<br>RRGWALRLVLAY<br>↓<br>RRGWALRLVLAYGRR | A library based on the sequence of ARVA yielded all peptides with two arginine residues at both termini. These new peptides are less potent, but also less toxic, and some perform better in the presence of RBCs. Adding a cassette to ARVA will reduce its toxicity and interaction with RBCs while leaving the potent antimicrobial activity intact. | ↓Broth vs.<br>E. coli (−RBC)*<br>↓Broth vs.<br>S. aureus (−RBC)*<br>↓Hemolysis* |
| RAT4 | (Library Consensus)<br>RRGWARRLAFAFGRR | The consensus sequence will retain important features from each peptide in the library and thus perform better in terms of potency and minimizing interactions with RBCs. Note that residues 9 and 10 both had the potential to be A or F; we selected A at position 9 and F and position 10. | ↓Broth vs.<br>E. coli (−RBC)*<br>↓Broth vs.<br>S. aureus (−RBC)*<br>↑Broth vs.<br>P. aeruginosa (−RBC)<br>↑Broth vs.<br>P. aeruginosa (+RBC)*<br>↑Radial Diffusion vs.<br>S. aureus*<br>↑Hemolysis* |
| D-RAT4 | (Library Consensus)<br>rrgwarrlafafgrr | The library peptides are being impacted by proteolysis. Synthesizing the consensus sequence with D-amino acids will yield a peptide that retains activity more faithfully in the presence of RBCs. | ↑Broth vs.<br>E. coli (−RBC)*<br>↑Broth vs.<br>E. coli (+RBC)*<br>↓Broth vs.<br>P. aeruginosa (−RBC)*<br>↑Broth vs.<br>P. aeruginosa (+RBC)*<br>↑Radial Diffusion vs.<br>E. coli<br>↑Radial Diffusion vs.<br>S. aureus* |
| RAT5 | (Library Consensus)<br>RRGWARRLAFAFGRR<br>↓<br>RRGWARRLRLAFAFGRR | The presence of RL at positions 7 and 8 was often conserved in the consensus sequence from the template, ARVA. Expanding this to include another RL in series may increase activity and/or reduce RBC interactions. | ↑Broth vs.<br>E. coli (−RBC)*<br>↑Broth vs.<br>P. aeruginosa (+RBC)*<br>↑Radial Diffusion vs.<br>S. aureus*<br>↓Hemolysis* |

TABLE 4-continued

| Peptide | Sequence | Hypothesis | Significant Results |
|---|---|---|---|
| RAT6 | (Library Consensus)<br>RRGWARRLAFAFGRR<br>↓<br>RRGWARRLAFAF::GRR | Alternating AF residues appear twice in the consensus sequence. Expanding this to include another AF in series may increase activity. | ↑Broth vs.<br>*E. coli* (-RBC)**<br>↑Broth vs.<br>*P. aeruginosa* (+RBC)**<br>↑Radial Diffusion vs.<br>*E. coli***<br>↓Hemolysis* |
| RAT7 | (Library Consensus)<br>RRGWARRLAF::GRR<br>↓<br>RRGWARRLAFGRR | Alternating AF residues appear twice in the consensus sequence. Contract this to remove an AF in series may reduce RBC interactions. | ↓Broth vs.<br>*E. coli* (-RBC)***<br>↓Broth vs.<br>*P. aeruginosa* (-RBC)***<br>↓Broth vs.<br>*P. aeruginosa* (+RBC)***<br>↓Radial Diffusion vs.<br>*E. coli**<br>↑Hemolysis |

TABLE 5

| Peptide | Sequence | Hypothesis | Significant Results |
|---|---|---|---|
| D-GNS2 | (GNS2)<br>RRGWAFRRALAYGRR<br>↓<br>rrgwafrralaygrr | In the first round of rational design, changing the consensus sequence from the L-form to the D-form led to a huge improvement in antimicrobial activity and activity retention in the presence of RBCs. Because the sequences are similar, it is possible that some of the library isolates may see performance increases when they are synthesized as D-peptides. | ↑Broth vs.<br>*E. coli* (-RBC)***<br>↑Broth vs.<br>*E. coli* (+RBC)***<br>↑Radial diffusion vs.<br>*E. coli****<br>↑Radial diffusion vs.<br>*S. aureus**<br>↓Hemolysis |
| D-DBS1 | (DBS1)<br>RRGWARRLFFAYGRR<br>↓<br>rrgwarrlffaygrr | | ↑Broth vs.<br>*E. coli* (-RBC)***<br>↑Broth vs.<br>*E. coli* (+RBC)***<br>↑Broth vs.<br>*S. aureus* (-RBC)***<br>↑Broth vs.<br>*S. aureus* (+RBC)***<br>↑Broth vs.<br>*P. aeruginosa* (-RBC)***<br>↑Broth vs.<br>*P. aeruginosa* (+RBC)***<br>↑Radial diffusion vs.<br>*E. coli****<br>↑Radial diffusion vs.<br>*S. aureus***<br>↓Hemolysis* |
| D-KON | (Consensus sequence)<br>::GWA::LAFAFG::<br>↓<br>::GWA::LAFAFG:: | The nature of the sidechain is important in addition to just the presence of a positive charge. By changing arginine to lysine, we should be able to learn something about the importance of using one residue vs. the other in antimicrobial peptide design. Additionally, lysine is modestly more soluble in aqueous buffers than arginine. It will also be interesting to see if the effect of the discretely positively charged primary amine of lysine will have an effect on potency as compared to the distributed charge of the guanidinium group on arginine. | ↓Broth vs.<br>*E. coli* (-RBC)***<br>↓Broth vs.<br>*E. coli* (+RBC)***<br>↓Broth vs.<br>*P. aeruginosa* (-RBC)***<br>↓Broth vs.<br>*P. aeruginosa* (+RBC)***<br>↓Radial diffusion vs.<br>*E. coli****<br>↓Radial diffusion vs.<br>*S. aureus**** |
| D-NOGCON | (Consensus sequence)<br>RR::WARRLAFAF::RR<br>↓<br>RRWARRLAFAFRR | In antimicrobial peptide canon, activity is driven by electro-static and hydrophobic interactions, to which glycine does not contribute. Still, conglomerate data on AMPs shows that glycine is statistically overrepresented, making its role somewhat ambiguous. In the | ↑Broth vs.<br>*E. coli* (-RBC)***<br>↑Broth vs.<br>*E. coli* (+RBC)***<br>↑Broth vs.<br>*S. aureus* (-RBC)***<br>↑Broth vs.<br>*S. aureus* (+RBC)*** |

TABLE 5-continued

| Peptide | Sequence | Hypothesis | Significant Results |
|---|---|---|---|
| | | preliminary round of rational engineering, we tried removal on DBS1 and NATT. Neither peptide suffered any activity change against *P. aeruginosa* or *E. coli*, and both gained a modest amount of activity against *S. aureus*. The modification did not have a noticeable effect with respect to antimicrobial activity in the presence of RBCs. | ↑Broth vs. *P. aeruginosa* (−RBC)*** ↑Broth vs. *P. aeruginosa* (+RBC)*** ↑Radial diffusion vs. *E. coli**** ↑Radial diffusion vs. *S. aureus*** |

Example 20. Treating an Infection Using an AMP

A subject having an infection by a pathogen (e.g., *Acinetobacter* spp. (*Acinetobacterbaumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *B. cepacia*, *Citrobacter freundii*, *Citrobacter koseri*, *Clostridium clostridioforme*, *Clostridium perfringens*, *C. sordeffii*, *Enterobacter aerogenes*, *Enterobacter cloacae*, *Enterococcus faecalis*, *Enterococcus* spp. (vancomycin susceptible and resistant isolates), *Escherichia coli* (including ESBL and KPC producing isolates), *Eubacterium lentum*, *Fusobacterium* spp., *Haemophilus influenzae* (including beta-lactamase positive isolates), *Haemophilus parainfluenzae*, *Klebsiella pneumoniae* (including ESBL and KPC producing isolates), *Klebsiella oxytoca* (including ESBL and KPC producing isolates), *Legionella* pneumophilia, *Moraxella catarrhalis*, *Morganella morganii*, *Mycoplasma* spp., *Peptostreptococcus* spp., *Porphyromonas saccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus* (methicillin susceptible and resistant isolates), *Staphylococcus epidermidis* (methicillin susceptible and resistant isolates), *Stenotrophomonas maltophilia*, *Streptococcus agalactiae*, *Streptococcus constellatus*, *Streptococcus pneumoniae* (penicillin susceptible and resistant isolates), *Streptococcus pyogenes*, or *Streptococcus pyogenes*) can be treated using an AMP (e.g., an AMP of any one of SEQ ID NOS: 19-42). If the infection were in a wound, the AMP could be administered in a proper formulation (e.g., dissolved in a buffer, or incorporated into a cream). Following administration the AMPs target and lyse the microbial cells, thereby inhibiting growth and treating the infection. Following administration of the AMP, a practitioner skilled in the art can monitor the subject's improvement in response to the AMP therapy by a variety of methods.

Example 21. Preventing an Infection in an Immunocompromised Subject

An immunocompromised subject (e.g., a subject having cancer, undergoing chemotherapy) can, after surgery, be treated with an antimicrobial peptide described herein (e.g., SEQ ID NOS: 19-42) to treatt infection and/or inhibit the growth of the pathogen (e.g., *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *B. cepacia*, *Citrobacter freundii*, *Citrobacter koseri*, *Clostridium clostridioforme*, *Clostridium perfringens*, *C. sordellii*, *Enterobacter aerogenes*, *Enterobacter cloacae*, *Enterococcus faecalis*, *Enterococcus* spp. (vancomycin susceptible and resistant isolates), *Escherichia coli* (including ESBL and KPC producing isolates), *Eubacterium lentum*, *Fusobacterium* spp., *Haemophilus influenzae* (including beta-lactamase positive isolates), *Haemophilus parainfluenzae*, *Klebsiella pneumoniae* (including ESBL and KPC producing isolates), *Klebsiella oxytoca* (including ESBL and KPC producing isolates), *Legionella pneumophilia*, *Moraxella catarrhalis*, *Morganella morganii*, *Mycoplasma* spp., *Peptostreptococcus* spp., *Porphyromonas saccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus* (methicillin susceptible and resistant isolates), *Staphylococcus epidermidis* (methicillin susceptible and resistant isolates), *Stenotrophomonas maltophilia*, *Streptococcus agalactiae*, *Streptococcus constellatus*, *Streptococcus pneumoniae* (penicillin susceptible and resistant isolates), *Streptococcus pyogenes*, or *Streptococcus pyogenes*) including drug resistant forms (e.g., methicillin resistant *S. aureus* and vancomycin resistant *Enterococcus*), thereby treating and/or protecting the subject from the infection.

Example 22. Sterilizing a Surface Using an AMP

A surface (e.g., an operating table or tool bench) can be sterilized to remove pathogens (e.g., methicillin resistant *S. aureus*) by the application of a suitable composition containing an AMP described herein (SEQ ID NOS: 19-37) for a suitable duration. Multi-drug resistant pathogens are becoming increasingly common in the hospital environment, and are a growing problem. AMPs, with their low propensity for eliciting antibiotic resistant bacterial phenotypes can be used to sterilize hospital surfaces of microbial pathogens (e.g., bacteria or fungus) including multi-drug resistant pathogens (FIG. 32) (e.g., methicillin resistant *S. aureus*).

Example 23. D-NOGCON can Inhibit Biofilm Formation by *P. aeruginosa*

Figure 33A:
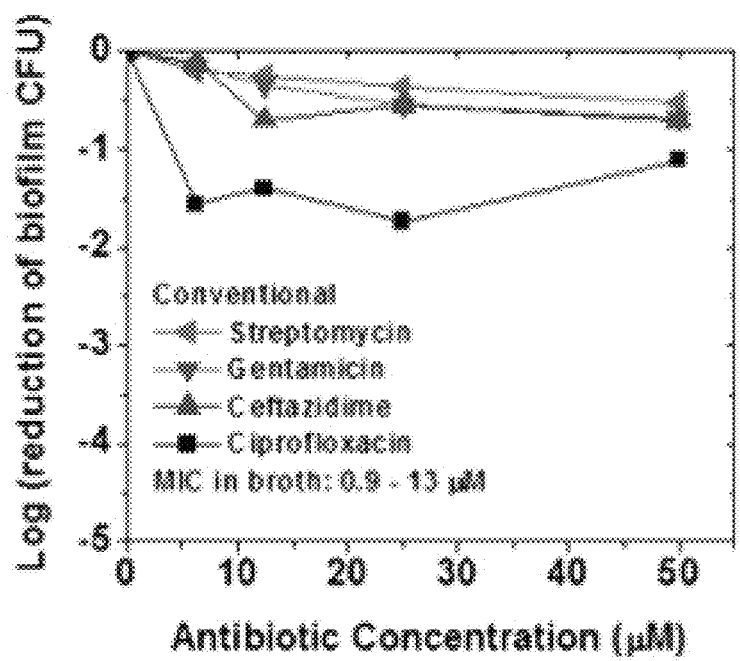
FIGS. 33A and 33B are plots showing the activity of parent and rationally designed antimicrobial peptides against *P. aeruginosa* biofilms.
Figure 33B:
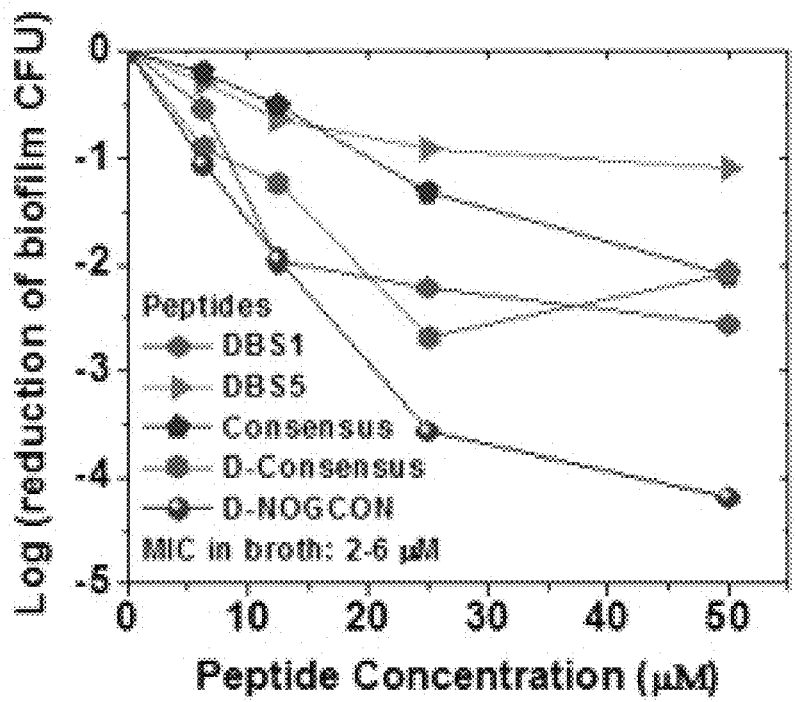
Figure 34A:
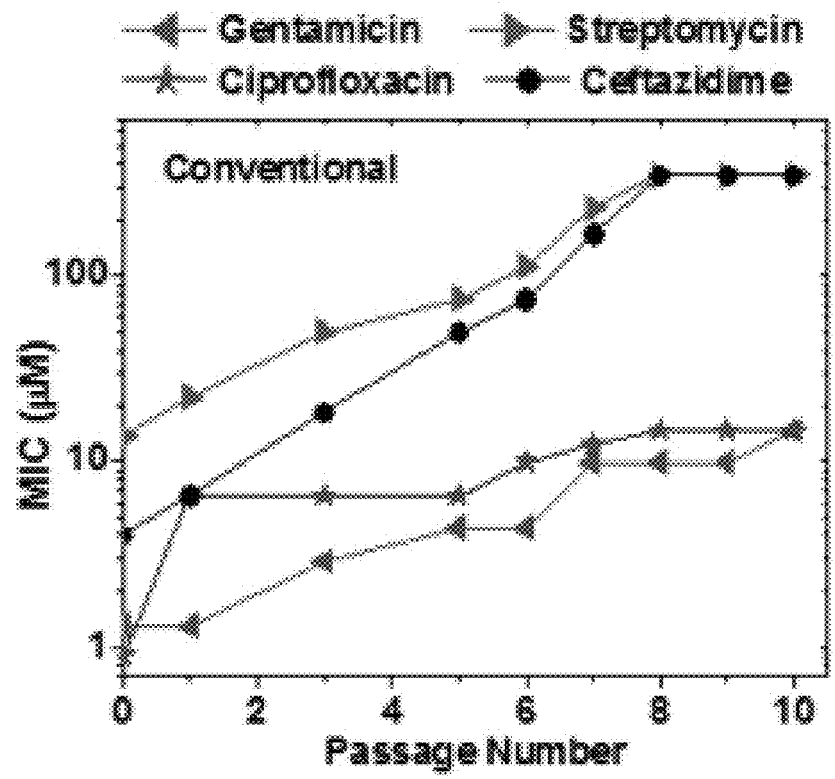
FIGS. 34A and 34B are plots showing the results of parent and rationally designed antimicrobial peptides testing induced resistance in *P. aeruginosa*.
Figure 34B:
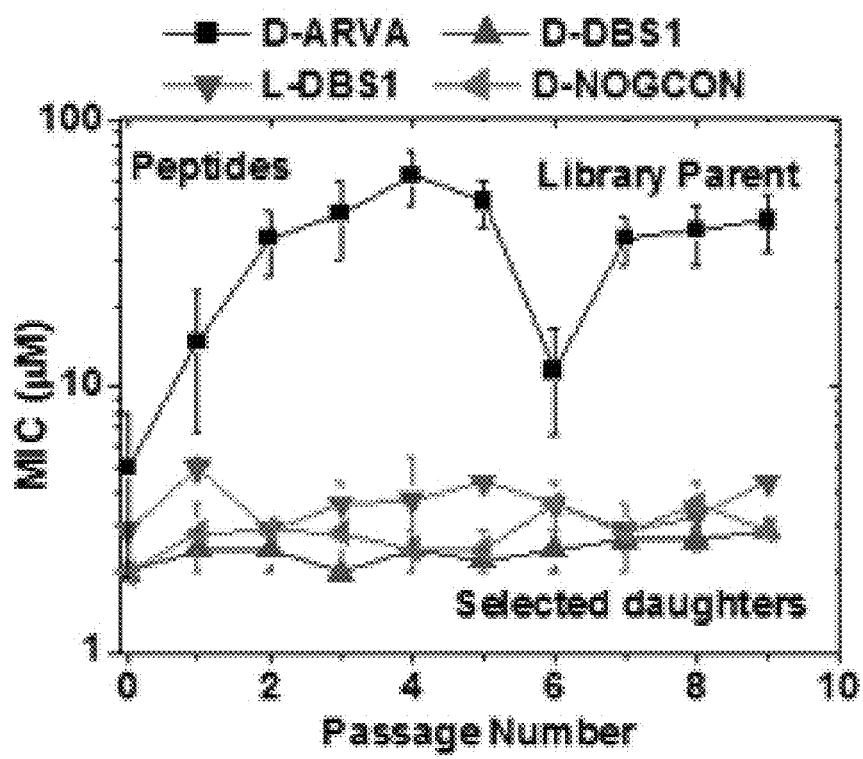
Figure 35A:
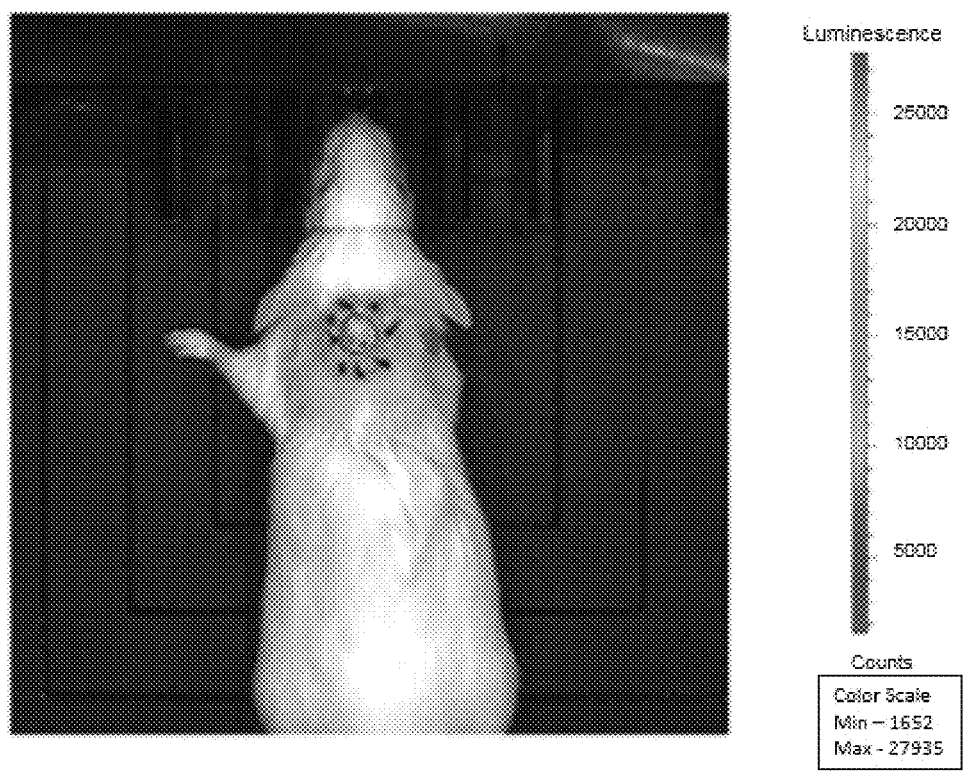
FIGS. 35A-35D are whole animal images of mice with deep wounds infected with a luminescent strain of *P. aeruginosa* prior to treatment.
Figure 35B:
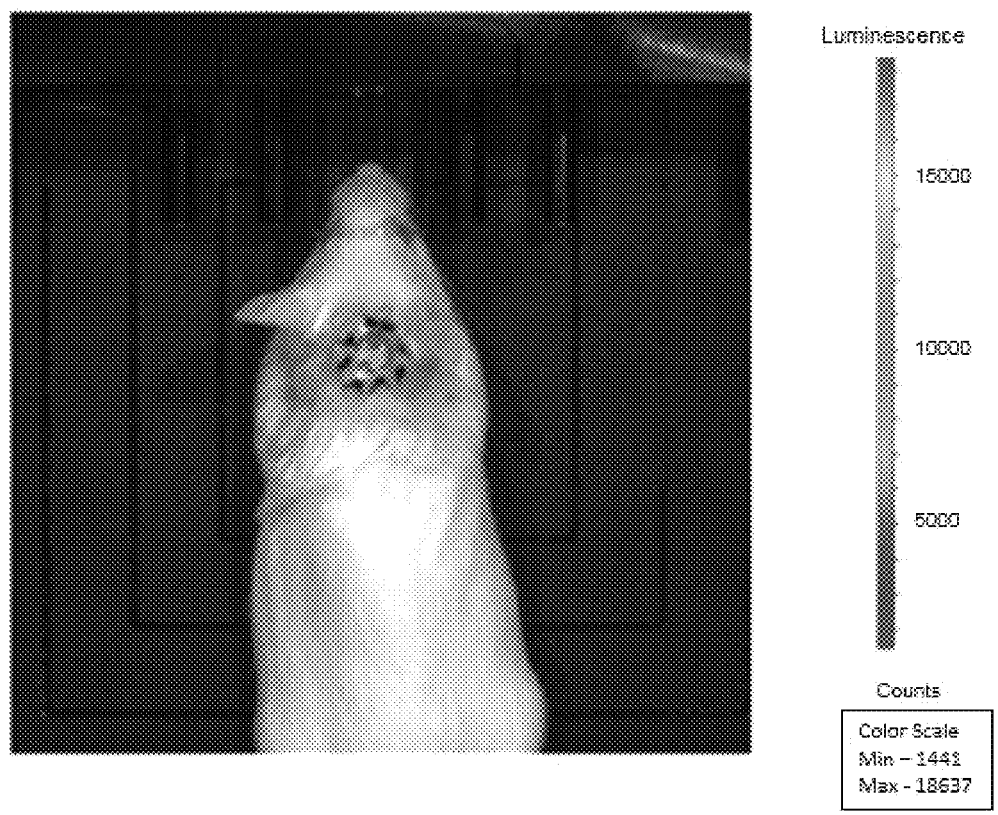
Figure 35C:
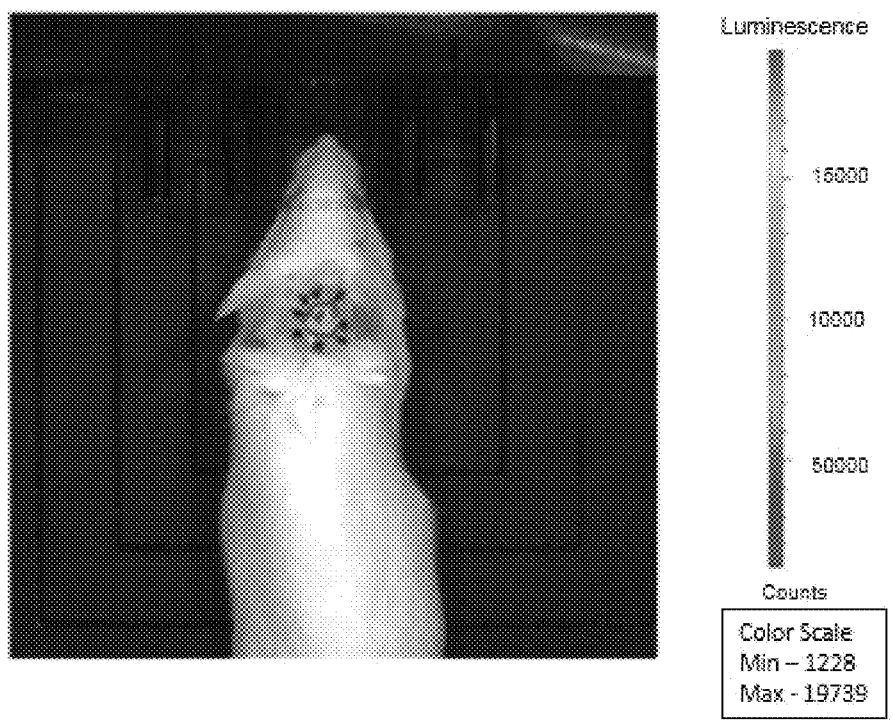
Figure 35D:
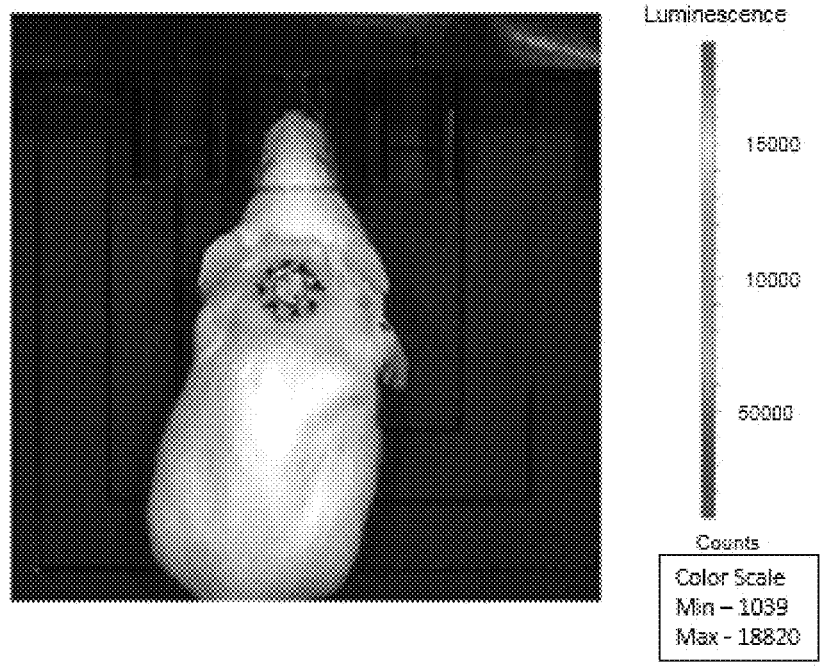
Figure 36A:
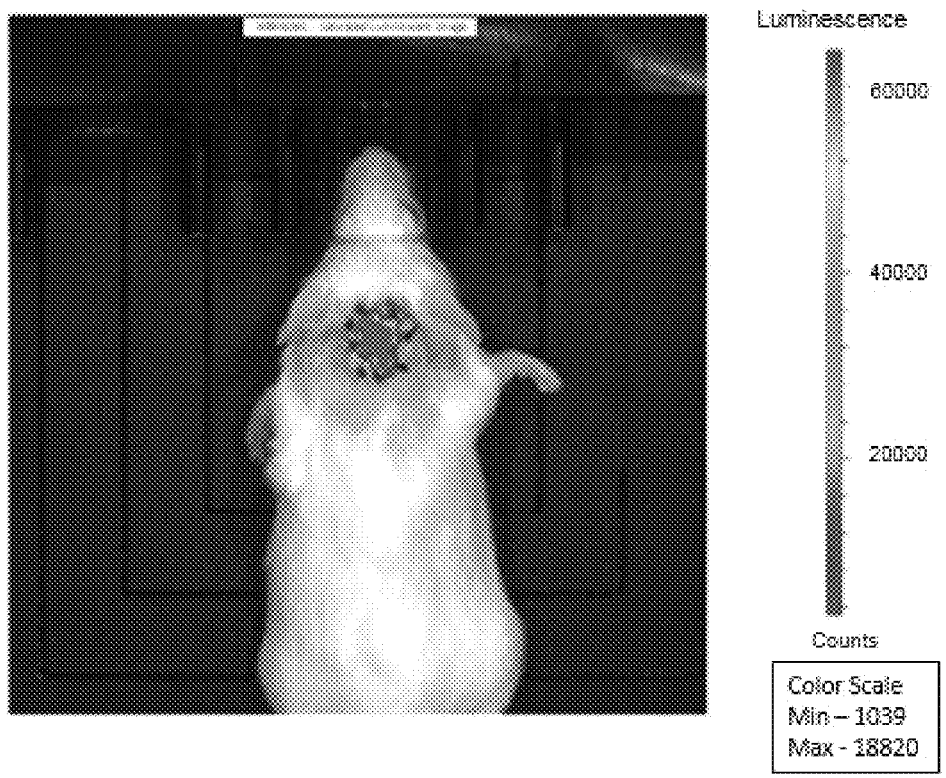
FIGS. 36A-36D are whole animal images of mice with deep wounds infected with a luminescent strain of *P. aeruginosa* on day one of treatment.
Figure 36B:
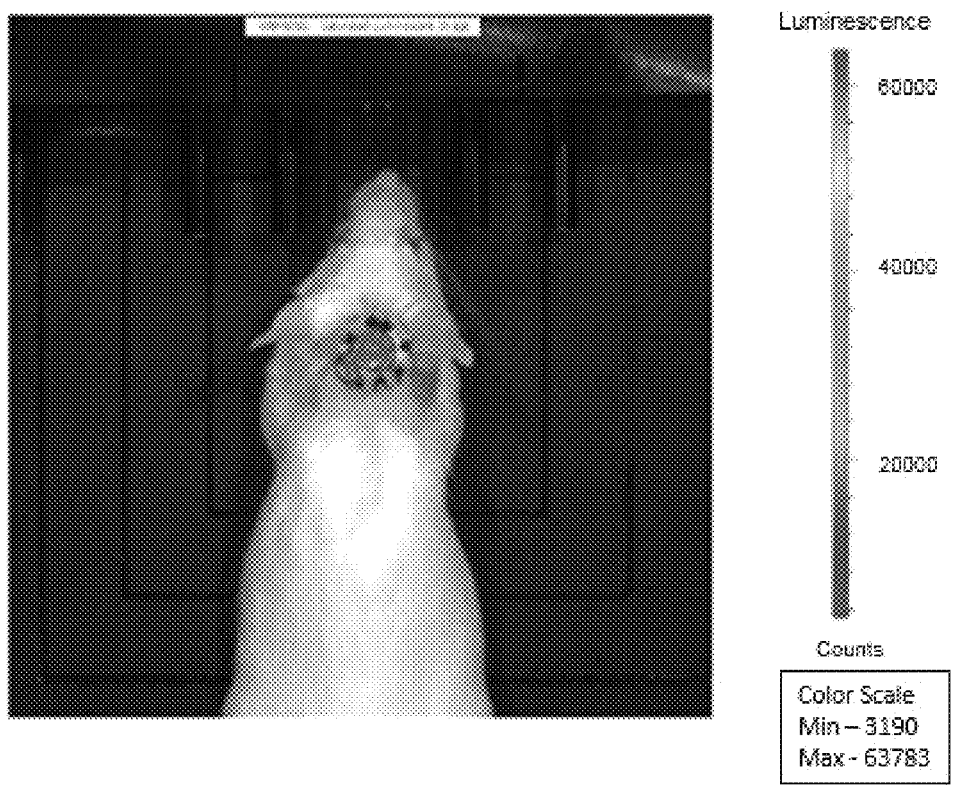
Figure 36C:
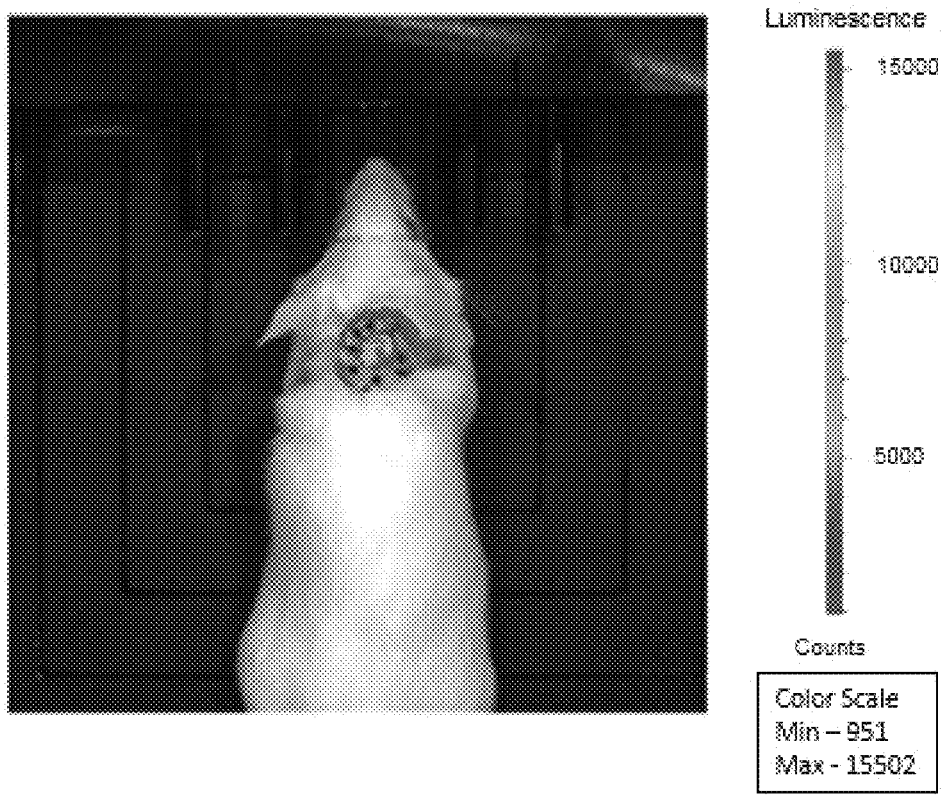
Figure 36D:
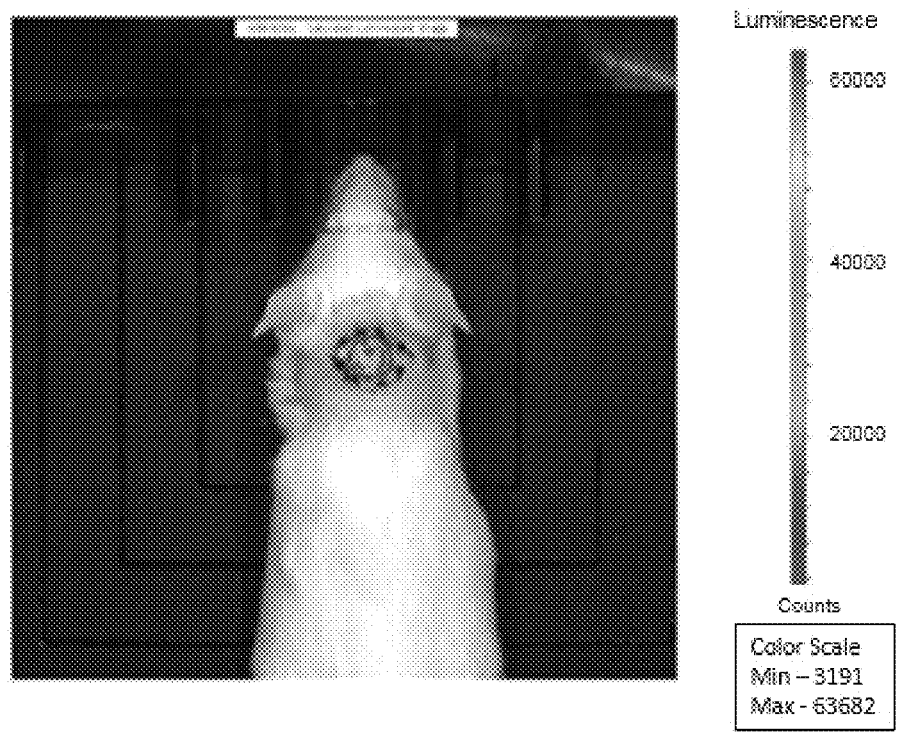

Bacterial biofilm formation on implanted medical devices is a serious medical problem because these biofilms can lead to life-threatening systemic infections. We tested selected peptides and rationally designed variants against biofilms formed by *P. aeruginosa*. The results (FIG. 33) show that these biofilms are highly resistant to multiple conventional antibiotics and most peptides. However, they are susceptible to several of the AMPs described herein, in particular, the peptide D-NOGCON (SEQ ID NO: 37) which exhibits antibiofilm activity. D-NOGCON reduces viable bacteria by 3.6 logs (1/3000 reduction) at 25 µM, while the best conventional antibiotic, Ciprofloxacin, reduced viable bacteria by only 1.7 logs (⅕₅ reduction) at 25 µM.

Example 24. AMPs Show No Induction of Resistance

Bacterial resistance against peptide antibiotics is known to occur, although it is reportedly more difficult to induce than resistance against conventional antibiotics. *P. aeruginosa* can gain resistance to some AMPs through selection for a variant with altered outer membrane composition. We used *P. aeruginosa* in a screen (FIG. 36) to select against rapid resistance. We tested if *P. aeruginosa* can stably gain resistance to the rationally designed peptides described herein and we compared their ability to adapt to conventional antibiotics under the same conditions. For ten serial passages, we performed broth sterilization assays using ⅔ serially diluted antibiotics with overnight growth. For each passage, we used the bacteria that grew at the highest antibiotic concentration to expand overnight for the subsequent generation. ARVA, the peptide template for the second generation library, promoted total resistance in a few passages in both L- and D-amino acid forms. All of the conventional antibiotics promoted increasing resistance, and two promoted complete resistance by 10 passages. The peptides selected in the screen in Example 16 (SEQ ID NOS: do not induce any measurable resistance in ten passages, suggesting that they would have significant advantages over conventional antibiotics in the clinic.

Example 25. Rationally Designed Peptides are Active Against MDR Clinical Isolates In FIG. 32 we show the MIC values for the selected AMPs (SEQ ID NOS: 22-26) against clinical isolates of multidrug resistant *A. baumannii*, and *K. pneumoniae* to determine the AMP with the highest activity. The former strain is resistant to almost all known antibiotics, and is a serious, growing concern. The peptides selected in this test are highly active at low µM sterilizing activity against both multi-drug resistant bacterial strains. It is interesting to note that the multi drug resistant strain of *K. pneumoniae* is even more susceptible to these peptide antibiotics than the normal, drug-susceptible strain. These results show the efficacy of AMPs against particularly worrisome multi-drug resistant bacterial isolates from hostpitals.

Figure 37A:
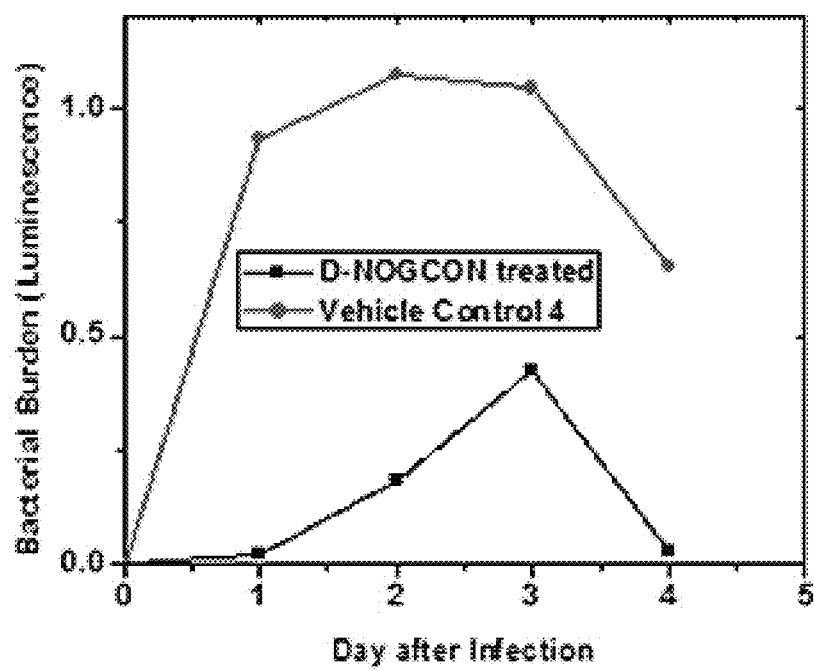
FIGS. 37A and 37B are graphs showing the protection from infection in a living animal by D-NOGCON.
Figure 37B:
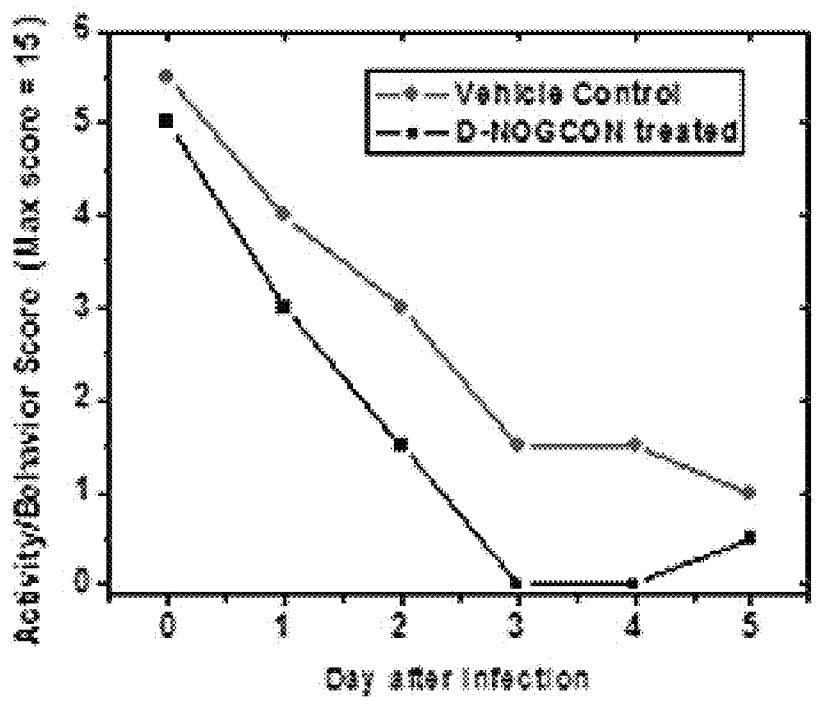

Example 26. Rationally Designed D-NOGCON can Treat Wound Microbial Infection Deep wounds in mice were infected with a luminescent strain of *P. aeruginosa* and monitored with whole animal imaging (FIGS. 35-37). In FIG. 36 infections are just beginning to become established. Areas of red indicate maximal bacterial colonization. No treatments have occurred. Treatment was twice per day, with 50 µg of D-NOGCON peptide in 20 µL of vehicle (0.025% acetic acid) starting 2 hours after infection. After a single day of treatment the infection is dramatically reduced compared to the control (FIG. 36). In the control animals (FIG. 36A), the infection is fully established across the entire wound bed and saturated the detector (red color). In the treated animals (FIG. 36B) the infection is much smaller in area and much lower in intensity, indicating it is under control. Animals were treated on days 0, 1, and 2, and over the first 5 days of treatment integrated luminescence (FIG. 37A) showed significant protection, slowing of bacterial growth and more rapid clearance over control. The treated mice also showed better summed behavioral scores (FIG. 37B) (behavioral scores scale is 0 (normal) to 3 (maximally abnormal) each for activity/nesting, movement, grip strength, coat condition, and posture. Maximum score (worst condition)=15). These preliminary data suggest that mice treated with the AMP, exhibit more normal behavior, suggesting a therapeutic improvement in the treated mice.

Example 27. Treatment of Acute Pneumonia Induced by *P. aeruginosa* Aspiration with D-NOGCON Female C57BL/6 mice, aged five weeks, were obtained from Charles River Laboratories. Upon receipt, they were allowed at least one week to recover from transport and acclimate to the new housing environment. Mice were maintained on a standard chow diet. Experiments were performed with mice no younger than six weeks and no older than nine weeks. *P. aeruginosa* PA01 was cultured overnight in tryptic soy broth (TSB) at 37° C. and shaken at 220 RPM. Prior to infecting the mice, the overnight culture was diluted 100-fold into 25-mL of fresh TSB. The culture was grown for three hours before optical density was determined. Previous growth curve experiments allowed us to dilute this newly expanded culture to $1.4 \times 10^8$ CFU/mL. To infect an animal, mice were anesthetized using isoflurane and 50 µL of bacterial suspension ($7 \times 10^6$ CFUs) was administered via intratracheal instillation. Briefly, the anesthetized mice were suspended from wire by their front feet and blunt forceps were used to extract the tongue. The tongue was pulled out and downward. The bacterial suspension was deposited in the back of the throat with a micropipette. The nares of the animal were then covered while the mouse recovered from anesthesia. The chest was gently rubbed to promote inhalation. The mice were made to inhale 15 times before the tongue was released and the mouse was removed from the wire. The animals were then allowed a minute to fully awaken and then returned to their cages.

Figure 28A:
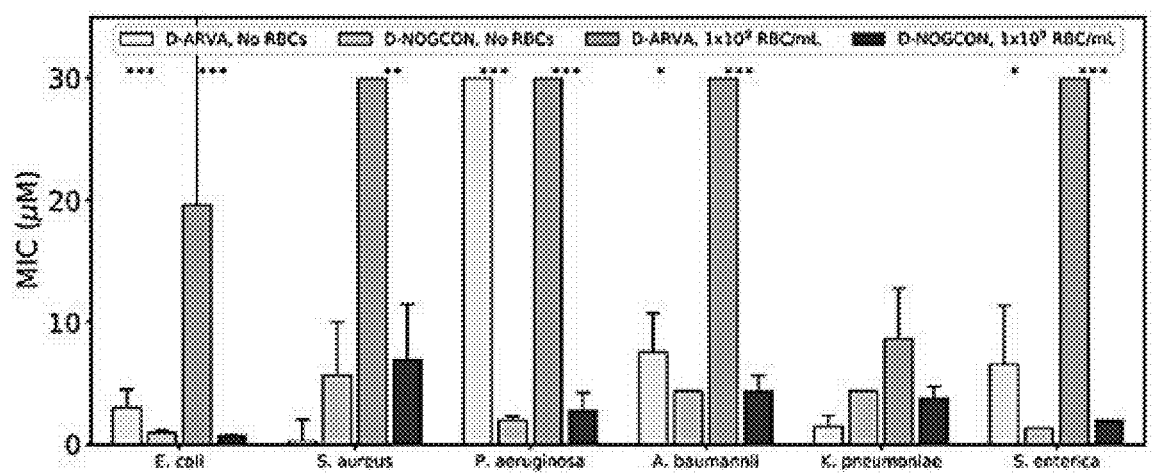
FIGS. 28A-28E are plots showing the results from a comparison of D-NOGCON with the parent sequence, D-ARVA.
Figure 28B:
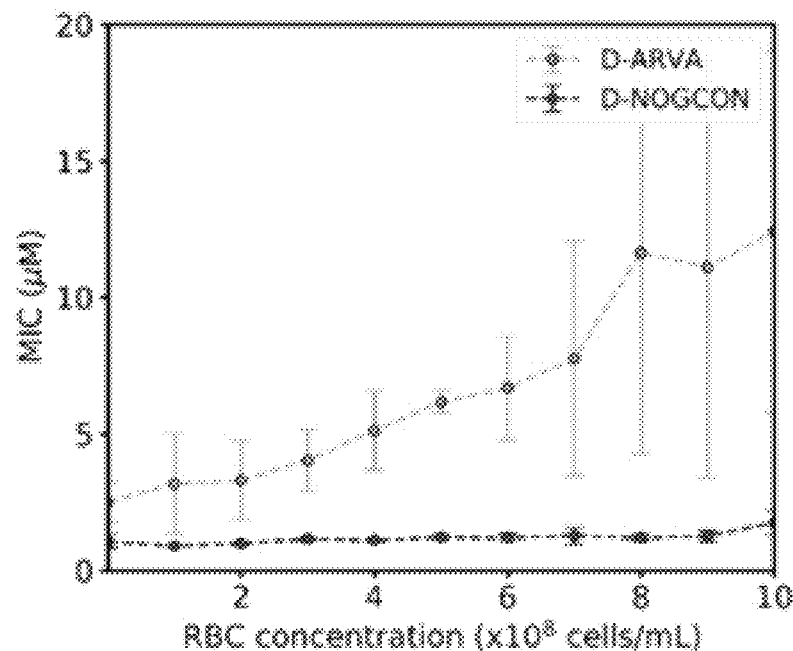
Figure 28C:
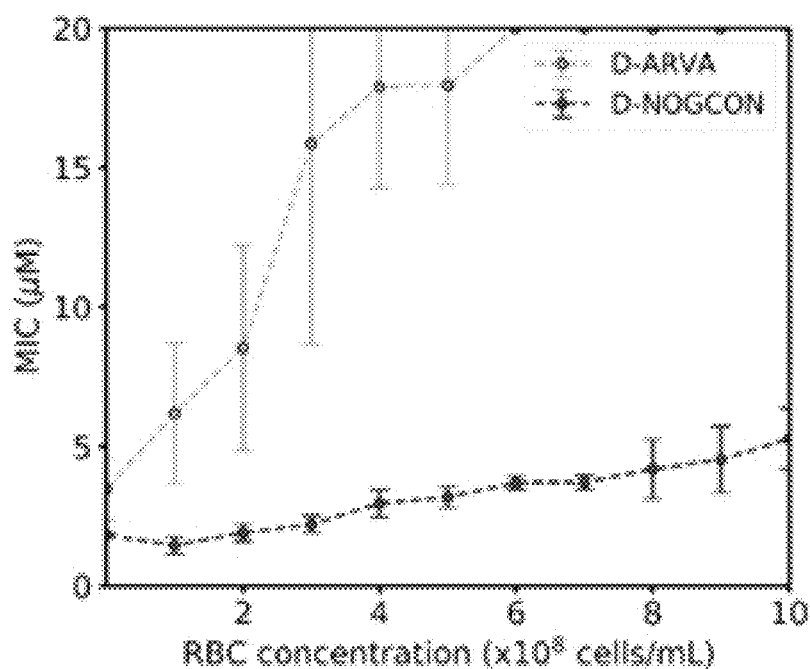
Figure 28D:
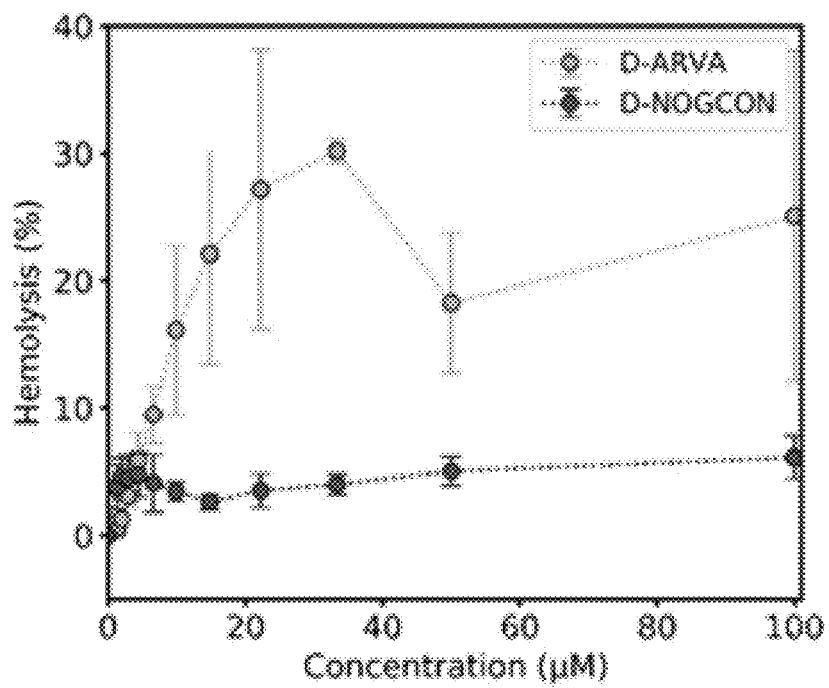
Figure 28E:
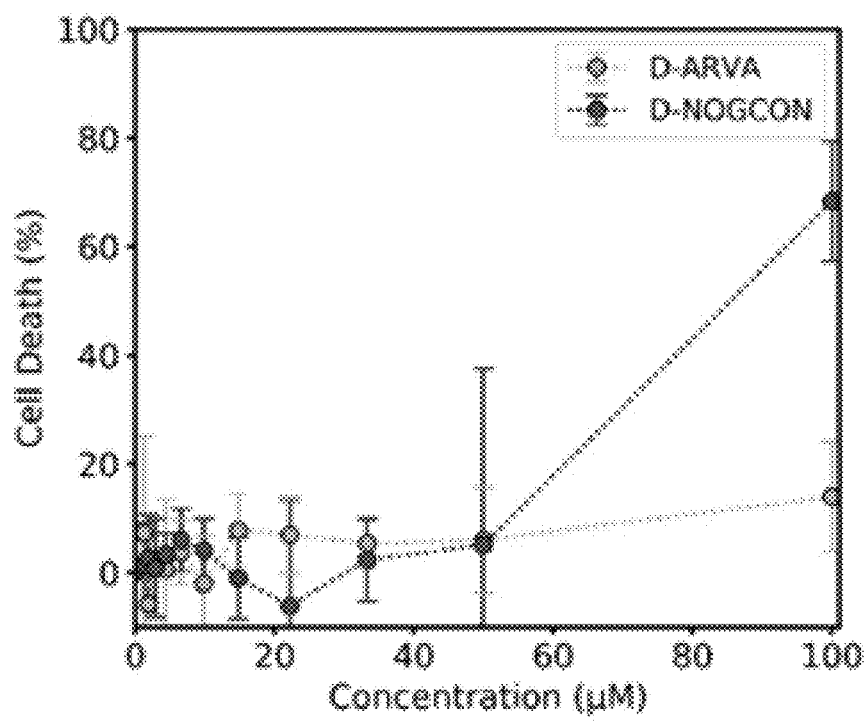

The mice were then treated with D-NOGCON (SEQ ID NO:37), which were instilled in the trachea, exactly as described above for the administration of bacterial infection. Before attempting to treat a *P. aeruginosa* infection of the lung, we sought to establish a safe dose for administration of the D-NOGCON peptide via aspiration. Based on in vitro toxicity data (FIGS. 28D and 28E), a dosing regimen of 50 µL of D-NOGCON (100 µM) was administered every 8 hours for 3 days (9 doses). As a no treatment control, we administered 50 µL of PBS on the same schedule.

Figure 29A:
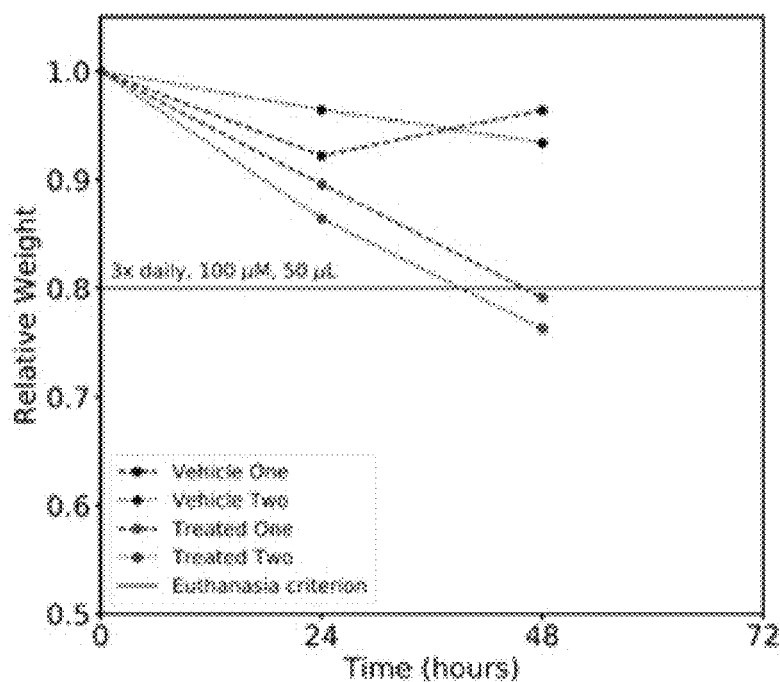
FIGS. 29A-29B are plots showing the results of a safety study for aspirated D-NOGCON by C57BL/6 mice.
Figure 29B:
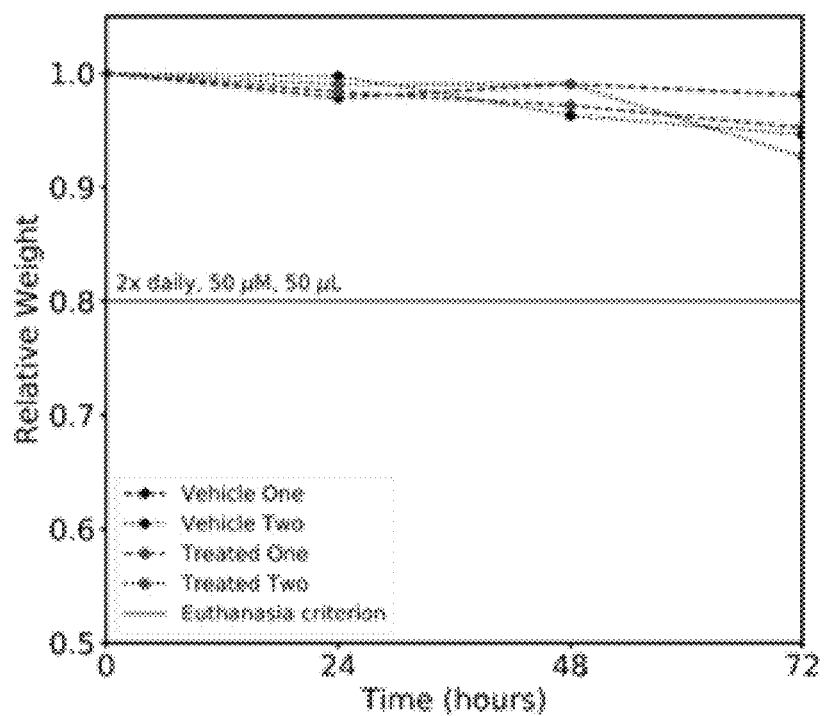

To monitor the toxicity we measured animal behavior and body weight changes (FIG. 29A). Because the initial dosing regimen proved too toxic for the animals to tolerate, we reduced both the peptide concentration and the frequency of administration. In the second safety trial, we administered 50 µL of D-NOGCON (50 µM) twice daily, for three days and monitored the animals behavior and body weight changes (FIG. 29B). We determined that this dosing regimen was sufficiently safe to proceed with bacterial challenge experiments.

Figure 30A:
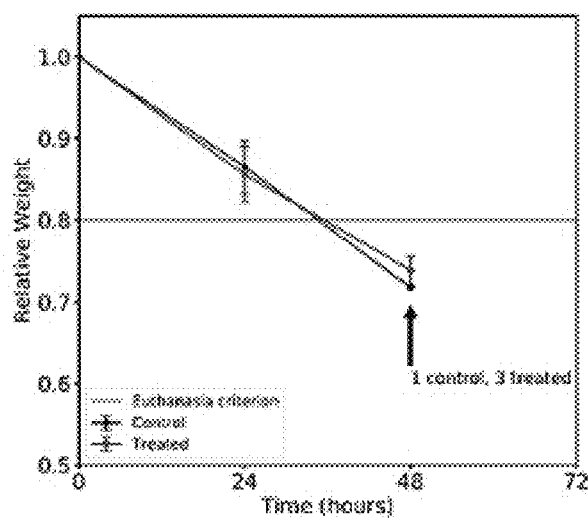
FIGS. 30A-30C are plots showing the results of the treatment of acute pneumonia induced by *P. aeruginosa* by D-NOGCON.
Figure 30B:
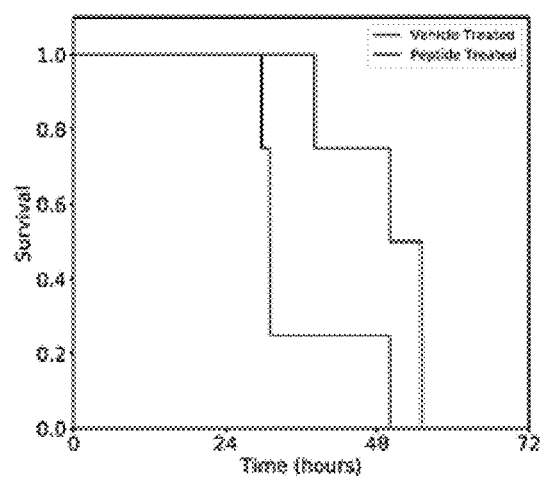
Figure 30C:
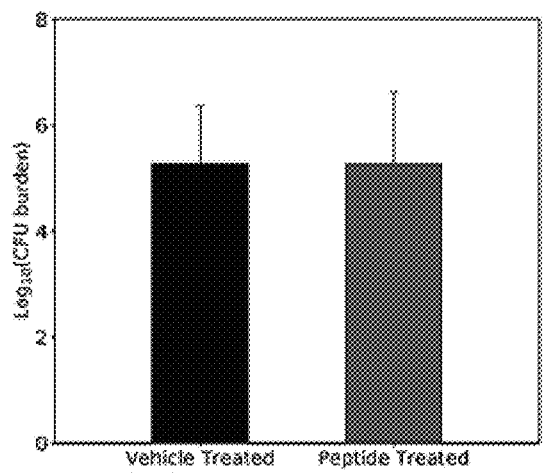

Our initial experiment was survival-based. We infected 8 mice (4 for treatment, 4 for vehicle) with the above bacterial load in 50 µL of PBS and allowed 2 hours of recovery prior to the initial treatment administration. After the recovery period, dosing proceeded as it had for the second safety study (50 µL, 50 µM, 2× daily). All mice from both treatment groups survived the initial 24 hours. They appeared sluggish after infection and dosing, but did not show other outward signs of stress. At the 24-hour time point, mice from both groups lost ~12% body weight (FIG. 30A). Between 24 and 48-hour timepoints, 3 controls and 1 treated animal were sacrificed (FIG. 30B). The mice displayed outward signs of severe systemic infection. Most significantly, they lost the ability to maintain their balance and displayed excessive "rolling" behavior. Euthanasia is required in these cases because the animals are clearly suffering and are not able to obtain the nutrients required for survival. On day 3, the weight measurements indicated that all of the animals had lost more than 20% of their body weight (FIG. 30A). The lungs of 3 animals from each treatment group were removed, homogenized, and plated on PIA plates to determine the *P. aeruginosa* CFU burden (FIG. 30C).

Figure 31A:
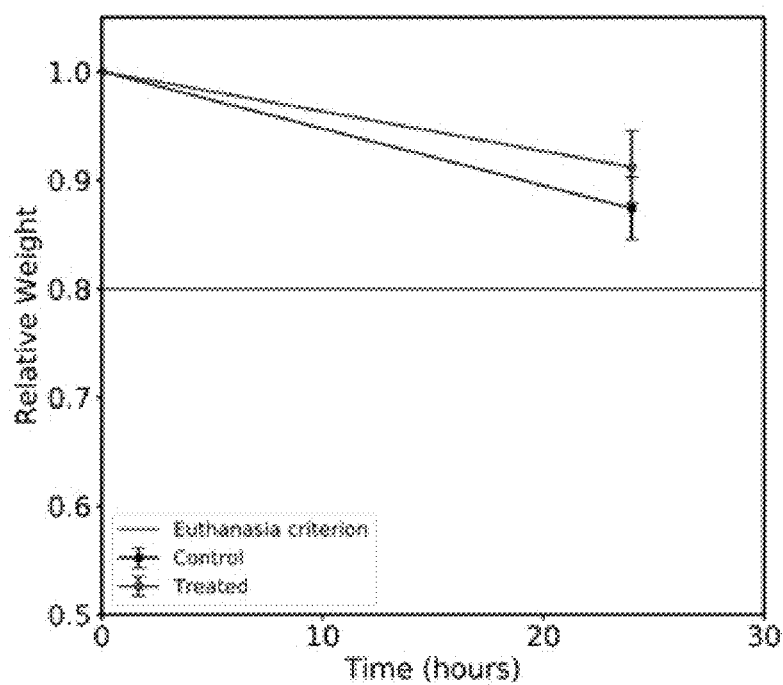
FIGS. 31A-31B are plots showing the CFU burden analysis for mice receiving two doses of D-NOGCON over 24 hours.
Figure 31B:
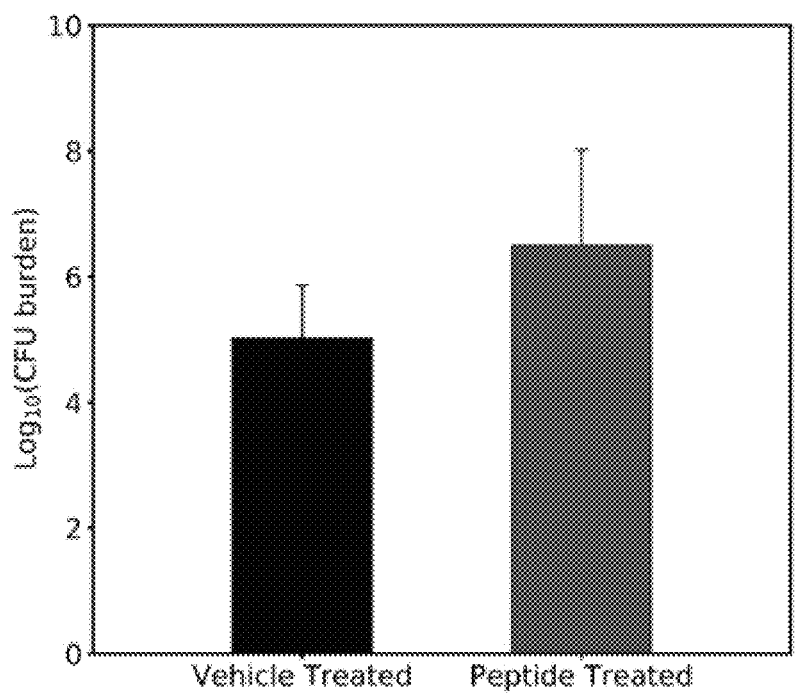

A third study reduced the CFU burden of *P. aeruginosa* to $7 \times 10^6$ and mice were treated as with the previous experiment. As in the previous experiment, both treated and untreated animals lost 10-12% of their body weight after 24 hours (FIG. 31A). Unexpectedly, we observed a non-significant increase in CFU burden in the treated animals (FIG. 31B). What was not taken into consideration in this experiment was the propensity for infection to spread to other tissues.

These studies showed the mice were able to tolerate the AMPs at an oral dose of 50 µL twice daily for 3 days with little to no side effects. The survival trial, with a CFU burden inflicting 100% mortality within three days of infection, showed little improvement in the infection titer after treatement with an oral dose of D-NOGCON (50 µL, 50 µM, 2× daily) led to the third study with a lower CFU burden. Although the infection titer of this third experiment showed little improvement in the D-NOGCON treated mice over control, the experiment was not optimized to test the activity of D-NOGCON on a systemic infection via an oral dose. Studies are ongoing with experiments designed to further test the AMPs in mouse models.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. All publications, patents, and patent applications mentioned in the above specification are hereby incorporated by reference to the same extent as if each individual publication, patent or patent application was specifically and individually indicated to be incorporated by reference in its entirety.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Other embodiments are within the claims.

The invention claimed is:

1. A polypeptide, wherein the polypeptide:
   a) has at least 85% sequence identity to the sequence of any one of SEQ ID NOS: 3-10; or
   b) has at least 85% sequence identity to the sequence of any one of SEQ ID NOS: 19-42.

2. The polypeptide of claim 1, wherein the polypeptide of a):
   a) has at least 90%, 95%, 97%, or 100% sequence identity to any one of SEQ ID NOS: 3-10;
   b) exhibits a rate of cellular internalization of at least 200% relative to a Tat peptide (SEQ ID NO: 1);
   c) is a cell penetrating polypeptide;
   d) comprises one or more D-amino acids, wherein, optionally, the one or more D-amino acids are independently selected from the group consisting of D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, and D-VAL;
   e) comprises one or more derivatized amino acids, wherein, optionally, the one or more derivatized amino acids are selected from the group consisting of N-imbenzylhistidine, 4-hydroxyproline, 5-hydroxylysine, 3-methylhistidine, homoserine, and ornithine or the derivatized amino acid has a chemical moiety selected from the group consisting of amine hydrochloride, p-toluene sulfonyl, carbobenzoxy, t-butyloxycarbonyl, chloroacetyl, formyl, carboxyl, methyl ester, ethyl ester, hydrazide, O-acyl, and O-alkyl; or
   f) is 10 to 16 amino acids long.

3. A conjugate comprising the polypeptide of a) of claim 1 joined to a compound, wherein, optionally:
   a) the polypeptide is joined directly, or through a linker, to the compound;
   b) the polypeptide is joined to the compound by a covalent bond;
   c) the compound enhances the stability, or immunogenicity, or detection of the polypeptide;
   d) the compound facilitates purification of the polypeptide;
   e) the compound is a second polypeptide;
   f) the compound is a therapeutic agent; or
   g) the compound is a nucleic acid molecule or a peptide nucleic acid molecule.

4. The conjugate of claim 3, wherein:
   a) the therapeutic agent is selected from the group consisting of an immunotherapy agent, a cytotoxic agent, a growth inhibitory agent, a radiation therapy agent, an anti-cancer agent, an anti-angiogenic agent; or
   b) the nucleic acid molecule comprises a phosphate backbone modification, wherein, optionally, the phosphate backbone modification is phosphorothioate or phosphorodithioate.

5. The conjugate of claim 4, wherein:
   a) the anti-cancer agent is selected from the group consisting of abiraterone acetate, methotrexate, paclitaxel, albumin, doxorubicin, bleomycin, vinblastine, dacarbazine, vincristine sulfate, etoposide phosphate, prednisone, cyclophosphamide, brentuximab vedotin, cytarabine, daunorubicin, ado-trastuzumab emtansine, afatinib dimaleate, everolimus, netupitant, palonosetron, imiquimod, alectinib, alemtuzumab, melphalan, pemetrexed, chlorambucil, aminolevulinic acid, aprepitant, pamidronate, anastrozole, exemestane, nelarabine, arsenic trioxide, ofatumumab, asparaginase *Erwinia chrysanthemi*, bevacizumab, axitinib, azacitidine, carmustine, belinostat, bendamustine, cisplatin, bexarotene, tositumomab, iodine$^{131}$I tositumomab, bicalutamide, blinatumomab, bortezomib, bosutinib, busulfan, cabazitaxel, cabozantinib-S-malate, irinotecan, capecitabine, fluorouracil, carboplatin, carfilzomib, lomustine, ceritinib, recombinant human papillomavirus (HPV) bivalent vaccine, cetuxima, clofarabine, cobimetinib, dactinomycin, crizotinib, ifosfamide, ramucirumab, liposome, dabrafenib, decitabine, daratumumab, dasatinib, degarelix, denileukin diftitox, denosumab, dexamethasone, dexrazoxane, dinutuximab, docetaxel, rasburicase, epirubicin, elotuzumab, eltrombopag olamine, enzalutamide, eribulin mesylate, vismodegib, erlotinib, etoposide, raloxifene, toremifene, panobinostat, fulvestrant, letrozole, filgrastim, fludarabine phosphate, flutamide, pralatrexate, recombinant HPV quadrivalent vaccine, recombinant HPV nonavalent vaccine, obinutuzumab, gefitinib, gemcitabine, gemcitabine-cisplatin, gemcitabine-oxaliplatin, gemtuzumab ozogamicin, imatinib mesylate, glucarpidase, goserelin acetate, trastuzumab, HPV bivalent vaccine, topotecan, palbociclib, ponatinib, idarubicin, idelalisib, ifosfamidum, interleukin-2 (IL-21, ibrutinib, talimogene laherparepvec, recombinant interferon alpha-2b, ipilimumab, romidepsin, ixabepilone, ixazomib citrate, ruxolitinib phosphate, palifermin, pembrolizumab, lanreotide acetate, lapatinib ditosylate, lenalidomide, lenvatinib mesylate, leucovorin calcium, leuprolide acetate, trifluridine, tipiracil, olaparib, procarbazine, mechlorethamine, megestrol acetate, trametinib, mercaptopurine, mesna, temozolomide, mitomycin C, mitoxantrone, plerixafor, vinorelbine tartrate, sorafenib tosylate, nivolumab, tamoxifen citrate, romiplostim, sonidegib, omacetaxine mepesuccinate, pegaspargase, ondansetron, osimertinib, oxaliplatin, paclitaxel albumin-stabilized nanoparticle, panitumumab, pazopanib, peginterferon alpha-2b, pertuzumab, pomalidomide, necitumumab, sipuleucel-T, $^{223}$Ra dichloride, recombinant human papillomavirus, regorafenib, rituximab, rolapitant, siltuximab, sunitinib malate, thalidomide, thioguanine, nilotinib, temsirolimus, thiotepa, trabectedin, arsenic trioxide, uridine triacetate, vandetanib, vorinostat, ziv-aflibercept, vemurafenib, ibritumomab tiuxetan, zoledronic acid, and idelalisib;
   b) the therapeutic agent is selected from a group consisting of Human growth hormone, Erythropoietin (EPO), Ob gene translation product (leptin), Adenosine deaminase, purine nucleoside, phosphorylase, cluster of differentiation-4 (CD-4), Factor VIII, Factor IX, α1-antitrypsin, low density lipoprotein (LDL) receptor protein, Intrinsic factor, albumin, b-glucosidase (glucocerebrosidase), cystic fibrosis (CF) transmembrane conductance regulator, tissue plasminogen activator (tPA), urokinase, streptokinase, antithrombin III, apolipoprotein, Low Density lipoprotein receptor, vascular endothelial growth factor (VEGF), Calcitonin, parathyroid hormone (PTH), PTH-like hormone, an adenosine deaminase, a Phenylalanine hydroxylase, a von Willebrand Factor, a Tumor Necrosis Factor (TNF), a cytokine, an anti-neoplastic agent, an interleukin (IL), an interferon (IFN), p53, anti-VEGF (bevacizumab), anti-Epidermal Growth Factor (EGF), oncogene anti-sense RNA, Rituximab, Daclizumab, Basiliximab, Palivizumab, Infliximab, Trastuzumab, Gemtuzumab ozogamicin, Alemtuzumab, Ibritumomab tiuxetan, Adalimumab, Omalizumab, Tositumomab-I-131, Efalizumab, Cetuximab, Bevacizumab, Natalizumab, Tocilizumab, Panitumumab, Ranibizumab, Eculizumab, Certolizumab pegol, Golimumab, Canakinumab, Ustekinumab, Ofatumumab, Denosumab, Motavizumab, Raxibacumab, Belimumab, Ipilimumab, Brentuximab Vedotin, Pertuzumab, Ado-trastuzumab emtansine, Obinutuzumab, a checkpoint inhibitor endothelin, Ciliary Neurotrophic Factor (CNTF), Brain Derived Neurite Factor (BDNF), nerve growth factor (NGF), tyrosine hydroxylase, a bone morphogenic protein (BMP), lactase, an epidermal growth factor, a transforming growth factor, a granulocyte-colony stimulating, a fibroblast growth, an insulin-like growth, an antithrombin, a hirudin, antidiuretic hormone (ADH), a selective serotonin reuptake inhibitor, an anti-psychotic bio-substance, an endorphin, an estrogen, an androgen, a mineralocorticoid, a glucocorticoid, an anabolic steroid, a thyroid hormone, a thyroglobulin, Dystrophin, an antimicrobial polypeptide, a lipid binding protein (LBP), L-asparaginase, pepsin, trypsin, chymotrypsin, cholecystokinin, sucrase, carboxypeptidase, catalase, uricase, elastase, thrombopoietin (TPO), porphobilinogen deaminase, glutaryl CoA dehydrogenase, cystathionine B-synthase, a copper transporting ATPase β-globin, α-globin, a Sonic hedgehog gene product, thyroid hormone, aflibercept, a soluble form of a VEGF receptor, platelet factor-4, prolactin, bevacizumab, ranibizumab, a TNFα inhibitor, an interleukin-6 (IL6) receptor inhibitor, an interleukin-1 (IL1) receptor inhibitor, abatacept, rituximab, mesalazine, prednisone, azathioprine, methotrexate, aldosterone, cortisol, alpha-L iduronidase, sphingomyelin phosphodiesterase1 (SMPD1), Niemann-Pick C1 (NPC1) protein, Niemann-Pick C2 (NPC2) protein, beta-hexosaminidase A, alpha galactosidase, galactosylceramidase, galactokinase, galactose-1-phosphate uridyltransferase, a branched-chain alpha-keto acid dehydrogenase complex enzyme, phenylalanine hydroxylase, glycogen synthase (GYS2), glucose-6-phosphatase (G6PC), acid alpha-glucosidase (GAA), glycogen debranching enzyme (AGL), glycogen branching enzyme (GBE1), muscle glycogen phosphorylase (myophosphorylase) (PYGM), liver glycogen phosphorylase (PYGL), muscle phosphoglycerate mutase (PGAM2), muscle phosphofructokinase (PKFM), glycogen phosphorylase kinase B, enolase 3 (ENO3), muscle lactate dehydrogenase (LDHA), glucose transporter 2 (GLUT2), aldolase A (ALDOA), β enolase (ENO3), Glycogenin-1 (GYG1), NADH dehydrogenase, thiamine-diphosphate kinase, thiamine triphosphate, pyruvate dehydrogenase, an adenosine triphosphate (ATP) synthase, thymidine phosphorylase (TYMP), reduced nicotinamide adenine dinucleotide (NADH) dehydrogenase, Frataxin (FXN), a protein encoded by peroxisomal biogenesis factor (PEX)-1 (PEX1), PEX2, PEX3, PEX5, PEX6, PEX10, PEX12, PEX13, PEX14, PEX16, PEX19, or PEX26, a protein encoded by ATP Binding Cassette Subfamily D Member 1 (ABCD1), Wilson disease protein (ATP7B), Human hemochromatosis protein (HFE), methylmalonyl CoA mutase, methylmalonyl CoA epimerase, adenosylcobalamin, propionyl-CoA carboxylase, ornithine transcarbamylase, argininosuccinate lyase, argininosuccinate synthase 1, citrin, carbamoyl phosphate synthase 1, N-acetylglutamate synthase, and ornithine translocase; or c) the phosphate backbone modification is an amide, thioamide, sulfinamide, or sulfonamide linkage.

6. A composition comprising the polypeptide of claim 1.

7. The composition of claim 6, further comprising a pharmaceutically acceptable carrier, excipient, or diluent.

8. The composition of claim 6, wherein the composition:
a) comprises the polypeptide of a) and further comprises a therapeutic agent, wherein, optionally, the therapeutic agent of the composition comprising the polypeptide of a) is an immunotherapy agent or an anti-cancer agent or the therapeutic agent of the composition comprising the polypeptide of b) is an antimicrobial agent or an antifungal agent; or
b) comprises the polypeptide of b) incorporated therein or coated therein, wherein, optionally, the composition is a medical device, a cuff, a dressing material, a mess, a hernia patch, a wound dressing, a bandage, a syringe, gloves, or a household product, a cosmetic product, a pharmaceutical product, a washing or cleaning formulation, a medical device surface, a medical device material, a fabric, a plastic, a surface of a plastic article, a paper, a nonwoven material, a wood, leather, or a metal surface.

9. A method comprising
delivering a compound to a target cell, the method comprising contacting the target cell with the conjugate of claim 3.

10. A method of penetrating a cellular membrane comprising contacting the cellular membrane with the composition of claim 6 or a conjugate thereof comprising the polypeptide joined to a compound.

11. A kit comprising:
a) a composition comprising the polypeptide of a) of claim 1 or a conjugate comprising the polypeptide of a) of claim 1 linked to a compound; or
b) a composition comprising the polypeptide of b) of claim 1 and, optionally, an antimicrobial agent.

12. The polypeptide of claim 1, wherein the polypeptide of b):
a) has at least 90%, 95%, 97%, or 100% sequence identity to any one of SEQ ID NOS: 19-42;
b) is an antimicrobial peptide;
c) disrupts the cellular membrane of a microbial pathogen;
d) comprises one or more D-amino acids, wherein, optionally, the one or more D-amino acids are independently selected from the group consisting of D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, and D-VAL;
e) comprises one or more derivatized amino acids, wherein, optionally the one or more derivatized amino acids are selected from the group consisting of N-imbenzylhistidine, 4-hydroxyproline, 5-hydroxylysine, 3-methylhistidine, homoserine, and ornithine or the derivatized amino acid has a chemical moiety selected from the group consisting of amine hydrochloride, p-toluene sulfonyl, carbobenzoxy, t-butyloxycarbonyl, chloracetyl, formyl, carboxyl, methyl ester, ethyl ester, hydrazide, O-acyl, and O-alkyl; or
f) is 10 and 20 amino acids long.

13. A method of treating a microbial infection comprising administering the polypeptide of b) of claim 1, or a composition thereof, to a subject in need thereof, wherein the polypeptide is an antimicrobial polypeptide.

14. The method of claim 13, wherein:
a) said subject is a human; or
b) said microbial infection is a fungal or bacterial infection, wherein, optionally:
   i) the bacterial infection is caused by a bacteria selected from a group consisting of *Acinetobacter baumannii, Bacteroides distasonis, Bacteroides fragilis, Bacteroides ovatus, Bacteroides thetaiotaomicron, Bacteroides uniformis, Bacteroides vulgatus, B. cepacia, Citrobacter freundii, Citrobacter koseri, Clostridium clostridioforme, Clostridium perfringens, C. sordellii, Enterobacter aerogenes, Enterobacter cloacae, Enterococcus faecalis, Enterococcus*, spp. *Escherichia coli, Eubacterium lentum, Fusobacterium* spp., *Haemophilus influenzae, Haemophilus parainfluenzae, Klebsiella pneumoniae, Klebsiella oxytoca, Legionella pneumophilia, Moraxella catarrhalis, Morganella morganii, Mycoplasma* spp., *Peptostreptococcus* spp., *Porphyromonas saccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus, Staphylococcus epidermidis, Stenotrophomonas maltophilia, Streptococcus agalactiae, Streptococcus constellatus, Streptococcus pneumoniae, Streptococcus pyogenes,* and *Streptococcus pyogenes*; or
   ii) the fungal infection is caused by a fungus selected from a group consisting of *Fusarium oxysporum, Pneumocystis jirovecii, Aspergillus* spp., *Coccidioides immitis/posadasii, Candida* sp., *Filobasidiella neoformans, Trichosporon, Encephalitozoon cuniculi, Enterocytozoon bieneusi, Mucor circinelloides, Rhizopus oryzae,* and *Lichtheimia corymbifera*.

15. A method of manufacturing the polypeptide of b) of claim 1 comprising chemically synthesizing the polypeptide or recovering the polypeptide from a cell expressing the polypeptide or a culture media surrounding the cell.

16. The method of claim 15, wherein:
a) the chemical synthesis comprises solid phase peptide synthesis; or
b) the cell is a prokaryotic cell, wherein, optionally, the prokaryotic cell is an *E. Coli*, or a eukaryotic cell, wherein, optionally, the eukaryotic cell is a HeLa, CHO, or HEK cell.

* * * * *

UNITED STATES PATENT AND TRADEMARK OFFICE
CERTIFICATE OF CORRECTION

PATENT NO. : 11,266,743 B2
APPLICATION NO. : 16/758791
DATED : March 8, 2022
INVENTOR(S) : William Charles Wimley et al.

Page 1 of 1

It is certified that error appears in the above-identified patent and that said Letters Patent is hereby corrected as shown below:

In the Claims

Column 88, Line 23, replace "(IL-21" with --(IL-2)--.

Column 89, Line 8, replace "inhibitor endothelin," with --inhibitor, endothelin,--;
    Line 26, replace "ATPase" with --ATPase,--.

Column 90, Line 25, replace "comprising (¶) delivering" with --comprising delivering--.

Column 92, Line 3, replace "*Streptococcus pyogenes, and Streptococcus pyogenes;*" with --*Streptococcus pyogenes*;--.

Signed and Sealed this
Second Day of August, 2022

Katherine Kelly Vidal
*Director of the United States Patent and Trademark Office*